US009434994B2

(12) United States Patent
Garcia et al.

(10) Patent No.: US 9,434,994 B2
(45) Date of Patent: Sep. 6, 2016

(54) METHODS FOR PREDICTION OF CLINICAL OUTCOME TO EPIDERMAL GROWTH FACTOR RECEPTOR INHIBITORS BY NON-SMALL CELL LUNG CANCER PATIENTS

(75) Inventors: Marileila Varella Garcia, Greenwood Village, CO (US); Paul A. Bunn, Jr., Evergreen, CO (US); Federico Cappuzzo, Bologna (IT); Wilbur A. Franklin, Denver, CO (US); Fred R. Hirsch, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/542,529

(22) Filed: Jul. 5, 2012

(65) Prior Publication Data

US 2013/0004970 A1    Jan. 3, 2013

Related U.S. Application Data

(63) Continuation of application No. 11/568,760, filed as application No. PCT/US2005/018879 on May 26, 2005, now abandoned.

(60) Provisional application No. 60/575,789, filed on May 27, 2004, provisional application No. 60/677,852, filed on May 3, 2005.

(51) Int. Cl.
*C12Q 1/00* (2006.01)
*C12Q 1/68* (2006.01)

(52) U.S. Cl.
CPC ....... *C12Q 1/6886* (2013.01); *C12Q 2600/106* (2013.01); *C12Q 2600/112* (2013.01); *C12Q 2600/118* (2013.01)

(58) Field of Classification Search
CPC combination set(s) only.
See application file for complete search history.

(56) References Cited

U.S. PATENT DOCUMENTS

| | | | |
|---|---|---|---|
| 5,369,108 A | 11/1994 | Breslow et al. | |
| 5,445,934 A | 8/1995 | Fodor et al. | |
| 5,635,596 A * | 6/1997 | Chambon et al. | 530/324 |
| 5,700,811 A | 12/1997 | Breslow et al. | |
| 5,747,498 A | 5/1998 | Schnur et al. | |
| 5,840,507 A * | 11/1998 | Fruehauf | 435/7.23 |
| 5,914,269 A | 6/1999 | Bennett et al. | |
| 5,932,616 A | 8/1999 | Breslow et al. | |
| 6,007,996 A * | 12/1999 | McNamara et al. | 435/6.14 |

(Continued)

FOREIGN PATENT DOCUMENTS

| | | |
|---|---|---|
| AU | 2003291736 | 6/2004 |
| EP | 659439 | 6/1995 |

(Continued)

OTHER PUBLICATIONS

Hirsch et al., Epidermal Growth Factor Receptor in Non-Small Cell Lung Carcinomas: Correlation Between Gene Copy Number and Protein Expression and Impact on Prognosis, J. Clin. Oncol. 21, 3798-3807, 2003.*

(Continued)

*Primary Examiner* — Elly-Gerald Stoica
(74) *Attorney, Agent, or Firm* — Sheridan Ross P.C.

(57) ABSTRACT

Disclosed are methods to obtain an expression score to evaluate gene expression in a tissue specimen obtained from a person having or suspected of having cancer.

1 Claim, 6 Drawing Sheets

TTP (months)

Survival (months)

A = Gene Amplification
B = High Polysomy
C = Low Polysomy
D = High Trisomy
E = Low Trisomy
F = Disomy

(56) References Cited

U.S. PATENT DOCUMENTS

| | | | |
|---|---|---|---|
| 6,040,138 A | 3/2000 | Lockhart et al. | |
| 6,087,367 A | 7/2000 | Breslow et al. | |
| 6,177,248 B1 | 1/2001 | Oliner et al. | |
| 6,355,678 B1 | 3/2002 | Uckun et al. | |
| 6,511,990 B1 | 1/2003 | Breslow et al. | |
| 6,596,878 B2 | 7/2003 | Chen et al. | |
| 6,794,392 B1 | 9/2004 | Suzuki et al. | |
| 6,962,789 B2 * | 11/2005 | Bacus | 435/7.23 |
| 8,017,321 B2 | 9/2011 | Bunn, Jr. et al. | |
| 2002/0045591 A1 | 4/2002 | Geiger et al. | |
| 2002/0102685 A1 | 8/2002 | Sibilia et al. | |
| 2003/0065156 A1 | 4/2003 | Williams et al. | |
| 2003/0087248 A1 | 5/2003 | Morrison et al. | |
| 2003/0114504 A1 | 6/2003 | Webster et al. | |
| 2003/0190689 A1 | 10/2003 | Crosby et al. | |
| 2004/0023267 A1 | 2/2004 | Morris | |
| 2004/0106141 A1 | 6/2004 | Mischel et al. | |
| 2004/0106605 A1 | 6/2004 | Carboni et al. | |
| 2004/0132097 A1 | 7/2004 | Bacus et al. | |
| 2004/0132825 A1 | 7/2004 | Bacopoulos et al. | |
| 2004/0202665 A1 * | 10/2004 | Lazarovits et al. | 424/178.1 |
| 2004/0248151 A1 | 12/2004 | Bacus et al. | |
| 2005/0043233 A1 | 2/2005 | Stefanic et al. | |
| 2005/0069963 A1 | 3/2005 | Lokshin et al. | |
| 2005/0136509 A1 * | 6/2005 | Gholap et al. | 435/40.5 |
| 2006/0166194 A1 * | 7/2006 | Ali Djamgoz et al. | 435/6 |
| 2006/0211060 A1 | 9/2006 | Haley et al. | |
| 2006/0234237 A1 | 10/2006 | Amler et al. | |
| 2007/0020261 A1 | 1/2007 | Sliwkowski et al. | |
| 2007/0031871 A1 | 2/2007 | Jove et al. | |
| 2007/0032513 A1 | 2/2007 | Hennequin et al. | |
| 2007/0043009 A1 | 2/2007 | Hennequin et al. | |
| 2007/0117815 A1 | 5/2007 | Pluda et al. | |
| 2007/0172844 A1 | 7/2007 | Lancaster et al. | |
| 2007/0197473 A1 | 8/2007 | Frankel et al. | |
| 2007/0197568 A1 | 8/2007 | Bunn et al. | |
| 2007/0212738 A1 | 9/2007 | Haley et al. | |
| 2007/0280928 A1 | 12/2007 | Buck et al. | |
| 2007/0281934 A1 | 12/2007 | Buggy et al. | |
| 2008/0015190 A1 | 1/2008 | Chakravarty et al. | |
| 2008/0015216 A1 | 1/2008 | Belvedere et al. | |
| 2008/0033015 A1 | 2/2008 | Belvedere et al. | |
| 2008/0085874 A1 | 4/2008 | Kushner et al. | |
| 2008/0090233 A1 | 4/2008 | Garcia et al. | |
| 2008/0096920 A1 | 4/2008 | Belvedere et al. | |
| 2008/0113874 A1 | 5/2008 | Bunn, Jr. et al. | |
| 2008/0182865 A1 | 7/2008 | Witta et al. | |
| 2008/0234265 A1 | 9/2008 | Witta et al. | |
| 2010/0196366 A1 | 8/2010 | Bunn et al. | |
| 2011/0294686 A1 | 12/2011 | Drabkin et al. | |
| 2012/0141479 A1 | 6/2012 | Witta et al. | |

FOREIGN PATENT DOCUMENTS

| | | |
|---|---|---|
| EP | 1236474 | 9/2002 |
| EP | 1510221 | 3/2005 |
| WO | WO 92/10588 | 6/1992 |
| WO | WO 95/35505 | 12/1995 |
| WO | WO 97/10365 | 3/1997 |
| WO | WO 02/05791 | 1/2002 |
| WO | WO 03/101491 | 12/2003 |
| WO | WO 04/000102 | 12/2003 |
| WO | WO 2004/030625 | 4/2004 |
| WO | WO 2004/046386 | 6/2004 |
| WO | WO 2004/063709 | 7/2004 |
| WO | WO 2004/071572 | 8/2004 |
| WO | WO 2004/111273 | 12/2004 |
| WO | WO 2005/027972 | 3/2005 |
| WO | WO 2005/067667 | 7/2005 |
| WO | WO 2005/070020 | 8/2005 |
| WO | WO 2005/094332 | 10/2005 |
| WO | WO 2005/117553 | 12/2005 |
| WO | WO 2006/005941 | 1/2006 |
| WO | WO 2006/005955 | 1/2006 |
| WO | WO 2006/017214 | 2/2006 |
| WO | WO 2006/017215 | 2/2006 |
| WO | WO 2006/061638 | 6/2006 |
| WO | WO 2006/082428 | 8/2006 |
| WO | WO 2006/099396 | 9/2006 |
| WO | WO 2006/110478 | 10/2006 |
| WO | WO 2006/115833 | 11/2006 |
| WO | WO 2006/115835 | 11/2006 |
| WO | WO 2006/115845 | 11/2006 |
| WO | WO 2007/002248 | 1/2007 |
| WO | WO 2007/025044 | 3/2007 |
| WO | WO 2007/029035 | 3/2007 |
| WO | WO 2007/029036 | 3/2007 |
| WO | WO 2007/052073 | 5/2007 |
| WO | WO 2007/055941 | 5/2007 |
| WO | WO 2007/055942 | 5/2007 |
| WO | WO 2007/072080 | 6/2007 |
| WO | WO 2007/087129 | 8/2007 |
| WO | WO 2007/087130 | 8/2007 |
| WO | WO 2007/093827 | 8/2007 |
| WO | WO 2007/100657 | 9/2007 |
| WO | WO 2007/107594 | 9/2007 |
| WO | WO 2007/127137 | 11/2007 |
| WO | WO 2007/136605 | 11/2007 |
| WO | WO 2008/010985 | 1/2008 |
| WO | WO 2008/033745 | 3/2008 |
| WO | WO 2008/033749 | 3/2008 |

OTHER PUBLICATIONS

U.S. Appl. No. 13/418,004, filed Mar. 12, 2012, Bunn et al.
Affymetrix GeneChip® Human Genome U133 Arrays datasheet. First published 2003.
Ahn et al. "Are there any ethnic differences in molecular predictors of erlotinib efficacy in advanced non-small cell lung cancer?" Clin Cancer Res. Jun. 15, 2008;14(12):3860-6. PMID: 18559606.
Al Moustafa et al., Lung Cancer. 37:49-56,2002.
Alberts et al., Molecular Biology of the Cell, 3rd edition, 1994, p. 465.
Allan, Nimotuzumab: Evidence of Clinical Benefit without Rash, The Oncologist, May 2005, vol. 10, No. 9, pp. 760-761.
Andrecheck et al. Proc Natl Acad Sc USA 2000; 97:3444-49.
Arteaga, Sem Oncol 2002;29:3-9.
Arteaga., Exp Cell Res 284:122-130,2003.
Bailey et al., Lung Cancer 2003;41 :s71 (abstr).
Barringer, et al., Gene, 89: 117-22 (1990).
Barsky et al., Cancer 73: 1163-1170, 1994.
Bartlett et al., J Pathol 2003; 199:411-7.
Baselga et al., "Phase I Safety, Pharmacokinetic, and Pharmacodynamic Trial of ZD1839, a Selective Oral Epidermal Growth Factor Receptor Tyrosine Kinase Inhibitor, in Patients with Five Selected Solid Tumor Types" Journal of Clinical Oncology, 2002, vol. 20, No. 21, pp. 4292-4302.
Batsche et al., Mol Cell Biol. 18(7):3647-58,1998.
Bell et al. "Epidermal growth factor receptor mutations and gene amplification in non-small-cell lung cancer: molecular analysis of the IDEAL/INTACT gefitinib trials." J Clin Oncol. Nov. 1, 2005;23(31):8081-92. Epub Oct. 3, 2005.PMID: 16204011.
Beste G, Schmidt FS, Stibora T, Skerra A., Small antibody-like proteins with prescribed ligand specificities derived from the lipocalin fold. Proc Natl Acad Sci U S A. Mar. 2, 1999;96(5):1898-903.
Bianco et al., Oncogene 2003;22:2812-22.
Bolos et al., J. Cell Sci. 116:499-511,2003.
Breathnach et al., Cancer 86: 1165-1173, 1999.
Bremnes et al., J Clin Oncol. 20:2417-2428,2002.
Brognard et al., Akt/protein kinase B is constitutively active in non-small cell lung cancer cells and promotes cellular survival and resistance to chemotherapy and radiation. Cancer Research, 2001, vol. 61, pp. 3986-3997.
Bruzzese et al. "Synergistic antitumor effect of the histone deacetylase inhibitor suberoylanilide hydroxamic acid (SAHA) in combination with the epidermal growth factor receptor tyrosine kinasse inhibitor gefitinib ('Iressa', ZD1839) in squamous-cell carcinoma of the head and neck derived cell lines" Proc. Amer. Assoc. Cancer Res., vol. 45, 2004, abstract #5625.

(56) References Cited

OTHER PUBLICATIONS

Cancer Network "Panels of Markers for Erlotinib and Gefitinib Sensitivity Found in NSCLC Cell Lines," Oncology News International, Jan. 2005, vol. 14, No. 1, 2 pages.
Cano et al., Nat. Cell Biol. 2:76-83, 2000.
Cappuzzo F, Finocchiaro G, Rossi E et al.: EGFR FISH assay predicts for response to cetuximab in chemotherapy refractory colorectal cancer patients. Ann. Oncol. 19, 717-723 (2008).
Cappuzzo et al., J Clin Oncol. 21(14):2658-63,2003.
Cappuzzo et al., J. Natl Cancer Inst 2004;96: 1133-41.
Cappuzzo et al., Proc Am Soc Clin Oncol, 2004; 22 :3004.
Cappuzzo et al. "Epidermal Growth Factor Receptor Gene and Protein and Getinib Sensitivity in Non-Small-Cell Lung Cancer", Journal of the National Cancer Institute, vol. 97, No. 9, May 4, 2005, pp. 1-13.
Cappuzzo et al. "Epidermal growth factor receptor gene and protein and gefitinib sensitivity in non-small-cell lung cancer." J Natl Cancer Inst. May 4, 2005;97(9):643-55.PMID: 15870435.
Cappuzzo et al. "Prospective study of gefitinib in epidermal growth factor receptor fluorescence in situ hybridization-positive/phospho-Akt-positive or never smoker patients with advanced non-small-cell lung cancer: the ONCOBELL trial." J Clin Oncol. Jun. 1, 2007;25(16):2248-55.PMID: 17538169.
Cappuzzo et al., EGFR and HER2 gene copy number and response to first-line chemotherapy in patients with advanced non-small lung cancer. Journal of Thoracic Oncology, 2007. vol. 2, pp. 423-429.
Chemotherapy in non-small cell lung cancer: a meta-analysis using updated data on individual patients from 52 randomised clinical trials. Non-small Cell Lung Cancer Collaborative Group. BMJ 1995;311:899-909.
Chinnadurai, Mol. Cell 9, 213-224, 2002.
Chinnaiyan et al. "Enhancing the anti-tumor activity of ErbB blockade with histone deacetylase (HDAC) inhibition", Journal of Clinical Oncology, 2004 ASCO Annual Meeting Proceedings, vol. 22, No. 14S, 3029.
Christensen et al. "High Levels of HER-2 Expression Alter the Ability of Epidermal Growth Factor Receptor (EGFR) Family Tyrosine Kinase Inhibitors to Inhibit EGFR Phosphorylation in Vivo," Clinical Cancer Research, Dec. 2001, vol. 7, No. 12, pp. 4230-4238.
Ciardello and Tortora, Clin Cancer Res 2001;7:2958-70.
Ciardiello et al., Clin Cancer Res 2000;6:2053-63.
Cohen et al. "United States Food and Drug Administration Drug Approval Summary: Gefitinib (ZD1839: Iressa) Tablets." Clinical Cancer Research, Feb. 15, 2004, vol. 10, pp. 1212-1218.
Comijn et al., Mol Cell ;7(6): 1267-78,2001.
Conacci-Sorrell et al., J Cell Biol. 163(4):847-57,2003.
Cowley et al., J Pathol. 179: 183-7, 1996.
Cox,J R Stat Soc B 1972;34:187-220.
Datta SR, Genes and Development 1999; 13:2905-27.
de Ruijter et al., Biochem J.370:737-749, 2003.
Deeb et al., "Altered E-Cadherin and Epidermal Growth Factor Receptor Expressions are Associated with Patient Survival in Lung Cancer: A Study Utilizing High-Density Tissue Microarray and Immunochemistry", Modern Pathology, 2004, vol. 17, pp. 430-439.
Demetri et al., N Engl J Med 2002; 347:472-80.
DeRisi J, Penland L, Brown PO, Bittner ML, Meltzer PS, Ray M, Chen Y, Su YA, Trent JM, Use of a cDNA microarray to analyse gene expression patterns in human cancer. Nat Genet. Dec. 1996;14(4):457-60. (Abstract Only).
DiGiuseppe et al., Leukemia 13:1243-1253, 1999.
Druker et al., N Engl J Med 2001; 344: 1031-7.
Drummond et al., "Enhanced Pharmacodynamic and Antitumor Properties of a Histone Deacetylase Inhibitor Encapsulated in Liposomes or ErbB2-Targeted Immunoliposomes", Clin Cancer Res, May 1, 2005, 11(2), pp. 3392-3401.
Dumstrei et al., Development; 129(17):3983-94, 2002.
Dziadzuiszko et al., Epidermal growth factor receptor gene copy number and protein level are not associated with outcome of non-small cell lung cancer patients treated with chemotherapy. Annals of Oncology, 2007, vol. 18, pp. 447-452.
Eger et al. DeltaEF1 is a transcriptional repressor of E-cadherin and regulates epithelial plasticity in breast cancer cells. Oncogene, Mar. 31, 2005, vol. 24, No. 14, pp. 2375-2385.
Engelman et al., Cancer Research, Dec. 2007, vol. 67, pp. 11924-11932.
Felip et al. "A phase II pharmacodynamic study of erlotinib in patients with advanced non-small cell lung cancer previously treated with platinum-based chemotherapy." Clin Cancer Res. Jun. 15, 2008;14(12):3867-74. PMID: 18559607.
Frederick et al., Cancer Res 2000; 60, 1383-87.
Fricke et al., Oncology 66(2):150-9,2004.
Fu et al., EMBO Journal, 1996, vol. 15, pp. 4392-4401.
Fuino et al., "Histon Deacetylase Inhibitor LAQ824 Down-Regulates Her-2 and Sensitizes Human Breast Cancer Cells to Transtuzumab, Taxotere, Gemcitabine, and Epothilone B." Molecular Cancer Therapeutics, 2003, vol. 2, pp. 971-984.
Fukuoka et al., J Clin Oncol. 21:2237-2246,2003.
Furak et al., European J Cardio-Thoracic Surgery 23:818-823,2003.
Gandara et al., Clin Cancer Res, Jun. 15, 2004;10(12 Pt 2):4205s-4209s.
Giaccone et al., J Clin Oncol 2004;22:777-84.
Gore et al., 2004 ASCO Annual Meeting Proceedings vol. 22, No. 14S (Jul. 15 Supplement): 3026, 2004.
Greenbaum et al., Genome biology, 2003, vol. 4, Issue 9, pp. 117.1-117.8.
Guatelli, et al, Proc. Nat. Acad. Sci. USA, 87: 1874 (1990).
Hacia JG, Brody LC, Chee MS, Fodor SP, Collins FS, Detection of heterozygous mutations in BRCA1 using high density oligonucleotide arrays and two-colour fluorescence analysis. Nat Genet. Dec. 1996;14(4):441-7. (Abstract Only).
Hajra et al., Cancer Res. 62:1613-1618,2002.
Han et al., J Clin Oncol. Apr. 10, 2005;23(11):2493-501. Epub Feb. 14, 2005.
Herbst et al., J Clin Oncol. 2002;20:3815-25.
Hidalgo et al.,J Clin Oncol. 2001;19:3267-79.
Hirashima et al. "Protein Overexpression and Gene Amplification of c-erb B-2 in Pulmonary Carcinomas: A Comparative Immunohistochemical and Fluorescence In Situ Hybridization Study," Modern Pathology, Jun. 2001, vol. 14, No. 6, pp. 556-562.
Hirsch et al. "The Role of HER2/neu Expression and Trastuzumab in Non-Small Cell Lung Cancer." Seminars in Oncology, Feb. 2004, vol. 31, No. 1, Supplemental 1, pp. 75-82.
Hirsch et al., "Evaluation of HER-2/neu gene amplification and protein expression in non-small cell lung carcinomas" Br J Cancer 86: 1449-1456,2002.
Hirsch et al., J Clin Oncol, 2003;21:3798-807.
Hirsch et al., Lung Cancer 41 Suppl 1:S29-42, 2003.
Hirsch et al. "Increased epidermal growth factor receptor gene copy number detected by fluorescence in situ hybridization associates with increased sensitivity to gefitinib in patients with bronchioloalveolar carcinoma subtypes: a Southwest Oncology Group Study.", J Clin Oncol. Oct. 1, 2005;23(28):6838-45. Epub Jul. 5, 2005.PMID: 15998906.
Hirsch FR, Varella-Garcia M, Bunn PA Jr et al.: Molecular predictors of outcome with gefitinib in a Phase III placebo-controlled study in advanced NSCLC. J. Clin. Oncol. 24(31), 5034-5042 (2006).
Hirsch et al., Combination of EGFR gene copy number and protein expression predicts outcome for advanced non small cell lung cancer patients treated with gefitnib. Annals of Oncology, 2007, vol. 18, pp. 752-760.
Huelsken et al., Current Opin. Genet. Dev. 11,547-553,2001.
Janmaat et al., Clin Cancer Res 2003;9:2316-26.
Jemal et al., CA Cancer J Clin. 54(1):8-29,2004.
Jiang, Br J Surg 83: 437-446, 1996.
Jones, et al., "E-cadherin relates to EGFR expression and lymph node metastasis in primary breast carcinoma," British Journal of Cancer, 1996, vol. 74, pp. 1237-1241.
Jorissen et al., Exp Cell Res 284:31-53,2003.
Kaplan and Meier, J Am Stat Assoc 1985;53:457-81.
Kelly et al., J Clin Oncol. 2001; 19:3210-8.

(56) References Cited

OTHER PUBLICATIONS

Kim et al., Clinical Cancer Res, 11:2244, 2005.
Kintner, Cell 69: 225-236, 1992.
Knowlden et al., Oncogene, 1999, 17: pp. 1949-1957.
Kohler and Milstein, Nature 256:495-497, 1975.
Kraker et al. Modulation of histone acetylation by [4-(acetylamino)-N-(2-amino-phenyl)benzamide] in HCT-8 colon carcinoma. Mol. Cancer. Ther., Apr. 2003, vol. 2, No. 4, pp. 401-408.
Kris et al., J. Am. Med. Assoc. 290,2149-2158,2003.
Kris et al., Lung Cancer 2000; Suppl 1;72:233 abstract.
Kuwada et al., "Effects of Trastuzumab on epidermal growth factor receptor-dependent and -independent human colon cancer cells" International Journal of Cancer, John Wiley & Sons, Inc. Mar. 20, 2004, pp. 291-301.
Kwoh, et al., Proc. Natl. Acad. Sci. USA, 86: 1173 (1989).
Landegren, et al., Science, 241: 1077 (1988).
Levitt and Koty, Investig New Drugs 1999;7:213-26.
Levitzki and Gazit, Science 267: 1782-8, 1995.
Lewin, Genes VI, Oxford University Press, Inc., NY, Chapter 29, 1997.
Lockhart DJ, Dong H, Byrne MC, Follettie MT, Gallo MV, Chee MS, Mittmann M, Wang C, Kobayashi M, Horton H, Brown EL. Expression monitoring by hybridization to high-density oligonucleotide arrays. Nat Biotechnol. Dec. 1996;14(13):1675-80. (Abstract Only).
Lu et al., Cancer Cell. 4(6):499-515, 2003.
Lynch et al., N Engl J Med 350:2129-39,2004.
Mallampalli et al., Biochem. J. vol. 318, 1996, pp. 333-341.
Mantel N, Cancer Chemother Rep 50:163-170,1966.
Marks et al., J Natl Cancer Inst (Bethesda),92:1210-6, 2000.
Matei et al., Imatinib mesylate (Gleevec) inhibits ovarian cancer cell growth through a mechanism dependent on platelet-derived growth factor receptor alpha and Akt inactivation, Clinical Cancer Research, Jan. 15, 2004, vol. 10, No. 2, pp. 681-690.
Meinkoth et al., Anal. Biochem. 138, 267-284.
Mendelsohn et al. Status of Epidermal Growth Factor Receptor Antagonists in the Biology and Treatment of Cancer. Journal of Clinical Oncology, Jul. 15, 2003, vol. 21, No. 14, pp. 2787-2799.
Miller et al., J Clin Oncol. 2004;22: 1103-9.
Miller et al., Proc Am Soc Clin Oncol 2003;22 (abstract 2491).
Mitsudomi et al. J Clin Oncol. 23:2513, 2005.
Monnert "Histone Deacetylase Inhibitors", European Journal of Medicinal Chemistry, 2005, vol. 40, pp. 1-13.
Nakamura et al. "Correlation Between Encoded Protein Overexpression and Copy Number of the Her2 Gene With Survival in Non-Small Cell Lung Cancer," International Journal of Cancer, Jan. 1, 2003, vol. 103, No. 1, pp. 61-66.
Nimannapalli et al. Histone Deacetylase Inhibitor LAQ824 Both Lowers Expression and Promotes Proteasomal Degradation of Bcr-Abl and Induces Apoptosis of Irnatmlb Mesylate-sensitive or -refractory Chronic Myelogenous Leukemia-Blast Crisis Cells. Cancer Research, Aug. 15, 2003, vol. 63, No. 16, pp. 5126-5135.
Ohira et al., Proc Natl Acad Sci USA. 100:10429-10434,2003.
Oken et al., Am J Clin Oncol, 1982; 5:649-655.
Ono et al., Mol Cancer Ther 2004;3 :465-72.
O'Shannessy DJ, Brigham-Burke M, Soneson KK, Hensley P, Brooks I., Determination of rate and equilibrium binding constants for macromolecular interactions using surface plasmon resonance: use of nonlinear least squares analysis methods. Anal Biochem. Aug. 1, 1993;212(2):457-68. (Abstract Only).
Ozawa et al., EMBO J. 8: 1711-1717, 1989.
Paez et al., "EGFR mutations in lung cancer: Correlation with clinical response to gefitinib therapy." Science (Wash DC) 304:1497-500, 2004.
Pao et al., Proc Natl Acad Sci USA 101(36):13306-11, 2004.
Parkin, The Lancet Oncology 2:533-543,2001.
Parra et al., Brit J Cancer, 91: 208-212, 2004.
Patel et al., Lung Cancer 41 :S56, 2003 (suppl2).
Pece and Gutkind, J Biol Chem. 275(52):41227-33,2000.
Pece et al., J Biol Chem 274(27):19347-51, 1999.
Perez-Soler et al., J Clin Oncol 2004;22:3238-47.
Perez-Soler et al., Proc. Am. Soc. Clin. Oncol., 20: 310a (1235) 2001.
Personeni N, Fieuws S, Piessevaux H et al.: Clinical usefulness of EGFR gene copy number as a predictive marker in colorectal cancer patients treated with cetuximab: a fluorescent in situ hybridization study. Clin. Cancer Res. 14(18), 5869-5876 (2008).
Polowy et al., Proc Am Soc Clin Oncol 22: 2003 (abstr 2845), pp. 1-3.
Postigo and Dean, Proc. Natl. Acad. Sci. USA 96, pp. 6683-6688, 1999.
Qian et al.,EMBO J. 23:1739-84,2004.
Ranson et al., J Clin Oncol. 2002;20:2240-50.
Reginato et al., Nat Cell Biol. 5(8):733-40, 2003.
Reissmann et al., J Cancer Res Clin Oncol, 1999;125:61-70.
Rosell et al.; Clin Cancer Res 2004;10:1318-25.
Rosivatz et al., Int J Cancer 111(5):711-9, 2004.
Saito et al. Proc. Natl. Acad. Sci. USA. Apr. 1999, vol. 96, pp. 4592-4597.
Salomon et al., Crit Rev Oncol Hematol, 1995;19:183-232.
Sartore-Bianchi A, Moroni M, Veronese S et al.: Epidermal growth factor receptor gene copy number and clinical outcome of metastatic colorectal cancer treated with panitumumab. J. Clin. Oncol. 25, 3238-3245 (2007).
Satoh et al., Biocell. 27(1):47-55,2003.
Schiller et al., N Engl J Med 2002;346:92-8.
Schuster SC, Swanson RV, Alex LA, Bourret RB, Simon MI., Assembly and function of a quaternary signal transduction complex monitored by surface plasmon resonance. Nature. Sep. 23, 1993;365(6444):343-7.
Seiichi et al. "EGFR tyrosine kinase inhibitor "gefitinib (iressa)" for cancer therapy." Folia Pharmacologica Japonica, 2003, Japan, vol. 122, No. 6, pp. 491-497, English abstract included.
Sekido et al., Mol Cell Biol. 14:5692-700, 1994.
Shepherd et al., Journal of Clinical Oncology, 2004 ASCO Annual Meeting Proceedings (Post-Meeting Edition). vol. 22, No. 14S (Jul. 15 Supplement), 2004: 7022.
Shrader et al., "Molecular correlates gefitinib responsiveness in human bladder cancer cells," Molecular Cancer Therapeutics, 2007, vol. 6, pp. 277-285.
Sirotnak et al., Clin Cancer Res 2000;6:4885-92.
Slamon et al., N Engl J Med 2001; 344:783-92.
Slamon et al., Science 235:177-182,1987.
Sordella et al., Science 2004;305:1163-7.
Stribling R, Brunette E, Liggitt D, Gaensler K, Debs R., Aerosol gene delivery in vivo. Proc Natl Acad Sci U S A. Dec. 1, 1992;89(23):11277-81.
Sulzer et al., Am J. Respir, 1998, vol. 157, pp. 1319-1323.
Suzuki et al., Lung Cancer;42(1):35-41, 2003.
Takano et al. "Epidermal growth factor receptor gene mutations and increased copy numbers predict gefitinib sensitivity in patients with recurrent non-small-cell lung cancer." J Clin Oncol. Oct. 1, 2005;23(28):6829-37. Epub Jul. 5, 2005.PMID: 15998907.
Tamura "Feature Article New Approach to Nonoperative Lung Cancer Therapy 5. Molecular-Targeted Therapy —EGFR Inhibitor —," Journal of Japan Surgical Society, Feb. 1, 2002, vol. 103, No. 2, p. 233-236.
Testa eta l. "Chromosome Abnormalities in Human Non-Small Cell Lung Cancer," Cancer Research, May 1, 1992, vol. 52, 9 Supplemental, pp. 2702s-2706s.
Thatcher N, Chang A, Parikh P et al.: Gefitinib plus best supportive care in previously treated patients with refractory advanced non-small-cell lung cancer: results from a randomised, placebo-controlled, multicentre study (Iressa Survival Evaluation in Lung Cancer). Lancet 366, 1527-1537 (2005).
Therasse et al, J Natl. Cancer Inst. Feb. 2, 2000; 92(3):205-16; available at http://ctep.cancer.gov/forms/TherasseRECISTJNCI.pdf.
Thomson et al., "Epithelial to mesenchymal transition is a determinant of sensitivity of non-small-cell lung carcinoma cell lines and xenografts to epidermal growth factor receptor inhibition," Cancer Research, 2005, vol. 65, pp. 9455-9462.

(56) References Cited

OTHER PUBLICATIONS

Tiseo et al. "Predictors of gefitinib outcomes in advanced non-small cell lung cancer (NSCLC): Study of a comprehensive panel of molecular markers." Lung Cancer. Epub May 25, 2009. PMID: 19473722.
Tockman et al., Cancer Res., 1992, 52:2711s-2718s.
Tracy et al,. Cancer Res, 2004; 64:7241-44.
Tsao M-S, Sakurada A, Cutz J-C et al.: Erlotinib in lung cancer—molecular and clinical predictors of outcome. N. Engl. J. Med. 353(2), 133-144 (2005).
Tsurutani et al. "Antiproliferative effects of the histone deacetylase inhibitor FR901228 on small-cell lung cancer lines and drug-resistant sublines," Int. J. Cancer, Mar. 20, 2003, vol. 104, No. 2, p. 238-242.
Van Cutsem E, Peeters M, Siena S et al.: Open-label Phase III trial of panitumumab plus best supportive care compared with best supportive care in patients with chemotherapy-refractory metastatic colorectal cancer. J. Clin. Oncol. 25, 1658-1664 (2007).
van Grunsven et al., J Biol Chem. 278:26135-26145, 2003.
Varella-Garcia et al. "EGFR and HER2 genomic gain in recurrent non-small cell lung cancer after surgery: impact on outcome to treatment with gefitinib and association with EGFR and KRAS mutations in a Japanese cohort." J Thorac Oncol. Mar. 2009;4(3):318-25.PMID: 19247083.
Verschueren et al., J Biol Chem. 274:20489-98, 1999.
Vogel et al., J Clin Oncol, 2002;20:719-26.
West et al., Advanced bronchioloalveolar carcinoma: a phase II trial ofpaclitaxel by 96-h infusion (SWaG 9714): a Southwest Oncology Group study. Ann Oncol. Jul. 2005;16(7):1076-80. Epub Apr. 28, 2005.
Witta et al. "Expression of E-cadherin inhibitory zinc finger transcription factors δEF1/ZEB1 and SIP1/ZEB2 correlates with resistance to EGFR inhibitors." Proceedings of the American Association for Cancer Research, 2004, vol. 45, Abstract # 3671, 2 pages.
Witta et al. "Overcoming resistance to EGFR inhibitors in NSCLC cell lines by sequential treatment with histone deacetylase inhibitors", Journal of Clinical Oncology, 2005 ASCO Annual Meeting Proceedings, vol. 23, No. 16S, 7083.
Witta et al., "Genes and Proteins Involved in Predicting Sensitivity/Resistance to Gefitinib in Lung Cancer", presented at the Oct. 29, 2004 Meeting for the European Society for Medical Oncology (EMSO), 1 page.
Witta et al., "Restoring E-cadherin expression increases sensitivity to epidermal growth factor receptor inhibitors in lung cancer cell lines", Cancer Res., Jan. 15, 2006; 66(2), pp. 944-950.
Wu and Wallace, Genomics, 4: 560 (1989).
Yarden and Sliwkowski, Nat Rev Mol Cell Bioi. 2:127-137,2001.
Yu et al., Modulation of p53, ErbB1, ErbB2, and Raf-1 expression in lung cancer cells by depsipeptide FR901228,: J. Natl. Cancer Inst., Apr. 3, 2002, vol. 94, No. 7, p. 504-513.
Zelent et al., Clin Cancer Res 10: 4622-4629,2004.
Zhu C-Q, Cunha Santos G, Ding K et al.: Role of KRAS and EGFR as biomarkers of response to erlotinib in National Cancer Institute of Canada Clinical Trials Group Study BR.21. J. Clin. Oncol. 26(26), 4268-4275 (2008).
International Search Report for International (PCT) Patent Application No. PCT/US05/18879, mailed May 2, 2008.
Written Opinion for International (PCT) Patent Application No. PCT/US05/18879, mailed May 2, 2008.
Examiner's First Report on Australian Patent Application No. 2005249492, mailed Dec. 10, 2009.
Supplementary European Search Report for European Application No. 05755989.0, dated Jul. 2, 2009.
Official Action for European Patent Application No. 05755989.0, mailed Jan. 5, 2011.
English translation of Official Action for Japapan Patent Application No. 2007-515430, mailed Mar. 8, 2011 5 pages.
Official Action with English translation for Japan Patent Application No. 2007-515430, mailed Jan. 24, 2012 3 pages.
Official Action for Canada Patent Application No. 2,567,293, mailed Feb. 14, 2012 3 pages.
Official Action for U.S. Appl. No. 11/568,760, mailed May 7, 2010.
Official Action for U.S. Appl. No. 11/568,760, mailed Sep. 1, 2009.
Nakanishi et al., "Molecular-Targeted Therapy for Cancer Metastasis "Histone Deacetylase Inhibitor"," (with English translation), Journal of Clinical and Experimental Medicine (Igaku no Ayumi), Sep. 23, 2000, vol. 194, No. 13, 5 pages.
Saijo "New Attempt to treat cancer (English Translation)," Iyaku Journal Co. Ltd., May 31, 2000, pp. 20-21 and 33-35.
Examination Report for Australia Patent Application No. 2011265464, dated Jul. 26, 2012 4 pages.
Examination Report for Australia Patent Application No. 2011265464, dated Sep. 14, 2012 2 pages.
Search Report for European Patent Application No. 12005855.7, dated Oct. 2, 2012 10 pages.
Official Action for European Patent Application No. 05755989.0, dated Oct. 8, 2012 8 pages.
English Translation of Official Action for Japan Patent Application No. 2007-515430, dated Aug. 21, 2012 3 pages.
Tidow et al., "Distinct amplification of an untranslated regulatory sequence in the egfr gene contributes to early steps in breast cancer development," Cancer Res., 2003, vol. 63(6), pp. 1172-1178.
Official Action for Canada Patent Application No. 2,567,293, mailed Oct. 21, 2013 2 pages.
Notice of Allowance (including English translation) for Japan Patent Application No. 2007-515430, mailed Oct. 29, 2013 2 pages.
Official Action for U.S. Appl. No. 11/568,760, mailed Nov. 7, 2013, 19 pages.
Official Action for Canada Patent Application No. 2,567,293, mailed Feb. 11, 2013 3 pages.
Examination Report for Australia Patent Application No. 2011265464, dated Aug. 22, 2013 3 pages.
Notice of Acceptance for Australia Patent Application No. 2011265464, dated May 2, 2014 2 pages.
Official Action for European Patent Application No. 12005855.7, dated Nov. 5, 2013 8 pages.
Intent to Grant for European Patent Application No. 12005855.7, dated Jul. 2, 2014 5 pages.
Final Action for U.S. Appl. No. 11/568,760, mailed Apr. 17, 2014 8 pages.
Bailey et al., "Tumor EGFR membrane staining is not clinically relevant for predicting response in patients receiving gefitinib ('Iressa' ZD1839) monotherapy for pretreated advanced non-small-cell lung cancer: IDEAL 1 and 2," Proceedings of the American Association for Cancer Research, 2003, vol. 44, Abstract #LB-170, p. 1362.
Choi et al., "Transcriptional Profiling of Non-Small Cell Lung Cancer Cells with Activation EGFR Somatic Mutations," PLoS ONE, 2007, Iss. 11, 11 pages.
De Risi et al. "Use of a cDNA microarray to analyse gene expression patterns in human cancer," Nature Genetics, Dec. 1996, vol. 14, No. 4, pp. 457-460.
Hacia et al. "Detection of heterozygous mutations in BRCA1 using high density oligonucleotide arrays and two-colour fluorescence analysis," Nature Genetics, Dec. 1996, vol. 14, No. 4, pp. 441-447.
Kim C, Bryant J, Horne Z, et al: Trastuzumab sensitivity of breast cancer with co-amplification of HER2 and cMYC suggests pro-apoptotic function of dysregulated cMYC in vivo. Breast Cancer Res Treat 94:S6-S7, 2005 (abstract No. 46)—2 pages.
Kohler et al. "Continuous cultures of fused cells secreting antibody of predefined specificity," Nature, Aug. 7, 1975, vol. 256, No. 5517, pp. 495-497.
O'Shannessy et al. "Determination of Rate and Equilibrium Binding Constants for Macromolecular Interactions Using Surface Plasmon Resonance: Use of Nonlinear Least Squares Analysis Methods," Analytical Biochemistry, Aug. 1993vol. 212, No. 2, pp. 457-468.
Perez, E.A., et al. J Clinical Oncology, C-MYC alterations and association with patient outcome in early-stage HER2-positive breast cancer from the north central cancer treatment group N9831 adjuvant trastuzumab trial, 29(6):651-659, 2011—9 pages.

(56) References Cited

OTHER PUBLICATIONS

Zhang et al. "An Oncogenic Role for the Phosphorylated h-Subunit of Human Translation Initiation Factor eIF3." Journal of Biological Chemistry, Aug. 29, 2008, vol. 238, No. 55, pp. 24047-24060.
International Search Report for International (PCT) Patent Application No. PCT/US09/56629, mailed Feb. 24, 2010.
Written Opinion for International (PCT) Patent Application No. PCT/US09/56629, mailed Feb. 24, 2010.
International Preliminary Report on Patentability for International (PCT) Patent Application No. PCT/US2009/056629, mailed Mar. 24, 2011 6 pages.
Official Action for U.S. Appl. No. 11/568,760, mailed Mar. 12, 2013, 19 pages.
Official Action for U.S. Appl. No. 13/063,260 mailed Feb. 22, 2013, 7 pages.
Examination Report for Australia Patent Application No. 2011265464, dated Mar. 24, 2014 4 pages.
Official Action for U.S. Appl. No. 11/568,760, mailed Dec. 29, 2014 11 pages.
Official Action for U.S. Patent Application No. 05755989.0, dated Sep. 30, 2014 6 pages.
Intention to Grant Patent for European Patent Application No. 05755989.0, dated Mar. 19, 2015 113 pages.
Official Action for Australia Patent Application No. 2014213541, dated Nov. 13, 2015 3 pages.
Extended Search Report for European Patent Application No. 15177716.6, dated Sep. 4, 2015 11 pages.
Official Action for U.S. Appl. No. 11/568,760, mailed May 20, 2015 12 pages.

\* cited by examiner

A = Gene Amplification
B = High Polysomy
C = Low Polysomy
D = High Trisomy
E = Low Trisomy
F = Disomy

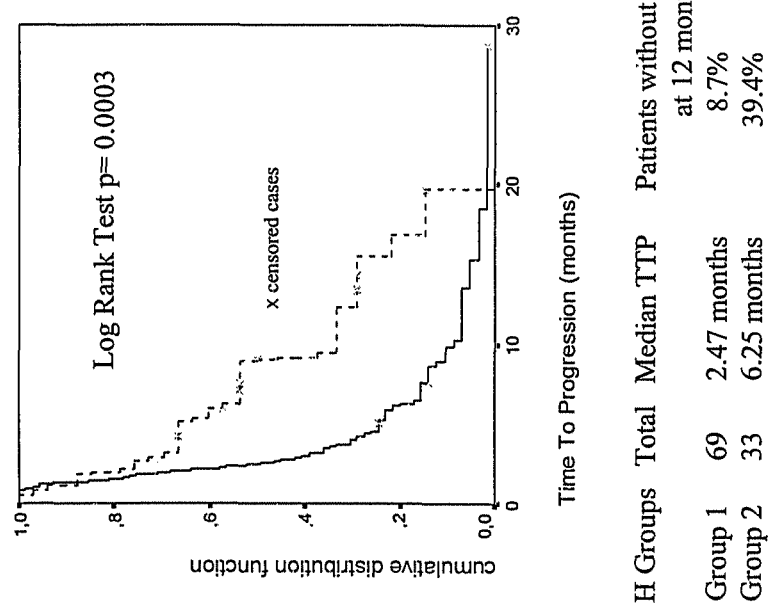

METHODS FOR PREDICTION OF CLINICAL OUTCOME TO EPIDERMAL GROWTH FACTOR RECEPTOR INHIBITORS BY NON-SMALL CELL LUNG CANCER PATIENTS

CROSS REFERENCE TO RELATED APPLICATION

This application is a continuation of U.S. patent application Ser. No. 11/568,760 filed Nov. 9, 2007, which is a national stage application under 35 U.S.C. §371 of PCT Application No. PCT/US05/18879, having an international filing date of May 26, 2005, which designated the United States, which PCT application claimed the benefit of U.S. Provisional Patent Application No. 60/677,852 filed May 3, 2005, and U.S. Provisional Patent Application No. 60/575,789 filed May 27, 2004. All of these priority documents are incorporated herein, in their entirety, by this reference.

GOVERNMENT INTEREST

This invention was made with government support under grant numbers CA46934 and CA58187 awarded by the National Institutes of Health. The U.S. government has certain rights in the invention.

FIELD OF THE INVENTION

The present invention generally relates to biomarkers, methods and assay kits for the identification of cancer patients who are predicted to benefit from EGFR inhibitor therapy.

BACKGROUND OF THE INVENTION

Neoplasia, or a process of rapid cellular proliferation resulting in new, abnormal growth, is a characteristic of many diseases which can be serious, and sometimes, life-threatening. Typically, neoplastic growth of cells and tissues is characterized by greater than normal proliferation of cells, wherein the cells continue to grow even after the instigating factor (e.g., tumor promoter, carcinogen, virus) is no longer present. The cellular growth tends to show a lack of structural organization and/or coordination with the normal tissue and usually creates a mass of tissue (e.g., a tumor) which may be benign or malignant. Malignant cellular growth, or malignant tumors (cancer), are a leading cause of death worldwide, and the development of effective therapy for neoplastic disease is the subject of a large body of research. Although a variety of innovative approaches to treat and prevent cancers have been proposed, many cancers continue to cause a high rate of mortality and may be difficult to treat or relatively unresponsive to conventional therapies. In addition, patients may respond differently to various cancer therapies, making some approaches useful for some patients and not for others. Therefore, there is a continuing need in the art for the identification of additional cancer risk factors and methods for early diagnosis and therapy for cancers, as well as methods for identifying patients that are expected to benefit from a particular type of therapy.

Illustrating this point, non-small cell lung cancer (NSCLC) is the leading cause of cancer death in the world. While chemotherapy has produced modest survival benefits in advanced stages, standard two-drug combinations generate considerable toxicity and require intravenous administration (Non-small Cell Lung Cancer Collaborative Group, 1995; Schiller et al., 2002; Kelly et al., 2001). Progress in the field of lung cancer biology led to the development of small molecule inhibitors of target proteins involved in the proliferation, apoptosis and angiogenesis. Targeted therapy agents such as imatinib and trastuzumab produced consistent survival benefit in chronic myeloid leukemia (Druker, 2001), gastrointestinal stromal tumors (GIST) (Demetri 2002) and breast cancers that overexpress the target proteins (Slamon 2001). The epidermal growth factor receptor (EGFR) superfamily, including the four distinct receptors EGFR/erbB-1, HER2/erbB-2, HER3/erbB-3, and HER4/erbB-4, was early identified as a potential therapeutic target in solid tumors. After ligand binding, these receptors homo- and heterodimerize, and the tyrosine-kinase domain is activated, initiating a cascade of events implicated in the development and progression of cancer through effects on cell-cycle progression, apoptosis, angiogenesis, and metastasis (Salomon et al., 2001; Arteaga, 2002; Hirsch et al., 2003, *Lung Cancer*; Ciardello and Tortora, 2001). EGFR is overexpressed in many human epithelial malignancies, including NSCLC (Hirsch et al., 2003, *J. Clin. Oncol.*; Salomon et al., 1995).

Given the biological importance of the EGFR molecular network in carcinomas, several molecules were synthesized to inhibit the tyrosine kinase domain of EGFR (Levitzki and Gazit, 1995; Levitt and Koty, 1999). Among the most promising of these new drugs are gefitinib (ZD 1839, Iressa®, AstraZeneca, UK), and erlotinib (OSI 774, Tarceva®, Genentech, USA). Both are orally active, selective EGFR tyrosine-kinase inhibitors (EGFR-TKI) that demonstrated antitumor activity against a variety of human cancer cell lines expressing EGFR (Ciardiello et al., 2000). Likewise, both have well documented activity as single agents in phase I studies, including chemotherapy resistant NSCLC patients who had response rates of about 10% (Kris et al., 2000, *Lung Cancer*; Baselga et al., 2002; Herbst et al, 2002; Ranson et al., 2002; Hidalgo et al., 2001). Activity was confirmed in large phase II trials showing response rates of 19-26% in previously untreated, advanced NSCLC patients, and 12-18% in patients who had failed one or more prior chemotherapy combinations (Fukuoka et al., 2003; Kris et al., 2003, *JAMA*; Perez-Soler et al., 2001; Miller et al., 2003). More recently, a phase III trial (BR21) comparing erlotinib with placebo as a second or third line therapy reported a survival benefit for the EGFR inhibitor (Hazard Ratio: 0.73) (Shepherd et al., 2004). Importantly, this survival benefit was not confined to objective responders, nor to a single gender or histology, which makes selection based on clinical and histopathological features alone difficult.

In phase II trials with gefitinib, no correlation was detected between EGFR protein expression and response to therapy, although few studies have directly addressed this question. Patients with squamous cell carcinomas had lower response rates compared to patients with adenocarcinoma despite their higher rates of EGFR expression (Ciardiello et al., 2000; Fukuoka et al., 2003; Kris et al., 2003, *JAMA*). Recent reports showed that specific missense and deletion mutations in the tyrosine kinase domain of the EGFR gene (Lynch et all, 2004; Paez et al., 2004) are significantly associated with gefitinib sensitivity. However, while objective response has been reported in up to 18% and symptomatic improvement in 40% of the unselected gefitinib treated NSCLC patients (Fukuoka et al., 2003; Kris et al., 2003, *JAMA*), the frequency of these mutations in unselected US patients is low (Paez et al., 2004). These observations and the finding that objective response can be detected in patients carrying apparently wild type allele of the EGFR gene (Lynch et al, Pao et al., Han et al (JCO, 23:2493, 2005), Mitsudomi et al., JCO 23:2513, 2005, Kim et al., Clinical Cancer Res, 11:2244, 2005) suggest that other mechanisms are also involved in the response to gefitinib. Furthermore, while these activating mutations identify patients with high response rates, they cannot account for the high stable disease rates, reported to occur in about 30% of NSCLC patients treated with gefitinib (Fukuoka et al., 2003; Kris et al., 2003, *JAMA*).

In summary, there are no reliable selection criteria for determining which cancer patients, including NSCLC patients, will benefit from treatment with EGFR inhibitors exemplified by, but not limited to, gefitinib. Therefore, it is of great interest to identify both patients that would benefit from EGFR inhibitors and patients who are not going to benefit from such therapy, as well as to identify treatments which can improve the responsiveness of cancer cells which are resistant to EGFR inhibitors, and to develop adjuvant treatments that enhance the response.

SUMMARY OF THE INVENTION

One embodiment of the invention relates to a method to select a cancer patient who is predicted to benefit or not benefit from therapeutic administration of an EGFR inhibitor. The method includes the steps of: (a) detecting in a sample of tumor cells from a patient a level of a biomarker selected from the group consisting of: (b) comparing the level of the biomarker in the tumor cell sample to a control level of the biomarker selected from the group consisting of: (i) a control level of the biomarker that has been correlated with sensitivity to the EGFR inhibitor; and (ii) a control level of the biomarker that has been correlated with resistance to the EGFR inhibitor; and (c) selecting the patient as being predicted to benefit from therapeutic administration of the EGFR inhibitor, if the level of the biomarker in the patient's tumor cells is statistically similar to or greater than the control level of the biomarker that has been correlated with sensitivity to the EGFR inhibitor, or if the level of the biomarker in the patient's tumor cells is statistically greater than the level of the biomarker that has been correlated with resistance to the EGFR inhibitor; or (d) selecting the patient as being predicted to not benefit from therapeutic administration of the EGFR inhibitor, if the level of the biomarker in the patient's tumor cells is statistically less than the control level of the biomarker that has been correlated with sensitivity to the EGFR inhibitor, or if the level of the biomarker in the patient's tumor cells is statistically similar to or less than the level of the biomarker that has been correlated with resistance to the EGFR inhibitor. The biomarker is selected from: (i) a level of amplification of the epidermal growth factor receptor (EGFR) gene; (ii) a level of polysomy of the EGFR gene; (iii) a level of amplification of the human tyrosine kinase receptor-type receptor (HER2) gene; and (iv) a level of polysomy of the HER2 gene. The step of detecting can include detecting any one, two, three, or all four of the biomarkers (i)-(iv). Particularly preferred combinations include, but are not limited to: detecting (i) and (ii), and in one embodiment, also detecting (iii) or (iv); detecting (iii) and (iv), and in one embodiment, also detecting (i) or (ii); and detecting (ii) and (iv).

The step of detecting can include, but is not limited to, using a nucleotide probe that hybridizes to the EGFR gene or the HER2 gene, and/or using a nucleotide probe that hybridizes to chromosome 7 centromere sequences or to chromosome 17 centromere sequences. In one aspect, the probe is a chimeric probe (e.g., that hybridizes to the EGFR gene and to chromosome 7 centromere sequences or that hybridizes to the HER2 gene and to chromosome 17 centromere sequences). The step of detecting can include, in one aspect, detecting the number of copies of the EGFR gene or HER2 gene per tumor cell in one or more tumor cells in the sample, and/or detecting EGFR or HER2 gene amplification per tumor cell in one or more tumor cells in the sample. In a preferred embodiment, the step of detecting is performed by fluorescent in situ hybridization (FISH).

In one aspect of this embodiment, the step of comparing comprises comparing the biomarker level in the tumor cells to a control level of the biomarker in one or more control cells that are resistant to the EGFR inhibitor, and/or in one or more control cells that are sensitive to the EGFR inhibitor. In one aspect, the control level of the biomarker that has been correlated with sensitivity and/or resistance to the EGFR inhibitor has been predetermined.

In one aspect of this embodiment, a patient having a tumor sample with 3 or more copies of the EGFR gene in less than about 40% of cells is predicted to be a poor- or non-responder to treatment with the EGFR inhibitor. In another aspect, a patient having a tumor sample with about 4 or more copies of the EGFR gene in greater than or equal to about 40% of cells is predicted to benefit from treatment with the EGFR inhibitor. In another aspect, a patient is predicted to benefit from to treatment with the EGFR inhibitor, when the patient has a tumor sample with EGFR gene clusters or: (a) a ratio of EGFR gene copies to chromosome 7 copies per cell of about 2 or more; or (b) an average of about 15 or more copies of the EGFR gene per cell in greater than or equal to about 10% of analyzed cells. In another aspect, a patient having a tumor sample with 3 or more copies of the HER2 gene in less than about 40% of cells is predicted to be a poor- or non-responder from treatment with the EGFR inhibitor. In yet another aspect, a patient having a tumor sample with about 4 or more copies of the HER2 gene in greater than or equal to about 40% of cells is predicted to benefit from treatment with the EGFR inhibitor. In another aspect, a patient is predicted to benefit from treatment with the EGFR inhibitor, when the patient has a tumor sample with HER2 gene clusters or: (a) a ratio of HER2 gene copies to chromosome 17 copies per cell of about 2 or more; or (b) an average of about 15 or more copies of the HER2 gene per cell in greater than or equal to about 10% of analyzed cells.

In one aspect of this embodiment, selection of the patient in step (d) based on EGFR gene amplification or polysomy is reversed if the patient is selected as being predicted to benefit from therapeutic administration of the EGFR inhibitor based on HER2 gene amplification or polysomy. In another aspect of this embodiment, the selection of the patient in step (c) based on EGFR gene amplification or polysomy and the positive selection of the patient based on HER2 gene amplification or polysomy increases the likelihood that the patient will respond to treatment with the EGFR inhibitor as compared to selection of the patient in step (c) based on EGFR gene amplification or polysomy alone.

In another aspect of this embodiment, the method further includes further steps of: (a) detecting a level of expression of epidermal growth factor receptor (EGFR) protein in the tumor cell sample; (b) comparing the level of EGFR protein expression in the tumor cell sample to a control level of EGFR protein expression selected from the group consisting of: (i) a control level that has been correlated with sensitivity to the EGFR inhibitor; and (ii) a control level that has been correlated with resistance to the EGFR inhibitor; and (c)

selecting the patient as being predicted to benefit from therapeutic administration of the EGFR inhibitor, if the level of EGFR protein expression in the patient's tumor cells is statistically similar to or greater than the control level of EGFR protein expression that has been correlated with sensitivity to the EGFR inhibitor, or if the level of EGFR protein expression in the patient's tumor cells is statistically greater than the level of EGFR protein expression that has been correlated with resistance to the EGFR inhibitor; or (d) selecting the patient as being predicted to not benefit from therapeutic administration of the EGFR inhibitor, if the level of EGFR protein expression in the patient's tumor cells is statistically less than the control level of EGFR protein expression that has been correlated with sensitivity to the EGFR inhibitor, or if the level of EGFR protein expression in the patient's tumor cells is statistically similar to or less than the level of EGFR protein expression that has been correlated with resistance to the EGFR inhibitor. In a preferred embodiment, the level of EGFR protein expression is detected using immunohistochemistry (IHC).

In another aspect of any of the embodiments of the method above, the method also includes the following steps: (a) detecting a level of expression of phosphorylated Akt protein in the tumor cell sample; (b) comparing the level of phosphorylated Akt protein expression in the tumor cell sample to a control level of phosphorylated Akt protein expression selected from the group consisting of: (i) a control level that has been correlated with sensitivity to the EGFR inhibitor; and (ii) a control level that has been correlated with resistance to the EGFR inhibitor; and (c) selecting the patient as being predicted to benefit from therapeutic administration of the EGFR inhibitor, if the level of phosphorylated Akt protein expression in the patient's tumor cells is statistically similar to or greater than the control level of phosphorylated Akt protein expression that has been correlated with sensitivity to the EGFR inhibitor, or if the level of phosphorylated Akt protein expression in the patient's tumor cells is statistically greater than the level of phosphorylated Akt protein expression that has been correlated with resistance to the EGFR inhibitor; or (d) selecting the patient as being predicted to not benefit from therapeutic administration of the EGFR inhibitor, if the level of phosphorylated Akt protein expression in the patient's tumor cells is statistically less than the control level of phosphorylated Akt protein expression that has been correlated with sensitivity to the EGFR inhibitor, or if the level of phosphorylated Akt protein expression in the patient's tumor cells is statistically similar to or less than the level of phosphorylated Akt protein expression that has been correlated with resistance to the EGFR inhibitor. In a preferred embodiment, the level of phosphorylated Akt protein expression is detected using immunohistochemistry (IHC). In one aspect, the method includes the step of detecting comprises detecting EGFR polysomy and expression of phosphorylated AKT protein.

Any of the above-described embodiments of the invention can further include a step of detecting mutations in the EGFR gene, wherein detection of one or more mutations in the EGFR gene is further predictive that the patient will benefit from treatment with the EGFR inhibitor. For example, mutations in any one or more of exons 18, 19 and 21 of the EGFR gene or in the tyrosine kinase domain of the EGFR gene can be detected.

Another embodiment of the present invention relates to a method to select a cancer patient who is predicted to benefit or not benefit from therapeutic administration of an EGFR inhibitor. The method comprises the steps of: (a) detecting in a sample of tumor cells from a patient a level of expression of epidermal growth factor receptor (EGFR) protein; (b) comparing the level of EGFR protein expression in the tumor cell sample to a control level of EGFR protein expression selected from the group consisting of: (i) a control level that has been correlated with sensitivity to the EGFR inhibitor; and (ii) a control level that has been correlated with resistance to the EGFR inhibitor; and (c) selecting the patient as being predicted to benefit from therapeutic administration of the EGFR inhibitor, if the level of EGFR protein expression in the patient's tumor cells is statistically similar to or greater than the control level of EGFR protein expression that has been correlated with sensitivity to the EGFR inhibitor, or if the level of EGFR protein expression in the patient's tumor cells is statistically greater than the level of EGFR protein expression that has been correlated with resistance to the EGFR inhibitor; or (d) selecting the patient as being predicted to not benefit from therapeutic administration of the EGFR inhibitor, if the level of EGFR protein expression in the patient's tumor cells is statistically less than the control level of EGFR protein expression that has been correlated with sensitivity to the EGFR inhibitor, or if the level of EGFR protein expression in the patient's tumor cells is statistically similar to or less than the level of EGFR protein expression that has been correlated with resistance to the EGFR inhibitor. In a preferred embodiment, the level of EGFR protein expression is detected using immunohistochemistry (IHC).

In one aspect of this embodiment, the method further includes a step of detecting mutations in the EGFR gene, wherein detection of one or more mutations in the EGFR gene is further predictive that the patient will respond to treatment with the EGFR inhibitor. For example, mutations in any one or more of exons 18, 19 and 21 of the EGFR gene or mutations in the tyrosine kinase domain of the EGFR gene can be detected.

In another aspect of this embodiment, the method includes further steps of: (a) detecting a level of expression of phosphorylated Akt protein in the tumor cell sample; (b) comparing the level of phosphorylated Akt protein expression in the tumor cell sample to a control level of phosphorylated Akt protein expression selected from the group consisting of: (i) a control level that has been correlated with sensitivity to the EGFR inhibitor; and (ii) a control level that has been correlated with resistance to the EGFR inhibitor; and (c) selecting the patient as being predicted to benefit from therapeutic administration of the EGFR inhibitor, if the level of phosphorylated Akt protein expression in the patient's tumor cells is statistically similar to or greater than the control level of phosphorylated Akt protein expression that has been correlated with sensitivity to the EGFR inhibitor, or if the level of phosphorylated Akt protein expression in the patient's tumor cells is statistically greater than the level of phosphorylated Akt protein expression that has been correlated with resistance to the EGFR inhibitor; or (d) selecting the patient as being predicted to not benefit from therapeutic administration of the EGFR inhibitor, if the level of phosphorylated Akt protein expression in the patient's tumor cells is statistically less than the control level of phosphorylated Akt protein expression that has been correlated with sensitivity to the EGFR inhibitor, or if the level of phosphorylated Akt protein expression in the patient's tumor cells is statistically similar to or less than the level of phosphorylated Akt protein expression that has been correlated with resistance to the EGFR inhibitor.

The method in any of the embodiments of the invention described above can be used with a patient having any type of cancer. In one preferred embodiment, the patient has lung cancer, including, but not limited to, non-small cell lung carcinoma (NSCLC), bronchioloalveolar carcinoma (BAC), or adenocarcinomas with BAC features.

In any of the embodiments of the invention described above, responsiveness to any EGFR inhibitor can be evaluated, including, but not limited to, gefitinib, eroltinib, and cetuximab.

Yet another embodiment of the invention relates to an assay kit for selecting a cancer patient who is predicted to benefit or not to benefit from therapeutic administration of an EGFR inhibitor. The assay kit includes: (a) a means for detecting in a sample of tumor cells a level of a biomarker or a combination of biomarkers selected from: (i) a level of amplification of the epidermal growth factor receptor (EGFR) gene; (ii) a level of polysomy of the EGFR gene; (iii) a level of amplification of the human tyrosine kinase receptor-type receptor (HER2) gene; (iv) a level of polysomy of the HER2 gene; (v) a level of EGFR protein expression; and/or (vi) a level of phosphorylated Akt protein expression. The kit also includes: (b) a control selected from: (i) a control sample for detecting sensitivity to the EGFR inhibitor; (ii) a control sample for detecting resistance to the EGFR inhibitor; (iii) information containing a predetermined control level of the biomarker that has been correlated with sensitivity to the EGFR inhibitor; and/or (iv) information containing a predetermined control level of the biomarker that has been correlated with resistance to the EGFR inhibitor. In one aspect, the kit can further include at least one means for detecting at least one mutation in the EGFR gene.

In one aspect of this embodiment, the means for detecting in any of (a)(i)-(a)(iv) comprises a nucleotide probe that hybridizes to a portion of the gene, including but not limited to: a nucleotide probe that hybridizes to a portion of human chromosome 7 or human chromosome 17; a nucleotide probe that hybridizes to a portion of an EGFR gene and to a portion of the chromosome 7 other than the EGFR gene; and a nucleotide probe that hybridizes to a portion of an HER2 gene and to a portion of the chromosome 17 other than the HER2 gene. In a preferred embodiment, the means for detecting is for use in fluorescent in situ hybridization (FISH). In another aspect of this embodiment, the means for detecting in (a)(v) or (a)(vi) comprises an antibody or antigen binding fragment thereof that selectively binds to the protein. Preferably, any of the above-described means for detecting comprises a detectable label and/or is immobilized on a substrate.

BRIEF DESCRIPTION OF THE FIGURES OF THE INVENTION

FIGS. 2A and 2B show Kaplan Meyers curves for time to disease progression (A) and survival (B) in FISH Groups 1 and 2 in Example 1.

DETAILED DESCRIPTION OF THE INVENTION

Figure 1B:
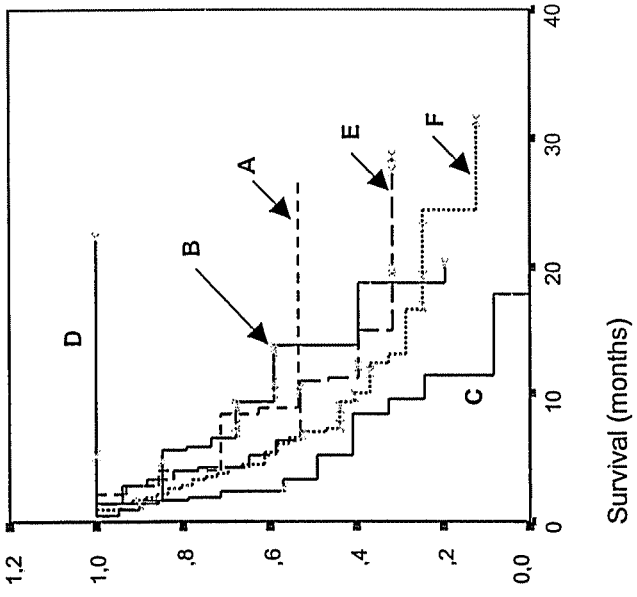
FIGS. 1A and 1B show Kaplan Meyers curves for time to disease progression (A) and survival (B) in the six FISH categories: Disomy, Low Trisomy, High Trisomy, Low Polysomy, High Polysomy and Gene Amplification in Example 1.

Based on promising results from clinical Phase II studies, gefitinib was approved by the US Food and Drug Administration for treatment of advanced chemorefractory NSCLC in 2003, and erlotinib in 2004 after it demonstrated a significant survival benefit compared to placebo in pre-treated NSCLC patients (Shepherd et al., 2004). The clinical efficacy of these EGFR tyrosine kinase inhibitors (EGFR-TKIs) is significant but unfortunately is limited to a subgroup of the patients. In the Canadian BR-21 study (erlotinib versus placebo), about 30% of the patients died within 3 months after the treatment start, which indicated that no clinical benefit was achieved in this subgroup of patients. Clinically, patients who benefit are more likely to have female gender, adenocarcinoma histology and a never-smoking history (Fukuoka et al., 2003; Kris et al., 2003, *JAMA*; Miller et al., 2004, *J. Clin. Oncol.*). However, clinical features alone are not sufficient for patient selection because patients lacking individual features may still benefit. These observations have left a need to provide biologic features that could predict for patient benefit in NSCLC and other cancers associated with EGFR expression. The present invention provides powerful biomarkers and protocols that address this problem.

The present invention is generally related to the identification of cancer patients that are predicted to benefit from the therapeutic administration of an epidermal growth factor receptor (EGFR) inhibitor. The present invention is also generally related to methods to identify treatments that can improve the responsiveness of EGFR inhibitor-resistant cancer cells to the treatment, and to the development of adjuvant treatments that enhance the EGFR inhibitor response.

Accordingly, one embodiment of the present invention relates to a method and corresponding assay kit for use to select a cancer patient who is predicted to benefit from therapeutic administration of an epidermal growth factor receptor (EGFR) inhibitor, an agonist thereof, or a drug having substantially similar biological activity as the reference EGFR inhibitor. The method generally includes detecting in a sample of tumor cells from a patient the biomarkers related to EGFR and combinations thereof that have been discovered by the inventors to be invaluable in the detection of EGFR inhibitor-sensitive or resistant tumor cells, thus predicting the patients' clinical benefit to treatment using the EGFR inhibitor. Based on the inventors' discovery, a variety of tests and combinations of biomarker detection strategies are proposed, and will be discussed in detail below. Initially, however, the present invention includes the use of the following strategies for detection of biomarkers, alone or in various combinations: (1) detection of the level of amplification of the epidermal growth factor receptor (EGFR) gene (i.e., the gene encoding EGFR); (2) detection of a level of polysomy of the epidermal growth factor receptor (EGFR) gene; (3) detection of a level of gene amplification of the HER2 gene; (4) detection of the level of polysomy of the HER2 gene; (5) detection of mutations in the EGFR gene; (6) detection of EGFR protein expression; and (7) detection of phosphorylated Akt expression. The invention includes the use of these detection protocols individually or in various combinations, and the invention further includes the use of various combinations of one or more biomarker detection techniques to further enhance the ability of the present method to identify EGFR inhibitor-sensitive and -resistant tumors, as well as to predict patients' clinical benefit (e.g, response and outcome) to EGFR inhibitors.

The inventors have also discovered that combinations of the tests described herein can be used to select patients with cancer, including NSCLC, who will not have clinical benefit from EGFR inhibitors (e.g. patients with tumors that are negative for two or more tests).

The present inventors have discovered that patients with tumor cells displaying EGFR gene amplification and/or high polysomy with respect to the EGFR gene (also generally referred to herein as an increase in EGFR gene copy number or a gain in EGFR copy number), and/or HER2 gene amplification and/or high polysomy (also generally referred to herein as an increase in HER2 gene copy number or a gain in HER2 copy number) with respect to the HER2 gene, are predicted to be especially responsive to treatment with EGFR inhibitors, and are therefore the best candidates for the use of this line of therapy. In contrast, patients having tumors with little or no gain in copy number of the EGFR and/or HER2 genes are predicted to have a poor outcome to treatment with EGFR inhibitors.

Interestingly, the present inventors have also discovered that for patients that are EGFR negative (i.e., not predicted to respond to EGFR inhibitors based on EGFR results alone), if such patients' tumors have HER2 gene amplification and/or polysomy (e.g., high trisomy or low or high polysomy) of the HER2 gene, the patient outcome is better as compared to patients without HER2 gene amplification. Furthermore, for patients that are predicted to respond to EGFR inhibitors based on EGFR results alone, HER2 gene amplification and/or high polysomy in these patients' tumors is predictive of even greater sensitivity to the EGFR inhibitor treatment than in the absence of the HER2 gene amplification.

The inventors have also found that EGFR protein expression can be used to predict patient outcome with EGFR inhibitor treatment, in contrast to prior studies that detected no correlation between EGFR protein expression and response to therapy. Specifically, the present inventors have used assessment criteria that accounts for both expression intensity and the fraction of expression-positive cells in a sample, and have now demonstrated that patients having tumor cells in the upper 50% of the scoring protocol (i.e., denoted positive/high EGFR expressors) had much better outcomes (e.g., better response times, slower progression rates and longer survival times) when treated with EGFR inhibitors than those in the lower expressing groups. Furthermore, the inventors have demonstrated that the combination of detection of EGFR protein expression with HER2 or EGFR gene amplification or polysomy is significantly more predictive of patient outcome to EGFR inhibitor treatment than the detection of one or no markers.

The inventors have also found that a group of cancer patients with low/no gain of EGFR gene (e.g., "FISH-negative") and low/no expression of EGFR protein (e.g., "IHC-negative"), which constitute about 30% of the total NSCLC population, seem not to have any clinical benefit (no/very low response rate, short time to progression and short survival time) from EGFR inhibitors.

The inventors have also shown that two other biomarkers, namely mutated EGFR genes or phosphorylated Akt expression, can be combined with any of these biomarkers and protocols discussed above to improve the ability to detect patients predicted to respond to EGFR inhibitor treatment. For example, the inventors demonstrate herein that the combination of detection of mutations in the EGFR gene with EGFR protein expression, EGFR gene amplification and/or polysomy, and/or HER2 gene amplification and/or polysomy, can be used to select patients who will have clinical benefit from EGFR inhibitor therapy. The inventors have also demonstrated herein that the combination of the detection of phosphorylated Akt (i.e., activated Akt) with detection of EGFR protein expression and/or detection of EGFR gene amplification and/or polysomy can be used to select patients who will have clinical benefit from EGFR inhibitor therapy.

The present inventors also demonstrate herein the power of using particular detection techniques, fluorescence in situ hybridization (FISH) and immunohistochemistry (IHC) in the present methods, although the methods of the invention are not limited to the use of these techniques.

Finally, although many of the examples provided herein are directed to the EGFR inhibitor, gefitinib, the methods of the present invention are not limited to the prediction of patients that will respond or not respond to this particular EGFR inhibitor, but rather, can be used to predict patient's outcome to any EGFR inhibitor, including inhibitors that are small molecules (drugs), peptides, antibodies, nucleic acids, or other types of inhibitors. For example, the present inventors have also demonstrated the use of the present methods to predict tumor resistance or susceptibility to the EGFR inhibitor, Cetuximab (Erbitux®), which is a monoclonal antibody that binds to EGFR and prevents the binding of the natural ligand to the receptor.

More specifically, the present inventors have demonstrated that EGFR gene copy number (determined by polysomy and/or gene amplification) detected by FISH and EGFR protein expression by IHC significantly correlated with gefitinib activity, and those patients carrying EGFR gene amplification and/or polysomy (particularly high polysomy) and/or high EGFR protein expression had a significant improvement in response, time to progression and survival. The inventors have also demonstrated that HER2 gene amplification and/or polysomy (particularly high polysomy) provides similar effects. The strongest benefit was observed in patients with gene amplification, with the combination of EGFR gene amplification and HER2 gene amplification being particularly strong. Multivariate analysis confirmed that EGFR gene amplification and polysomy (particularly high polysomy) and EGFR protein expression significantly reduced the risk of death in patients receiving gefitinib. Among clinical characteristics (gender, smoking history, performance status and histology), only histology and PS resulted significantly related to the risk of death when the model was adjusted for EGFR status. Risk of death was significantly lower for patients with adenocarcinoma or bronchioloalveolar carcinoma and significantly higher for those with performance status 2.

Prior to the present invention, the prognostic role of EGFR protein expression or gene status in NSCLC has been unclear at best, as there have been varying reports in the literature. The inventors have studied the prognostic role of EGFR protein expression and gene copy number and found that EGFR protein expression correlated with increased gene copy number, and that high gene copy number per cell showed a trend towards poor prognosis (Hirsch et al., 2003 JCO). Likewise, the inventors studied HER2 gene copy number and protein expression in 238 patients with NSCLC and found that high HER2 protein expression showed a tendency toward a shorter survival (Hirsch et al, BJC, 2002).

However, the levels of EGFR protein expression evaluated by immunohistochemical assays have not previously been demonstrated to correlate with response to therapy in pre-clinical (Sirotnak et al., Clin Cancer Res 2000; 6:4885-92) and clinical studies (Kris et al., 2003, JAMA; Giaccone et al., 2004). Gefitinib exerts its action at the protein level, therefore it was not at all expected that the number of copies of the EGFR gene per cell could be a predictor for clinical response, given the lack of correlation with the immunohistochemical studies.

In the study illustrated in Example 1, a better outcome was observed in the cohort with amplification or high polysomy for the EGFR gene, therefore confirming the positive impact of the drug in this group of patients. Moreover, the 1-year survival of patients in FISH positive patients (Group 2 in Example 1 below) was remarkably higher in the present inventors' study than reported on the previous phase II trials with gefitinib.

A major drawback for the gefitinib clinical studies has been the lack of correlation between level of EGFR protein expression and response to treatment. Other studies focusing on HER2 and response to trastuzumab in breast cancer confirmed that genomic analyses correlate better with response than protein expression scored as 2+ in the HerceptTest (Vogel et al., 2002; Bartlett et al., 2003). The identification of specific EGFR gene mutations in gefitinib sensitive patients confirmed the validity of analyses at genomic level (Lynch et al., 2004; Paez et al., 2004). However, these studies involved technology for analysis completely different from what is proposed in the present invention.

In the studies presented herein, EGFR and HER2 gene copy numbers were studied by FISH because this method presents several advantages, although the practice of the present invention is not limited to this technique. FISH is DNA-based and can be successfully performed in fresh or preserved paraffin-embedded tumor samples. The technology is well established, has short turn-around in clinical cytogenetics and molecular pathology laboratories, and an EGFR FISH probe is already commercially available. Moreover, for patients with advanced disease, and especially for those progressing after standard therapies, disease stabilization and symptomatic improvement are important endpoints, and gefitinib reaches this goal in about 40% of cases (Fukuoka et al., 2003; Kris et al., 2003, JAMA). The results demonstrated that patients with EGFR gene amplification and high polysomy had significant advantages not only on response, but also on disease control rate. These findings, combined with the simplicity of the assay and the reproducibility of the result, support the routine use of EGFR-FISH analysis and related techniques for selecting NSCLC patients to gefitinib therapy.

The clinical characteristics of the population evaluated in the study described in Examples 1 and 3 reflect what is generally observed in Italy in the clinical practice, and the outcome of this cohort is in the same range of the IDEAL 1 and 2 trials (Fukuoka et al., 2003; Kris et al., 2003, JAMA). The EGFR gene status has only been scarcely studied in lung cancer. In the current study, 12.7% of tumors had gene amplification and 19.7% had high level of polysomy. Gene amplification has been reported in 6.2% of 286 specimens using Southern Blot analysis (Reissmann et al., 1999), while polysomy and amplification have been respectively observed in 13% and 9% of 183 NSCLC investigated in a tumor microarray (Hirsch et al., 2003 JCO). Other population studies will verify if this variability represents the actual heterogeneity in the NSCLC patients.

Levels of protein expression of EGFR were also assessed by immunohistochemistry and high levels were statistically significantly associated with better response, disease control rate, time to progression and survival as described below in the Examples. In the studies presented herein, gefitinib sensitivity was associated with high EGFR protein expression; outcomes in patients with low EGFR expression scores (<200) were as poor as those in patients with low gene copy numbers or lacking mutations. The reasons for the difference in results from this invention compared to previous reports might be multiple. For example, the present inventors have used a different scoring system than prior investigators, taking both the fraction of EGFR expressing cells (0-100%) and the expression intensity (1-4) into account, which may have improved the inventors' ability to detect and analyze differences in expression. However, the application of this invention is not restricted to this scoring criteria, and other assessment methods may be useful in the practice of the invention. Immunohistochemical analysis for EGFR protein expression is an easy clinically applicable assay and the antibody used in this invention is based on commercially available antibody (Zymed; see Examples). However, the application of this invention is not restricted to a specific antibody.

Another important finding of the studies described herein was the virtual absence of EGFR mutations in patients with stable disease. Among the 21 patients with stable disease who were assessed for EGFR mutations, only one patient had an EGFR mutation. The small number of mutations in patients with stable disease is of clinical relevance because data from one clinical trial showed that the survival benefit of gefitinib is not confined to responding patients (Shepherd et al., 2004). It is possible that survival improvement in the gefitinib-treated patients, as a whole, is due to the presence of a group of patients with an intermediate benefit from the treatment, such as those with stable disease, who would be excluded from tyrosine kinase inhibitor treatment if mutation analysis were established as the test of choice for patient selection. Moreover, although previous studies suggested that EGFR mutations are present in the vast majority of responding patients (Lynch et al., 2004; Paez et al., 2004; Pao et al., 2004), in this study, the inventors observed that 40% of patients with EGFR mutations had progressive disease.

In the studies presented herein, the inventors also found an association between activated Akt pathway (e.g. expression of phosphorylated Akt) and gefitinib sensitivity, an association that has also been described and discussed by others (Sordella et al., 2004; Cappuzzo et al., 2004, J. Natl Cancer Inst.). The combinatorial analysis of EGFR and P-Akt status indicated that, independent of the method of EGFR assessment, when EGFR status was positive, the presence of Akt phosphorylation was significantly related to better response, disease control rate, time to progression, and survival. Importantly, better outcome was observed not only when the subset of EGFR+/P-Akt+ patients was compared with all the other groups combined but also when this subset was compared with patients EGFR positive but P-Akt negative. These findings support the hypothesis that, when the gefitinib target is present but the anti-apoptotic pathway is not activated, the patient is not sensitive to the inhibitory effects of gefitinib. As expected, the EGFR+/P-Akt+ group also had a significantly better outcome compared with the EGFR negative and P-Akt positive group, confirming preclinical data indicating that aberrant, EGFR-independent Akt activation may lead to gefitinib resistance (Bianco et al., 2003; Janmaat et al., 2003). These data indicate that P-Akt positive status is relevant in EGFR-positive patients for the identification of a subgroup of patients particularly sensitive to the drug. In EGFR-negative patients, P-Akt positive status may identify a group of patients with a very low chance of benefiting from gefitinib treatment.

Information regarding the relationship between EGFR protein expression and Akt pathway activation would greatly advance the understanding of the mechanisms of gefitinib sensitivity. The inventors compared EGFR protein and P-Akt expression in a subgroup of patients and, in general, the inventors found expression of EGFR and P-Akt proteins in the same cell populations (data not shown), suggesting that the observed P-Akt was a result of EGFR activity.

The methods and test kits provided by the present invention are extremely useful for patients with any cancer that can be treated with EGFR inhibitors, such as NSCLC. Such patients might, as a result of the methods provided herein, be spared from side effects and financial costs of an ineffective therapy in the event that they do not have genomic gain affecting the EGFR locus and they have low or no EGFR protein expression. Second, it is useful for physicians, who can recommend, or not, this specific treatment (i.e., EGFR inhibitor therapy) to particular patients based on information on the molecular characteristics of their tumors. Third, it will increase the demand for the FISH assay with available and yet-to-be developed EGFR probes.

More specific embodiments of the invention are described as follows. In one embodiment, the method includes the detection in a sample of tumor cells from a patient a level of amplification (described in detail below) of the epidermal growth factor receptor (EGFR) gene (i.e., the gene encoding EGFR). Patients with tumor cells displaying EGFR gene amplification are predicted to be responsive to treatment with EGFR inhibitors, and are therefore the best candidates for the use of this line of therapy. In contrast, patients having tumors with little or no EGFR gene amplification gain are predicted to be poor or non-responders to treatment with EGFR inhibitors and therefore, different therapeutic treatments can be used with such patients. In another, related embodiment, the method includes the detection in a sample of tumor cells from a patient a level of polysomy (described in detail below) of the epidermal growth factor receptor (EGFR) gene. In this embodiment, patients with tumor cells displaying higher polysomy with respect to the EGFR gene are predicted to be responsive to treatment with EGFR inhibitors, and are therefore the best candidates for the use of this line of therapy. In contrast, patients having tumors with low copy numbers with respect to the EGFR gene are predicted to be poor or non-responders to treatment with EGFR inhibitors. In one embodiment, this method of detecting polysomy can be combined with the detection of EGFR gene amplification in the tumor cells. Collectively, gene amplification and polysomy can be referred to as a gain in EGFR gene copy number or increased EGFR gene copy number. In addition, the present inventors demonstrate herein that increased EGFR gene copy number detected by FISH is associated with improved survival after gefitinib therapy in patients with advanced stage bronchioalveolar carcinoma (BAC) and adenocarcinoma with BAC features, a subset of NSCLC that can serve as a model for study of EGFR pathways due to its underlying biologic characteristics.

In another embodiment of the invention, the method includes the detection in a sample of tumor cells from a patient a level of gene amplification of the HER2 gene (i.e., the gene encoding HER2). Patients with tumor cells displaying HER2 gene amplification are predicted to be responsive to treatment with EGFR inhibitors, and are therefore the best candidates for the use of this line of therapy. In contrast, patients having tumors with low or no HER2 gene amplification are predicted to be poor or non-responders to treatment with EGFR inhibitors and therefore, different therapeutic treatments can be used with such patients. In another embodiment, the method includes the detection in a sample of tumor cells from a patient a level of polysomy of the HER2 gene. In this embodiment, patients with tumor cells displaying higher polysomy with respect to the HER2 gene are predicted to be responsive to treatment with EGFR inhibitors, and are therefore the best candidates for the use of this line of therapy. In contrast, patients having tumors with low copy numbers with respect to the HER2 gene are predicted to be poor or non-responders to treatment with EGFR inhibitors. In one embodiment, this method of detecting polysomy can be combined with the detection of HER2 gene amplification in the tumor cells. Collectively, gene amplification and polysomy can be referred to as a gain in HER2 gene copy number or increased HER2 gene copy number. These methods can also be combined with the detection of EGFR gene amplification and/or EGFR polysomy. Patients having tumors displaying both an increase in EGFR gene copy numbers and an increase in HER2 gene copy numbers are predicted to be even better candidates for responsiveness to treatment with EGFR inhibitors than patients with tumors displaying increases in EGFR gene copy numbers alone. Moreover, patients having tumors displaying low or no gain in EGFR gene copy numbers but having increases in HER2 gene copy numbers are predicted to be better responders to treatment with EGFR inhibitors than patients having tumors with low or no gain in HER2 gene copy numbers.

In another embodiment of the invention, the method includes the detection in a sample of tumor cells from a patient a level of EGFR protein expression (e.g., by using immunohistochemical techniques). Patients with tumor cells displaying higher levels of EGFR protein are predicted to be responsive to treatment with EGFR inhibitors, and are therefore the best candidates for the use of this line of therapy. In particular, patients with tumor cells having both a higher fraction of cells expressing EGFR and a higher intensity of expression of EGFR by the cells are predicted to be responsive to treatment with EGFR inhibitors. In one embodiment using a scoring system of 0-400 based on fraction and intensity scores (described in detail below), patients with tumor cells receiving EGFR protein expression scores of greater than 200 are predicted to have a good outcome of treatment with EGFR inhibitors. In further embodiments, this method can be combined with the detection of HER2 gene amplification and/or polysomy; detection of EGFR gene amplification and/or polysomy; detection of mutations in EGFR (described below) and/or detection of phosphorylated Akt protein levels (described below). Patients having tumors with high EGFR protein expression in combination with: HER2 gene amplification and/or HER2 polysomy, with EGFR gene amplification and/or EGFR polysomy, mutations in the EGFR gene, and/or phosphorylated Akt expression, are predicted to be responsive to treatment with EGFR inhibitors.

In one embodiment of the invention, the method includes detection mutations in the EGFR gene in a sample of tumor cells from a patient. Patients with tumor cells displaying mutations in the EGFR gene are predicted to be responsive to treatment with EGFR inhibitors, and are therefore the best candidates for the use of this line of therapy. Activating mutations cause ligand-independent activity of receptor tyrosine kinases, and recent reports show that specific missense and deletion mutations in the tyrosine kinase domain of the EGFR gene (Lynch et al., 2004; Paez et al., 2004; Pao et al., 2004) are associated with EGFR tyrosine kinase inhibitor sensitivity, and also with female gender, adenocarcinoma histology, and never smoking status, all clinical characteristics that are known to be related to tyrosine kinase inhibitor sensitivity (Fukuoka et al., 2003; Kris et al., 2003, *JAMA*; Perez-Soler et al., 2001; Miller et al., 2003, *Proc. Am Soc Clin Oncol.*; Miller et al., 2004, *J. Clin. Oncol.*). Although these EGFR mutations can account for the vast majority of objective responses obtained with tyrosine kinase inhibitors, the clinical benefit observed with these drugs and the survival benefit identified in the a prior clinical trial cannot be explained only by the presence of mutations.

While any EGFR mutations may be detected, multiple mutations are already known to occur in humans, particularly on exons 18, 19 and 21. As discussed above, this method can be combined with the detection of EGFR protein expression; detection of EGFR gene amplification and/or polysomy; detection of HER2 gene amplification and/or polysomy; and/or detection of phosphorylated Akt protein levels (described below). Patients having tumors with one or more mutations in the EGFR gene in combination with: high EGFR protein expression, HER2 gene amplification and/or HER2 polysomy, EGFR gene amplification and/or EGFR polysomy, and/or phosphorylated Akt expression, are predicted to be responsive to treatment with EGFR inhibitors.

In another embodiment of the invention, the method includes detection in a sample of tumor cells from a patient phosphorylated Akt protein levels. The activation status of the Akt protein has been highlighted as an important player in EGFR tyrosine kinase inhibitor sensitivity in preclinical and clinical studies (Sordella et al., 2004; Cappuzzo et al., 2004, *J. Natl. Cancer Inst.*). Akt is a serine/threonine kinase that acts downstream of EGFR to regulate many cellular processes, including cell survival, proliferation, and growth, and it is activated by phosphorylation at amino acids Thr308 and Ser473 (Datta et al., 1999). Sordella et al., supra, showed that gefitinib-sensitizing EGFR mutations activate anti-apoptotic pathways involving Akt in lung cancer cell lines, and Cappuzzo et al., supra, have shown that the activation status of Akt is associated with gefitinib sensitivity of NSCLC patients, in terms of response and time to progression, but not in terms of survival. The lack of association with survival could be explained by the presence of a subset of phosphorylated (P)-Akt-positive patients who are resistant to gefitinib therapy as a consequence of Akt activation by a non-EGFR dependent mechanism.

Patients with tumor cells expressing phosphorylated Akt protein are predicted to be responsive to treatment with EGFR inhibitors, and are therefore the best candidates for the use of this line of therapy. As discussed above, this method is intended to be combined with any one or more of: the detection of EGFR protein expression; detection of EGFR gene amplification and/or polysomy; detection of HER2 gene amplification and/or polysomy; and/or detection of mutations in the EGFR gene, in order to enhance the ability to identify patients having tumors that are predicted to respond to EGFR inhibitor therapy. Patients having tumors that express phosphorylated Akt in combination with: one or more mutations in the EGFR gene, high EGFR protein expression, HER2 gene amplification and/or HER2 polysomy, and/or EGFR gene amplification and/or EGFR polysomy, are predicted to be responsive to treatment with EGFR inhibitors.

In one embodiment of the invention, the method includes the detection of EGFR and HER2 gene amplification and/or polysomy using fluorescent in situ hybridization (FISH).

In one embodiment of the invention, the method includes the detection of EGFR protein or phosphorylated Akt protein using immunohistochemistry (IHC) techniques.

It will be apparent to those of skill in the art from the description of the invention herein that a variety of combinations of the above-described biomarkers and detection protocols can enhance or improve the ability to identify patients that are predicted to be responsive to therapy with EGFR inhibitors (and patients that are predicted to be poor responders). Therefore, any combination of the use of the biomarkers, detection protocols and detection techniques is encompassed by the invention. Moreover, the invention is not limited to the detection techniques described herein (e.g., FISH and IHC), since other techniques may be used to achieve the same result. By way of example, the following particular combinations have been demonstrated by the inventors to be particularly useful in predicting responsiveness to EGFR inhibitors: (1) combination of detection of EGFR gene amplification and/or polysomy using FISH and detection of HER2 gene amplification and/or polysomy using FISH; (2) combination of detection of EGFR protein expression using IHC and detection of HER2 gene amplification and/or polysomy using FISH; (3) combination of detection of mutations in the EGFR gene and detection of HER2 gene amplification and/or polysomy using FISH; (4) combination of detection of EGFR gene amplification and/or polysomy using FISH and detection of EGFR protein expression using IHC; (5) combination of detection of EGFR protein expression using IHC and detection of mutations in the EGFR gene; (6) combination of detection of EGFR protein expression and detection of phosphorylated Akt protein using IHC; (7) detection of EGFR gene amplification and/or polysomy and detection of mutations in the EGFR gene; (8) detection of EGFR gene amplification and/or polysomy, detection of EGFR protein expression using IHC, and detection of mutations in the EGFR gene; and (9) detection of EGFR gene amplification and/or polysomy, detection of EGFR protein expression using IHC, and detection of phosphorylated Akt protein expression using IHC.

The methods of the present invention can be used to effectively predict the responsiveness of patient tumors and clinical outcome to treatment with any EGFR inhibitor. Although most of the data provided herein was generated in patients receiving the well-known EGFR inhibitor, gefitinib (ZD 1839, Iressa®, AstraZeneca, UK), it is to be understood that the evaluation of patient tumor responsiveness to any EGFR inhibitor of any type is encompassed by the present invention.

According to the present invention, an EGFR inhibitor is any agent that inhibits (blocks, reduces, antagonizes, decreases, reverses) the expression and/or biological activity of an epidermal growth factor receptor (EGFR), including any EGFR. Therefore, an inhibitor can include, but is not limited to, a product of drug/compound/peptide design or selection, an antibody or antigen binding fragment thereof, a protein, a peptide, a nucleic acid (including ribozymes, antisense, RNAi and aptamers), or any other agent that inhibits the expression and/or biological activity of an EGFR. For example, known inhibitors of EGFR include the drugs, gefitinib (ZD 1839, Iressa®, AstraZeneca, UK) and erlotinib (OSI 774, Tarceva®, Genentech, USA), and the monoclonal antibody, Cetuximab (Erbitux®, Imclone, Bristol-Myers Squibb). However, the invention is not limited to these specific agents, and can include an agonist (described below) of such agents or agents having substantially similar biological activity as these agents. The biological activity or biological action of a protein, such as an EGFR, refers to any function(s) exhibited or performed by a naturally occurring form of the protein as measured or observed in vivo (i.e., in the natural physiological environment of the protein) or in vitro (i.e., under laboratory conditions). Biological activities of EGFR include, but are not limited to, binding to EGF, receptor homo- or heterodimerization, tyrosine kinase activity, and downstream activities related to cellular homeostasis and development.

Various definitions and aspects of the invention will be described below, but the invention is not limited to any specific embodiments that may be used for illustrative or exemplary purposes. To the extent that gefitinib is described herein, it is an exemplary EGFR inhibitor and, as discussed above, the methods of the invention are applicable to evaluation of patient tumor sensitivity or resistance to any EGFR inhibitor.

The methods of the present invention include detecting in a sample of tumor cells from a patient to be tested, any one or any combination of 2, 3, 4, 5, 6 or all 7 of the following biomarkers and types of detection of such biomarkers: (1) a level of amplification of the epidermal growth factor receptor (EGFR) gene (i.e., the gene encoding EGFR); (2) a level of polysomy of the epidermal growth factor receptor (EGFR) gene; (3) a level of gene amplification of the HER2 gene; (4) a level of polysomy of the HER2 gene; (5) mutations in the EGFR gene; (6) EGFR protein expression; and/or (7) phosphorylated Akt expression. Detection of (1) and (2) together and/or detection of (3) and (4) together can generally be referred to as detecting a gain or an increase in gene copy number. According to the present invention, a biomarker includes any gene or protein or portion thereof that can be detected, measured or otherwise evaluated and is used to identify, measure or predict a particular effect, which in the present invention is patient tumor responsiveness (or non-responsiveness) to an EGFR inhibitor. Biomarkers useful in the present invention include EGFR gene, EGFR protein, HER2 gene and phosphorylated Akt protein. The use of a biomarker according to the invention can include the use of a particular protocol or technique to detect or measure the biomarker (types of detection, e.g., FISH or IHC) or the identification of a particular characteristic associated with the biomarker, such as gene amplification, gene polysomy, expression level of the gene or protein, identification of a mutation, etc. Particularly preferred combinations include combinations of the following biomarkers and types of detection thereof as described above: (1) and (2); (3) and (4); (1), (2), (3) and (4); (2) and (4); (1) and/or (2) and (6); (1) and/or (2) and (7); and (6) and (7). The invention is not limited to these combinations.

Suitable methods of obtaining a patient sample are known to a person of skill in the art. A patient sample can include any bodily fluid or tissue from a patient that may contain tumor cells or proteins of tumor cells. More specifically, according to the present invention, the term "test sample" or "patient sample" can be used generally to refer to a sample of any type which contains cells or products that have been secreted from cells to be evaluated by the present method, including but not limited to, a sample of isolated cells, a tissue sample and/or a bodily fluid sample. Most typically in the present invention, the sample is a tissue sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention. The cells in the cell sample are not necessarily of the same type, although purification methods can be used to enrich for the type of cells that are preferably evaluated. Cells can be obtained, for example, by scraping of a tissue, processing of a tissue sample to release individual cells, or isolation from a bodily fluid.

A tissue sample, although similar to a sample of isolated cells, is defined herein as a section of an organ or tissue of the body which typically includes several cell types and/or cytoskeletal structure which holds the cells together. One of skill in the art will appreciate that the term "tissue sample" may be used, in some instances, interchangeably with a "cell sample", although it is preferably used to designate a more complex structure than a cell sample. A tissue sample can be obtained by a biopsy, for example, including by cutting, slicing, or a punch.

A bodily fluid sample, like the tissue sample, contains the cells to be evaluated, and is a fluid obtained by any method suitable for the particular bodily fluid to be sampled. Bodily fluids suitable for sampling include, but are not limited to, blood, mucous, seminal fluid, saliva, sputum, bronchial lavage, breast milk, bile and urine.

In general, the sample type (i.e., cell, tissue or bodily fluid) is selected based on the accessibility and structure of the organ or tissue to be evaluated for tumor cell growth and/or on what type of cancer is to be evaluated. For example, if the organ/tissue to be evaluated is the breast, the sample can be a sample of epithelial cells from a biopsy (i.e., a cell sample) or a breast tissue sample from a biopsy (a tissue sample). The present invention is particularly useful for evaluating patients with lung cancer and particularly, non-small cell lung carcinoma, and in this case, a typical sample is a section of a lung tumor from the patient.

The copy number of genes in tumor cells according to the invention can be measured, for example in FISH assays, in nuclei, and the protein expression can be measured, for example in immunohistochemistry assays, in tumor cell nuclei, cytoplasm and/or membranes. Both tests, e.g., FISH and immunohistochemistry, as well as other detection methods, can be performed in primary tumors, metastatic tumors, locally recurring tumors, sputum, bronchial lavage, ascites, spinal fluid, or other tumoral settings. The markers can be measured in tumor specimens that are fresh, frozen, fixed or otherwise preserved.

Once a sample is obtained from the patient, the sample is evaluated for detection of one or more of any of the biomarkers described herein. In some embodiments of the present invention, a tissue, a cell or a portion thereof (e.g., a section of tissue, a component of a cell such as nucleic acids, etc.) is contacted with one or more nucleic acids. Such protocols are used to detect gene expression, gene amplification, and/or gene polysomy, for example. Such methods can include cell-based assays or non-cell-based assays. The tissue or cell expressing a target gene is typically contacted with a detection agent (e.g., a probe, primer, or other detectable marker), by any suitable method, such as by mixing, hybridizing, or combining in a manner that allows detection of the target gene by a suitable technique.

The patient sample is prepared by any suitable method for the detection technique utilized. In one embodiment, the patient sample can be used fresh, frozen, fixed or otherwise preserved. For example, the patient tumor cells can be prepared by immobilizing patient tissue in, for example, paraffin. The immobilized tissue can be sectioned and then contacted with a probe for detection of hybridization of the probe to a target gene (e.g., EGFR or HER2).

In a preferred embodiment, detection of a gene according to the present invention is accomplished using hybridization assays. Nucleic acid hybridization simply involves contacting a probe (e.g., an oligonucleotide or larger polynucleotide) and target nucleic acid under conditions where the probe and its complementary target can form stable hybrid duplexes through complementary base pairing. As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety. Nucleic acids that do not form hybrid duplexes are washed away from the hybridized nucleic acids and the hybridized nucleic acids can then be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA: DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

High stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). One of skill in the art can use the formulae in Meinkoth et al., 1984, *Anal. Biochem.* 138, 267-284 (incorporated herein by reference in its entirety) to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA: DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62.

The hybridized nucleic acids are detected by detecting one or more labels attached to the sample nucleic acids. The labels may be incorporated by any of a number of means well known to those of skill in the art. Detectable labels suitable for use in the present invention include any composition detectable by spectroscopic, photochemical, biochemical, immunochemical, electrical, optical or chemical means. Useful labels in the present invention include fluorescent dyes (e.g., fluorescein, texas red, rhodamine, Alexa fluors, Spectrum dyes, and the like), quantum dots, radiolabels (e.g., $^3$H, $^{125}$I, $^{35}$S, $^{14}$C, or $^{32}$P), and colorimetric labels. Means of detecting such labels are well known to those of skill in the art. Thus, for example, radiolabels may be detected using photographic film or scintillation counters, fluorescent markers may be detected using a photodetector to detect emitted light and fluorescence microscopes. Colorimetric labels are detected by simply visualizing the colored label. Preferably, the hybridizing nucleic acids are detected by fluorescent labels and most preferably, in the context of a fluorescence in situ hybridization (FISH) assay. FISH assays are well known in the art and are described, for example, in the Examples section.

In accordance with the present invention, an isolated polynucleotide, or an isolated nucleic acid molecule, is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. Polynucleotides such as those used in a method of the present invention to detect genes (e.g., by hybridization to a gene) are typically a portion of the target gene that is suitable for use as a hybridization probe or PCR primer for the identification of a full-length gene (or portion thereof) in a given sample (e.g., a cell sample). An isolated nucleic acid molecule can include a gene or a portion of a gene (e.g., the regulatory region or promoter). An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. Preferably, an isolated nucleic acid molecule of the present invention is produced using recombinant DNA technology (e.g., polymerase chain reaction (PCR) amplification, cloning) or chemical synthesis.

According to the present invention, a probe (oligonucleotide probe) is a nucleic acid molecule which typically ranges in size from about 50-100 nucleotides to several hundred nucleotides to several thousand nucleotides in length. Therefore, a probe can be any suitable length for use in an assay described herein, including any length in the range of 50 to several thousand nucleotides, in whole number increments. Such a molecule is typically used to identify a target nucleic acid sequence in a sample by hybridizing to such target nucleic acid sequence under stringent hybridization conditions. Hybridization conditions have been described in detail above.

PCR primers are also nucleic acid sequences, although PCR primers are typically oligonucleotides of fairly short length (e.g., 8-30 nucleotides) that are used in polymerase chain reactions. PCR primers and hybridization probes can readily be developed and produced by those of skill in the art, using sequence information from the target sequence. (See, for example, Sambrook et al., supra or Glick et al., supra).

The nucleotide sequence of the human epidermal growth factor receptor (EGFR) gene is known in the art and can be found under GenBank Accession No. AY588246 (incorporated herein by reference), for example. The nucleotide sequence of the human tyrosine kinase receptor-type receptor (HER2) gene is also known in the art and can be found, for example, under GenBank Accession Nos. M16789, M16790, M16791, M16792 and M11730 (all incorporated herein by reference). Nucleotide probes are also known in the art and available for use as probes to detect EGFR genes or HER2 genes. For example, such a probe for detecting both EGFR and chromosome 7 centromere sequences is available (e.g., LSI EGFR SpectrumOrange/CEP 7 SpectrumGreen probe (Vysis, Abbott Laboratories).

In the method of the invention, the level of EGFR gene amplification and/or polysomy in the tumor cell sample is compared to a control level of EGFR gene amplification and/or polysomy selected from: (i) a control level that has been correlated with sensitivity to an EGFR inhibitor; and (ii) a control level that has been correlated with resistance to the EGFR inhibitor. A patient is selected as being predicted to benefit from therapeutic administration of an EGFR inhibitor, an agonist thereof, or a drug having substantially similar biological activity as the EGFR inhibitor, if the level of EGFR gene amplification and/or polysomy in the patient's tumor cells is statistically similar to or greater than the control level of EGFR gene amplification and/or polysomy that has been correlated with sensitivity to the EGFR inhibitor, or if the level of EGFR gene amplification and/or polysomy in the patient's tumor cells is statistically greater than the level of EGFR gene amplification and/or polysomy that has been correlated with resistance to the EGFR inhibitor. A patient is selected as being predicted to not benefit from therapeutic administration of an EGFR inhibitor, an agonist thereof, or a drug having substantially similar biological activity as the EGFR inhibitor, if the level of EGFR gene amplification and/or polysomy in the patient's tumor cells is statistically less than the control level of EGFR gene amplification and/or polysomy that has been correlated with sensitivity to the EGFR inhibitor, or if the level of EGFR gene amplification and/or polysomy in the patient's tumor cells is statistically similar to or less than the level of EGFR gene amplification and/or polysomy that has been correlated with resistance to the EGFR inhibitor.

Similarly, in the case where HER2 gene amplification and/or polysomy is evaluated, the level of HER2 gene amplification and/or polysomy in the tumor cell sample is compared to a control level of HER2 gene amplification and/or polysomy selected from: (i) a control level that has been correlated with sensitivity to the EGFR inhibitor; and (ii) a control level that has been correlated with resistance to the EGFR inhibitor. A patient is selected as being predicted to benefit from therapeutic administration of the EGFR inhibitor, an agonist thereof, or a drug having substantially similar biological activity as the EGFR inhibitor, if the level of HER2 gene amplification and/or polysomy in the patient's tumor cells is statistically similar to or greater than the control level of HER2 gene amplification and/or polysomy that has been correlated with sensitivity to the EGFR inhibitor, or if the level of HER2 gene amplification and/or polysomy in the patient's tumor cells is statistically greater than the level of HER2 gene amplification and/or polysomy that has been correlated with resistance to the EGFR inhibitor. A patient is selected as being predicted to not benefit from therapeutic administration of an EGFR inhibitor, an agonist thereof, or a drug having substantially similar biological activity as the EGFR inhibitor, if the level of HER2 gene amplification and/or polysomy in the patient's tumor cells is statistically less than the control level of HER2 gene amplification and/or polysomy that has been correlated with sensitivity to the EGFR inhibitor, or if the level of HER2 gene amplification and/or polysomy in the patient's tumor cells is statistically similar to or less than the level of HER2 gene amplification and/or polysomy that has been correlated with resistance to the EGFR inhibitor.

More specifically, according to the present invention, a "control level" is a control level of gene amplification and/or polysomy, which can include a level that is correlated with sensitivity to the EGFR inhibitor or a level that is correlated with resistance to the EGFR inhibitor. Therefore, it can be determined, as compared to the control or baseline level of gene amplification and/or polysomy, whether a patient sample is more likely to be sensitive to or resistant to the EGFR inhibitor therapy (e.g., a good responder or responder (one who will benefit from the therapy), or a poor responder or non-responder (one who will not benefit or will have little benefit from the therapy)).

In one embodiment of the invention wherein gene copy number is assessed (i.e., by gene amplification and/or gene polysomy), patients are classified into six categories with ascending number of copies per cell: (1) Disomy ($\leq 2$ copies of both targets in >90% of cells); (2) Low trisomy ($\leq 2$ copies of the gene in $\geq 40\%$ of cells and 3 copies in 10-40% of the cells); (3) High trisomy ($\leq 2$ copies of the gene in $\geq 40\%$ of cells and 3 copies in $\geq 40\%$ of cells); (4) Low polysomy ($\geq 4$ copies of the gene in 10-40% of cells); (5) High polysomy ($\geq 4$ copies of the gene in $\geq 40\%$ of cells); and (6) Gene Amplification (GA), defined by presence of tight EGFR gene clusters and a ratio gene/chromosome per cell $\geq 2$, or an average of $\geq 15$ copies of EGFR per cell in $\geq 10\%$ of analyzed cells. The present inventors have found that patients with high gene copy numbers or a gain in copy numbers (e.g., gene amplification and/or polysomy including high trisomy, low polysomy or high polysomy) of EGFR and/or HER2 are more likely to have a higher response rate to EGFR inhibitor therapy, a lower rate of progressive disease, a longer time to progression, and a higher rate of long term survivors. The higher the polysomy or overall gain in gene copy number, the better the predicted outcome. The present inventors found that the presence of HER2 gene amplification and/or polysomy in patient tumor cells confers a more sensitive phenotype to EGFR positive patients (e.g., patients showing a gain in EGFR gene copy numbers) and a better outcome to EGFR negative patients (e.g., patients having no or low gain in EGFR gene copy numbers).

The method for establishing a control level of gene amplification or polysomy is selected based on the sample type, the tissue or organ from which the sample is obtained, and the status of the patient to be evaluated. Preferably, the method is the same method that will be used to evaluate the sample in the patient. In a preferred embodiment, the control level is established using the same cell type as the cell to be evaluated. In a preferred embodiment, the control level is established from control samples that are from patients or cell lines known to be resistant or sensitive to gefitinib. In one aspect, the control samples were obtained from a population of matched individuals. According to the present invention, the phrase "matched individuals" refers to a matching of the control individuals on the basis of one or more characteristics which are suitable for the type of cell or tumor growth to be evaluated. For example, control individuals can be matched with the patient to be evaluated on the basis of gender, age, race, or any relevant biological or sociological factor that may affect the baseline of the control individuals and the patient (e.g., preexisting conditions, consumption of particular substances, levels of other biological or physiological factors). To establish a control level, samples from a number of matched individuals are obtained and evaluated in the same manner as for the test samples. The number of matched individuals from whom control samples must be obtained to establish a suitable control level (e.g., a population) can be determined by those of skill in the art, but should be statistically appropriate to establish a suitable baseline for comparison with the patient to be evaluated (i.e., the test patient). The values obtained from the control samples are statistically processed using any suitable method of statistical analysis to establish a suitable baseline level using methods standard in the art for establishing such values. The Examples section describes such statistical methods.

It will be appreciated by those of skill in the art that a control level need not be established for each assay as the assay is performed but rather, a baseline or control can be established by referring to a form of stored information regarding a previously determined control level for sensitive and resistant patients (responders and non-responders), such as a control level established by any of the above-described methods. Such a form of stored information can include, for example, but is not limited to, a reference chart, listing or electronic file of population or individual data regarding sensitive and resistant tumors/patients, or any other source of data regarding control level gene amplification or polysomy that is useful for the patient to be evaluated. For example, one can use the guidelines established above and further described in the Examples for establishing polysomy and for detecting gene amplification, which have already been correlated with responsiveness to an EGFR inhibitor, to rate a given patient sample.

In one embodiment of the present invention, the method includes a step of detecting the expression of a protein, including EGFR or phosphorylated Akt. Protein expression can be detected in suitable tissues, such as tumor tissue and cell material obtained by biopsy. For example, the patient tumor biopsy sample, which can be immobilized, can be contacted with an antibody, an antibody fragment, or an aptamer, that selectively binds to the protein to be detected, and determining whether the antibody, fragment thereof or aptamer has bound to the protein. Protein expression can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry. In a preferred embodiment, immunohistochemical (IHC) analysis is used to detect protein expression. IHC methods and preferred assessment criteria for detection of protein expression are described in detail, for example, in Hirsch et al., *J. Clin. Oncol.* 2003, 21:3798-3807, and are also described in the Examples.

In a preferred, but non-limiting method for assessing protein expression, the following protocol is used as an evaluation of immunohistochemistry results. P-Akt expression and EGFR expression can be scored, in one aspect of the invention, based on intensity and fraction of positive cells, although other scoring systems will be apparent to those of skill in the art, given the guidance provided herein. The intensity score is defined as follows: 0=no appreciable staining in the tumor cells, 1=barely detectable staining in the cytoplasm and/or nucleus as compared with the stromal elements, 2=readily appreciable brown staining distinctly marking the tumor cell cytoplasm and/or nucleus, 3=dark brown staining in tumor cells obscuring the cytoplasm and/or nucleus, or 4=very strong staining of nucleus and/or cytoplasm. The score is based on the fraction of positive cells (0%-100%). The total score is calculated by multiplying the intensity score and the fraction score producing a total range of 0 to 400. For statistical analyses, scores of 0-200 are considered to be negative/low expression, and scores of 201-400 are considered to be positive/high expression. This cut-off level is based on previous studies from the inventors, in which they found a correlation between increased EGFR protein expression and increased gene copy number (Hirsch et al., *J. Clin. Oncol.* 2003, 21:3798-3807). These cut-off levels are convenient levels for performing the assay, but not absolute levels. It is contemplated, for example, that this scoring system can be revised or manipulated, such as by lowering or raising the cut-off score by 5, 10, 15, 20, 25, 30, 35, or more points.

In the method of the invention, the level of EGFR protein expression and/or phosphorylated Akt expression in the tumor cell sample is compared to a control level of EGFR protein expression and/or phosphorylated Akt expression selected from: (i) a control level that has been correlated with sensitivity to an EGFR inhibitor; and (ii) a control level that has been correlated with resistance to the EGFR inhibitor. A patient is selected as being predicted to benefit from therapeutic administration of an EGFR inhibitor, an agonist thereof, or a drug having substantially similar biological activity as the EGFR inhibitor, if the level of EGFR protein expression and/or phosphorylated Akt expression in the patient's tumor cells is statistically similar to or greater than the control level of EGFR protein expression and/or phosphorylated Akt expression that has been correlated with sensitivity to the EGFR inhibitor, or if the level of EGFR protein expression and/or phosphorylated Akt expression in the patient's tumor cells is statistically greater than the level of EGFR protein expression and/or phosphorylated Akt expression that has been correlated with resistance to the EGFR inhibitor. A patient is selected as being predicted to not benefit from therapeutic administration of an EGFR inhibitor, an agonist thereof, or a drug having substantially similar biological activity as the EGFR inhibitor, if the level of EGFR protein expression and/or phosphorylated Akt expression in the patient's tumor cells is statistically less than the control level of EGFR protein expression and/or phosphorylated Akt expression that has been correlated with sensitivity to the EGFR inhibitor, or if the level of EGFR protein expression and/or phosphorylated Akt expression in the patient's tumor cells is statistically similar to or less than the level of EGFR protein expression and/or phosphorylated Akt expression that has been correlated with resistance to the EGFR inhibitor.

Appropriate controls have been discussed above with regard to detection of gene amplification and polysomy, and such discussion can readily be extrapolated to controls for protein expression. As discussed above, a control level for comparison can be any type of control, including a preestablished control that is provided as a form of information. For example, with regard to EGFR protein expression, using the scoring system for EGFR expression described above and in the Examples, a score of greater than about 200 (201-400) is considered to be a patient with high expression (positive for EGFR expression) and a score of about 0-200 is considered to be a patient with low expression (negative for EGFR expression). Other scoring systems can be devised based on comparisons with controls, and patients falling near the cut-off, can be evaluated by other criteria, biomarkers, or techniques in order to confirm a diagnosis. Also, the cut-off can be varied as desired by the clinician or investigator according to patient populations. The cut-off levels described above are convenient levels for performing the assay and optimized by the present inventors given the current data, but are not absolute levels. It is contemplated, for example, that this scoring system can be revised or manipulated, such as by lowering or raising the cut-off score by 5, 10, 15, 20, 25, 30, 35, or more points. With regard to phosphorylated Akt, similar methodology was used.

In one embodiment of the present invention, the method includes an additional step of detection of a mutation in the tyrosine kinase domain of the EGFR gene. In particular, exons 18, 19 and 21 of the EGFR gene are good targets for the evaluation of mutations, since these exons contain about 98% of the 56 EGFR mutations in NSCLC reported to date. In Lynch et al. or Paez et al. (26, 27), somatic mutations were identified in the tyrosine kinase domain of the EGFR gene in the majority of patients with gefitinib-responsive lung cancer, as compared with none of the patients with no response (P<0.001). Mutations were either small, in-frame deletions or amino acid substitutions clustered around the ATP-binding pocket of the tyrosine kinase domain. Similar mutations were detected in tumors from 8% of patients with primary non-small-cell lung cancer who had not been exposed to gefitinib. All mutations were heterozygous, and identical mutations were observed in multiple patients, suggesting an additive specific gain of function. In vitro, EGFR mutants demonstrated enhanced tyrosine kinase activity in response to epidermal growth factor and increased sensitivity to inhibition by gefitinib. Therefore, the present invention contemplates the detection of such mutations in the tumor cell samples for use in combination with or as a secondary screening subsequent to the screening for EGFR gene amplification and/or polysomy and/or for HER2 gene amplification. Detection of one or more mutations in the EGFR gene is predictive that a patient is more likely to respond or benefit from EGFR inhibitor therapy. Detection of no mutations is predictive that a patient is less likely to respond or benefit from EGFR inhibitor therapy. Methods for screening for gene mutations are well-known in the art, are described in Lynch et al. and Paez et al., and include, but are not limited to, hybridization, polymerase chain reaction, polyacrylamide gel analysis, chromatography or spectroscopy, and can further include screening for an altered protein product encoded by the gene (e.g., via immunoblot (e.g., Western blot), enzyme-linked immunosorbant assay (ELISA), radioimmunoassay (RIA), immunoprecipitation, immunohistochemistry, immunofluorescence, fluorescence activated cell sorting (FACS) and immunofluorescence microscopy).

As used herein, the term "selectively binds to" refers to the specific binding of one protein to another (e.g., an antibody, fragment thereof, or binding partner to an protein), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background.

The steps of detection of the biomarkers according to the present invention may be combined in many different combinations as described herein, and the steps can be performed in any order, or substantially simultaneously. Statistical analysis to determine differences between controls and patient samples can be performed using any methods known in the art, including, but not limited to, Fisher's exact test of Pearson's chi-square test for qualitative variables, and using Student's t test or analysis of variance for continuous variables. Statistical significance is typically defined as $p<0.05$. Statistical methods are described in more detail in the Examples.

The method of the present invention is useful for determining or predicting patients that are most likely to respond (e.g., with a therapeutic benefit) to therapy using an EGFR inhibitor, an agonist thereof, or a drug having substantially similar biological activity as the EGFR inhibitor, as well as to determine or predict patients that are most likely not to respond to therapy using an EGFR inhibitor. An agonist, as used herein, is a compound that is characterized by the ability to agonize (e.g., stimulate, induce, increase, enhance, or mimic) the biological activity of a naturally occurring or reference protein or compound. More particularly, an agonist can include, but is not limited to, a compound, protein, peptide, antibody, or nucleic acid that mimics or enhances the activity of the natural or reference compound, and includes any homologue, mimetic, or any suitable product of drug/compound/peptide design or selection which is characterized by its ability to agonize (e.g., stimulate, induce, increase, enhance) the biological activity of a naturally occurring or reference compound. In contrast, an antagonist refers to any compound which inhibits (e.g., antagonizes, reduces, decreases, blocks, reverses, or alters) the effect of a naturally occurring or reference compound as described above. More particularly, an antagonist is capable of acting in a manner relative to the activity of the reference compound, such that the biological activity of the natural or reference compound, is decreased in a manner that is antagonistic (e.g., against, a reversal of, contrary to) to the natural action of the reference compound. Such antagonists can include, but are not limited to, any compound, protein, peptide, or nucleic acid (including ribozymes and antisense) or product of drug/compound/peptide design or selection that provides the antagonistic effect.

Agonists and antagonists that are products of drug design can be produced using various methods known in the art. Various methods of drug design, useful to design mimetics or other compounds useful in the present invention are disclosed in Maulik et al., 1997, *Molecular Biotechnology: Therapeutic Applications and Strategies*, Wiley-Liss, Inc., which is incorporated herein by reference in its entirety. An agonist or antagonist can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, natural or synthetic steroidal compounds, carbohydrates and/or natural or synthetic organic and non-steroidal molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

A drug having substantially similar biological activity as gefitinib refers to a drug having substantially any function(s) exhibited or performed by the reference compound that is ascribed to the reference compound as measured or observed in vivo (i.e., under physiological conditions) or in vitro (i.e., under laboratory conditions).

Other types of EGFR inhibitors can include, but are not limited to, aptamers, RNAi, and ribozymes. Aptamers are short strands of synthetic nucleic acids (usually RNA but also DNA) selected from randomized combinatorial nucleic acid libraries by virtue of their ability to bind to a predetermined specific target molecule with high affinity and specificity. Aptamers assume a defined three-dimensional structure and are capable of discriminating between compounds with very small differences in structure. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that is able to perform biological catalysis (e.g., by breaking or forming covalent bonds). More specifically, ribozymes are antisense RNA molecules that function by binding to the target RNA moiety and inactivate it by cleaving the phosphodiester backbone at a specific cutting site.

Another type of EGFR inhibitor can include an antibody, antigen binding fragment thereof, or an antigen binding peptide or "binding partner". Antibodies are characterized in that they comprise immunoglobulin domains and as such, they are members of the immunoglobulin superfamily of proteins. An antibody can include polyclonal and monoclonal antibodies, divalent and monovalent antibodies, bi- or multi-specific antibodies, serum containing such antibodies, antibodies that have been purified to varying degrees, and any functional equivalents of whole antibodies. Isolated antibodies useful as EGFR inhibitors can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$^2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed as EGFR inhibitors. Binding partners are designed to bind specifically to and inhibit an EGFR may also be evaluated. Examples of the design of such polypeptides, which possess a prescribed ligand specificity are given in Beste et al. (Proc. Natl. Acad. Sci. 96:1898-1903, 1999).

Another embodiment of the invention includes an assay kit for performing any of the methods of the present invention. The assay kit can include any one or more of the following components: (a) a means for detecting in a sample of tumor cells a level of amplification of the epidermal growth factor receptor (EGFR) gene and/or a level of polysomy of the epidermal growth factor receptor (EGFR) gene; (b) a means for detecting in a sample of tumor cells a level of amplification of the HER2 gene; (c) a means for detecting in a sample of tumor cells the expression of EGFR protein; (d) a means for detecting in a sample of tumor cells the expression of phosphorylated Akt protein; and/or (e) a means for detecting in a sample of tumor cells at least one (but can include more than one) mutations in the EGFR gene. The assay kit preferably also includes one or more controls. The controls could include: (i) a control sample for detecting sensitivity to the EGFR inhibitor being evaluated for use in a patient; (ii) a control sample for detecting resistance to the EGFR inhibitor; (iii) information containing a predetermined control level of particular biomarker to be measured with regard to EGFR inhibitor sensitivity or resistance (e.g., a predetermined control level of EGFR gene amplification and/or polysomy that has been correlated with sensitivity to the EGFR inhibitor or resistance to EGFR inhibitor).

In one embodiment, a means for detecting EGFR or HER2 gene amplification and/or polysomy can generally be any type of reagent that can be used in a method of the present invention. Such a means for detecting include, but are not limited to: a probe or primer(s) that hybridizes under stringent hybridization conditions to an EGFR gene or a HER2 gene or a portion of chromosome 7 (chromosome on which EGFR is located) or chromosome 17 (chromosome on which HER2 is located). Nucleic acid sequences for the EGFR and HER2 genes are known in the art and can be used to produce such reagents for detection. Additional reagents useful for performing an assay using such means for detection can also be included, such as reagents for performing in situ hybridization, reagents for detecting fluorescent markers, reagents for performing polymerase chain reaction, etc.

In another embodiment, a means for detecting EGFR or phosphorylated Akt protein expression can generally be any type of reagent that can be used in a method of the present invention. Such a means for detection includes, but is not limited to, antibodies and antigen binding fragments thereof, peptides, binding partners, aptamers, enzymes, and small molecules. Additional reagents useful for performing an assay using such means for detection can also be included, such as reagents for performing immunohistochemistry or another binding assay.

The means for detecting of the assay kit of the present invention can be conjugated to a detectable tag or detectable label. Such a tag can be any suitable tag which allows for detection of the reagents used to detect the gene or protein of interest and includes, but is not limited to, any composition or label detectable by spectroscopic, photochemical, electrical, optical or chemical means. Useful labels in the present invention include: biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the means for detecting of the assay kit of the present invention can be immobilized on a substrate. Such a substrate can include any suitable substrate for immobilization of a detection reagent such as would be used in any of the previously described methods of detection. Briefly, a substrate suitable for immobilization of a means for detecting includes any solid support, such as any solid organic, biopolymer or inorganic support that can form a bond with the means for detecting without significantly affecting the activity and/or ability of the detection means to detect the desired target molecule. Exemplary organic solid supports include polymers such as polystyrene, nylon, phenol-formaldehyde resins, and acrylic copolymers (e.g., polyacrylamide). The kit can also include suitable reagents for the detection of the reagent and/or for the labeling of positive or negative controls, wash solutions, dilution buffers and the like. The kit can also include a set of written instructions for using the kit and interpreting the results.

The kit can also include a means for detecting a control marker that is characteristic of the cell type being sampled can generally be any type of reagent that can be used in a method of detecting the presence of a known marker (at the nucleic acid or protein level) in a sample, such as by a method for detecting the presence of a biomarker described previously herein. Specifically, the means is characterized in that it identifies a specific marker of the cell type being analyzed that positively identifies the cell type. For example, in a lung tumor assay, it is desirable to screen lung epithelial cells for the level of the biomarker expression and/or biological activity. Therefore, the means for detecting a control marker identifies a marker that is characteristic of an epithelial cell and preferably, a lung epithelial cell, so that the cell is distinguished from other cell types, such as a connective tissue or inflammatory cell. Such a means increases the accuracy and specificity of the assay of the present invention. Such a means for detecting a control marker include, but are not limited to: a probe that hybridizes under stringent hybridization conditions to a nucleic acid molecule encoding a protein marker; PCR primers which amplify such a nucleic acid molecule; an aptamer that specifically binds to a conformationally distinct site on the target molecule; and/or an antibody, antigen binding fragment thereof, or antigen binding peptide that selectively binds to the control marker in the sample. Nucleic acid and amino acid sequences for many cell markers are known in the art and can be used to produce such reagents for detection.

The assay kits and methods of the present invention can be used not only to identify patients that are predicted to be responsive to a particular EGFR inhibitor, but also to identify treatments that can improve the responsiveness of cancer cells which are resistant to EGFR inhibitors, and to develop adjuvant treatments that enhance the response of the EGFR inhibitors.

The Examples, which follow, are illustrative of specific embodiments of the invention, and various uses thereof. They are set forth for explanatory purposes only, and are not to be taken as limiting the invention.

EXAMPLES

Example 1

The following example demonstrates the use of detection of EGFR gene amplification and polysomy to predict treatment outcome of NSCLC tumors to EGFR inhibitors (based on the study of an Italian cohort).

Methods

Patient Selection and Study Design

Patients for this study were accrued in three Italian institutions: the Bellaria Hospital, (Bologna), the Scientific Institute University Hospital San Raffaele (Milano), and the Policlinico Monteluce (Perugia). Eligibility included histologically confirmed NSCLC patients with measurable, locally advanced or metastatic disease, who had progressed or relapsed after chemotherapy, and patients ineligible for chemotherapy because they were elderly, had poor performance status, or comorbid medical condition. Before trial inclusion, smoking status was assessed and patients were classified as never, former (smoking cessation >6 months prior to trial inclusion), or current smokers (cessation <6 months before trial inclusion or active smoker). The study was approved by the appropriate ethical review boards and written informed consent was obtained from each patient before entering the study.

From May 2001 to January 2004, 108 patients received gefitinib at the daily oral dose of 250 mg until disease progression, unacceptable toxicity or refusal. The efficacy results for some of the patients were previously reported (28, 29). Patients were evaluated for response according to the RECIST criteria (30). Tumor response was assessed by computer tomography scan every two months, with a confirmatory evaluation to be repeated in responding patients at least 4 weeks after the initial determination of response. Time to disease progression (TTP) was calculated from the date of initiation of gefitinib treatment to the date of detection of progressive disease or last contact. Survival (OS) was calculated from the date of therapy initiation to the date of death or last contact.

Tissue Preparation and Fish Analysis

Tumor specimens were obtained at time of diagnosis prior to any cancer therapy. For each patient, serial 5-µm-thick tissue sections were sliced from paraffin-embedded blocks containing representative malignant cells. Histopathological classification was performed on hematoxylin-eosin (HE) stained section based on the World Health Organization (WHO) criteria (31). Dual-target, dual-color FISH assays were performed using the LSI EGFR SpectrumOrange/CEP 7 SpectrumGreen probe (Vysis, Abbott Laboratories) according to a protocol described elsewhere (10). Using the reference HE-stained slide of the adjacent section where the dominant tumor foci were identified, copy numbers of the EGFR gene and chromosome 7 probes were assessed and recorded independently in at least 100 non-overlapping nuclei with intact morphology. Analysis was performed independently by two observers (FC, MVG) blinded to the patients' clinical characteristics, following strict scoring guidelines. There was a high correlation (r=0.96; p<0.01) between the FISH patterns identified by the two observers suggesting that the selected criteria for scoring were reproducible. Discordant FISH patterns were re-evaluated and a consensus was reached by the two investigators.

According to the frequency of tumor cells with specific number of copies of the EGFR gene and chromosome 7 centromere, patients were classified into six FISH categories with ascending number of copies per cell: (1) Disomy (≤2 copies of both targets in >90% of cells); (2) Low trisomy (≤2 copies of the gene in ≥40% of cells and 3 copies in 10-40% of the cells); (3) High trisomy (≤2 copies of the gene in ≥40% of cells and 3 copies in ≥40% of cells); (4) Low polysomy (≥4 copies of the gene in 10-40% of cells); (5) High polysomy (≥4 copies of the gene in ≥40% of cells); and (6) Gene Amplification, defined by presence of tight EGFR gene clusters and a ratio gene/chromosome per cell ≥2, or an average of ≥15 copies of EGFR per cell in ≥10% of analyzed cells.

RNA Extraction and Quantitative RT-PCR

RNA was isolated, cDNA transcribed, and quantitative real-time polymerase chain reactions performed as described previously (Rosell et al., Clin Cancer Res 2004; 10:1318-25). Microdissection of tumor cells was performed by manual or by laser capture technique using the PALM instrument (P.A.L.M. Microlaser Technologies AG Inc., Bernried, Germany), according to the manufacturer's guidelines. Primers and probes were as follows: Forward EGFR primer: 5'-TCCGTCTCTTGCCGGGAAT-3' (SEQ ID NO:1); Reverse EGFR primer: 5'-GGCTCACCCTCCA-GAACCTT-3' (SEQ ID NO:2); EGFR Taqman probe: 5'-ACGCATTCCCTGCCTCGGCTG-3'. (Gen Bank accession: NM_005228).

Statistical Analysis

Differences between the FISH groups were compared by Fisher's exact test or $\chi^2$ test for qualitative variables and by t-student test or ANOVA for continuous variables. Normality of the distribution was assessed by Kolmogorov-Smirnov test. Time to progression (TTP), overall survival (OS) and the 95% confidence intervals were evaluated by the Kaplan-Meier method (32), comparing the FISH groups by log rank test. Risk factors associated with survival were evaluated using Cox's proportional-hazards regression model with a step-down procedure (33). Only those variables with significant results in univariate analysis were included in the multivariate analysis. The criteria for variable removal was the likelihood ratio statistic based on the maximum partial likelihood estimated (default p-value=0.10 for removal from the model).

Results

Clinical Characteristics

A total of 108 patients entered onto the study and 102 were completely analyzed. Three patients were lost to follow up and FISH results were not obtained in 3 specimens due to tumor necrosis or poor tissue preservation. Nine patients (8.8%) received gefitinib as first-line therapy: one patient for age >80 years, one for refusal to chemotherapy, and 7 patients for comorbidities contraindicating chemotherapy. The remaining patients received chemotherapy prior to gefitinib, and 78.4% of these had received a platinum agent. Median gefitinib treatment duration was 2.8 months (range 0.6-20). At the time of trial inclusion, the majority of patients were current (52.9%) or former smokers (32.4%).

One complete response (CR: 1%), 13 partial responses (PR: 12.7%) and 26 stable diseases (SD: 25.5%) were observed, for an objective response rate (OR=CR+PR) of 13.7%, and an overall disease control rate (DCR: CR+PR+SD) of 39.2%. Final analyses for TTP and OS were performed in April 2004, when at least 3 months had elapsed from the enrollment of the last patient. With a median follow-up of 7.0 months, the median TTP for the whole population was 2.9 months (standard deviation: 5.1 months), the median OS was 7.0 months (standard deviation: 7.2 months), and the 1-year survival was 45.1%.

Table 1 shows the relation between patient characteristics and response, time to progression and survival. Females had a higher response rate (28.6% versus 6.0%, p=0.004), a longer TTP (median 4.5 versus 2.7 months, p=0.02), and a slightly better survival (median 9.0 versus 6.9 months, p=0.059) compared to males. Better response rate was observed also in never smoking patients (40.0% versus 20.8%, p=0.006) compared to former and current smokers, with no difference in TTP and survival. In patients with adenocarcinoma and bronchioloalveolar carcinoma, although the differences in response rates and TTP were not significant, median survival was higher (p=0.02) compared to those with other histologies. Better survival was also observed in patients with PS 0 and 1 (p=0.01) compared to patients with PS 2. Age and disease stage had no correlation with gefitinib activity.

TABLE 1

Characteristics of the non-small-cell lung cancer patients and gefitinib outcome*

| Patient Characteristic* | No. of Patients/% | Objective Response Total/%† | Progressive Disease Total/% | Median Time to Progression in months | Median Survival in months | 1-year % Cumulative Survival ± % SD |
|---|---|---|---|---|---|---|
| Total | 102/100 | 14/14 | 62/60 | 2.9 | 9.4 | 41 ± 5 |
| Sex | | | | | | |
| Male | 67/66 | 4/6 | 46/69 | 2.7 | 8.3 | 37 ± 6 |
| Female | 35/34 | 10/29 | 16/46 | 5.2 | 11.3 | 48 ± 9 |
| P | | .004¶ | .03‖ | .004§ | .03§ | .22§ |
| Stage | | | | | | |
| III | 14/13 | 1/7 | 6/43 | 6.0 | 8.3 | 36 ± 13 |
| IV | 88/87 | 13/15 | 56/64 | 2.7 | 9.5 | 42 ± 5 |
| P | | .7¶ | .15‖ | .3§ | .9§ | .77§ |
| Histology | | | | | | |
| Adenocarcinoma[A] | 54/53 | 8/15 | 34/63 | 3.2 | 11.3 | 45 ± 7 |
| Bronchioloalveolar[A] | 9/9 | 3/33 | 5/56 | 3.0 | 16.5 | 67 ± 16 |
| Squamous cell[B] | 26/25 | 2/8 | 14/54 | 2.2 | 6.5 | 22 ± 9 |
| Large cell[B] | 2/2 | 0 | 2/100 | 0.8 | 0.8 | 0 ± 0 |
| Undifferentiated[B] | 11/11 | 1/9 | 7/64 | 2.1 | 9.0 | 45 ± 15 |
| P ([A] versus [B]) | | .2¶ | .7‖ | .3§ | .03§ | .04§ |
| Performance status‡ | | | | | | |
| 0 | 49/48. | 5/10 | 32/65 | 2.6 | 10.1 | 40 ± 7 |
| 1 | 41/40 | 7/17 | 22/54 | 4.2 | 10.9 | 47 ± 8 |

TABLE 1-continued

Characteristics of the non-small-cell lung cancer patients and gefitinib outcome*

| Patient Characteristic* | No. of Patients/% | Objective Response Total/%† | Progressive Disease Total/% | Median Time to Progression in months | Median Survival in months | 1-year % Cumulative Survival ± % SD |
|---|---|---|---|---|---|---|
| 2 | 12/12 | 2/17 | 8/67 | 2.1 | 2.7 | 22 ± 13 |
| P (0 + 1 versus 2) | | .7¶ | .7‖ | .2§ | .004§ | .007§ |
| Smoking status | | | | | | |
| Never smoker | 15/15 | 6/40 | 6/40 | 5.3 | 10.9 | 47 ± 14 |
| Former smoker | 33/32 | 5/15 | 17/51 | 3.6 | 13.8 | 55 ± 9 |
| Current smoker | 54/53 | 3/6 | 39/72 | 2.3 | 4.5 | 30 ± 6 |
| P (Never versus others) | | .006¶ | .7‖ | .07§ | .25§ | .35§ |

\* Characteristics of 102 patients with histologically confirmed non-small-cell lung cancer with measurable, locally advanced or metastatic disease, progressing or relapsing after chemotherapy, or medical contraindications for chemotherapy who were subsequently treated with 250 mg gefitinib daily.
†Objective Response = Partial and complete response
‡Performance status was defined as 0 = Fully active, able to carry on all pre-disease performance without restriction; 1 = Restricted in physically strenuous activity but ambulatory and able to perform work of a light or sedentary nature, e.g., light house work, office work; and 2 = Ambulatory and capable of all self care but unable to perform any work activities, and up and about more than 50% of waking hours (Eastern 31 Cooperative Oncology Group criteria, 34)
§P values (two-sided) calculated using the log-rank test.
‖P values (two-sided) calculated using Pearson's chi-square test.
¶P values (two-sided) calculated using Fisher's exact test.

Fish and Quantitative RT-PCR

EGFR gene expression was also evaluated by quantitative real-time polymerase chain reaction in 63 specimens. The relative gene expression was 2.90 (range=0.17 to 28.0) in 40 specimens with low EGFR gene copy numbers (disomy to low polysomy) and 7.15 (range=0.19 to 28.3) in 23 specimens with high EGFR gene copy numbers (high polysomy and gene amplification), and was particularly high among nine tumors with gene amplification (average=8.46, range=1.7 to 21.5). There was a significant positive correlation between the relative expression and the gene copy number (Pearson r=0.33; P=0.007), indicating that specimens with gain in copy numbers had higher levels of gene expression.

Fish and Clinical Variables

Disomy was present in 35.3% of cases, low trisomy in 16.7%, high trisomy in 2%, low polysomy in 13.7%, high polysomy in 19.6% and gene amplification in 12.7%.

Figure 1A:
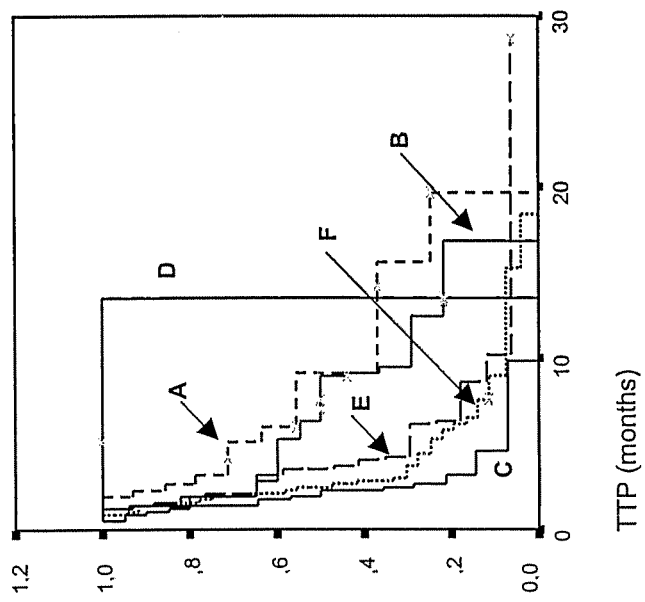

The relationship between FISH results, response to gefitinib, time to disease progression after gefitinib and survival after gefitinib is shown in Table 2. In the disomy category, there were no responders, 75% progressed, and the median TTP and one-year survival rate were low (FIG. 1). Similarly poor results were noted in the groups with low trisomy and low polysomy, where there were no responders, 71% and 86% with progressive disease, short time to progression, and few long term survivors. In contrast, in patients with high trisomy and high polysomy responders were identified, fewer patients with progressive disease, longer times to progression, and longer survival. Patients with gene amplification had a high response rate (53.8%), a low rate of progressive disease (23.1%), a long time to progression, and a high rate of long term survivors (Table 2; FIG. 1).

Patients with high copy numbers of the EGFR gene due to gene amplification or high polysomy were combined (Group 2) and compared with the combined FISH categories having 2 or 3 gene copies (Group 1), as shown in Table 2. Among patients with objective response, 85.7% (12/14) were in Group 2. Furthermore, among patients with disease stabilization, 38.5% (10/26) were in Group 2. The OR rates were 25% in the high polysomy category, 54% in the amplification category, and 36% in the combined Group 2, which was significantly higher compared to Group 1 (2.9%, p<0.001). Disease control rates were also significantly higher in Group 2 compared to Group 1 (66.7% vs. 26.1%; p<0.001). It should be noted that the group with high trisomy contained only two patients, both of whom had a good outcome. If these patients were combined with Group 2 patients, the differences would be even more striking. However, from the molecular standpoint these patients with fewer EGFR gene copies seemed more closely aligned with those with disomy and low trisomy.

TABLE 2

Objective response rate, disease control rate, time to progression and survival analysis according to the groups of NSCLC patients with ascending number of copies of the epidermal growth factor receptor gene.

| | | | FISH Groups | | | | | | | |
|---|---|---|---|---|---|---|---|---|---|---|
| | | | | Group 1 | | | | Group 2 | | |
| Characteristics | | Total Patients | Disomy | Low Trisomy | High Trisomy | Low Polysomy | Total | High Polysomy | Gene Amplification | Total |
| Total | No. | 102 | 36 | 17 | 2 | 14 | 69 | 20 | 13 | 33 |
| | % | 100 | 35.3 | 16.7 | 2.0 | 13.7 | 67.6 | 19.6 | 12.7 | 32.4 |
| Complete and Partial Response | No. | 14 | | | 2 | | 2 | 5 | 7 | 12 |
| | % | 13.7 | | | 100 | | 2.9 | 25 | 53.8 | 36.4 |
| Stable Disease | No. | 26 | 9 | 5 | | 2 | 16 | 7 | 3 | 10 |
| | % | 25.5 | 25.0 | 29.4 | | 14.3 | 23.2 | 35 | 23.1 | 30.3 |

TABLE 2-continued

Objective response rate, disease control rate, time to progression and survival analysis according to the groups of NSCLC patients with ascending number of copies of the epidermal growth factor receptor gene.

| | | Total Patients | FISH Groups | | | | | | | |
|---|---|---|---|---|---|---|---|---|---|---|
| | | | Group 1 | | | | | Group 2 | | |
| Characteristics | | | Disomy | Low Trisomy | High Trisomy | Low Polysomy | Total | High Polysomy | Gene Amplification | Total |
| Progressive Disease | No. | 62 | 27 | 12 | | 12 | 51 | 8 | 3 | 11 |
| | % | 60.8 | 75.0 | 70.6 | | 85.7 | 73.9 | 40 | 23.1 | 33.3 |
| Disease Control Rate | | 39.2 | 25.0 | 29.4 | 100 | 14.3 | 26.1 | 60.0 | 76.9 | 66.7 |
| Median Time to Progression (months) | | 2.9 | 2.5 | 3.6 | 9.3 | 2.1 | 2.5 | 6.6 | 6.0 | 6.3 |
| % Patients without disease progression at 12 months | | 18.6 | 8.3 | 5.9 | 100 | 0 | 8.7 | 35.0 | 46.2 | 39.4 |
| Median Overall Survival (months) | | 7.0 | 6.9 | 10.2 | 13.7 | 3.0 | 6.5 | 8.3 | 9.0 | 9.0 |
| One-year Survival Rate | | 45.1 | 38.9 | 41.2 | 100 | 14.3 | 36.2 | 65.0 | 61.5 | 63.6 |

Figure 2B:
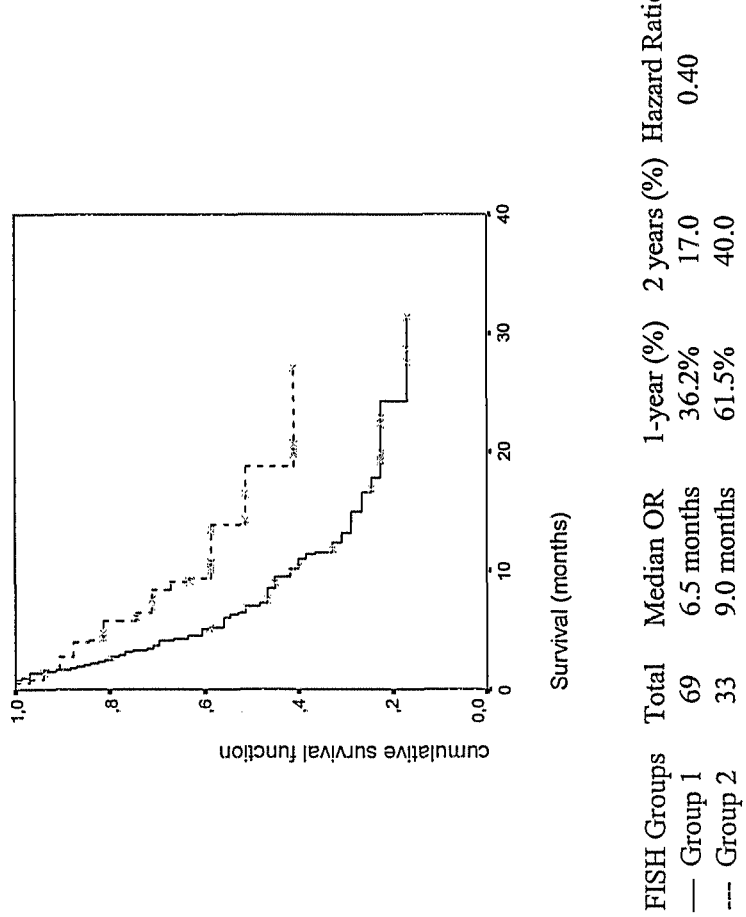

With respect to time to progression, Group 2 patients also did better than Group 1. At 12 months, 91% of Group 1 patients had progressed compared to 61% of Group 2. The difference in TTP by log rank test was significant (p<0.001) (FIG. 2A). Survival was also superior in Group 2 patients compared with Group 1 (FIG. 2B). The one- and two-year survival rates were 63.6% and 40% for Group 2 compared to 36.2% and 17% for Group 1. By log rank test the difference between these groups was statistically significant (p=0.03).

Table 3 shows the relation between EGFR gene status and patient characteristics. Patients with EGFR gene amplification and high polysomy were more likely to be female (p=0.037) and never smokers (p=0.001), while the association with histology was not significant. Multivariate analysis showed that the risk of death was significantly lower in patients from Group 2 (HR: 0.40, 95% CI: 0.21-0.76, p=0.005) and in patients with adenocarcinoma or bronchioloalveolar carcinoma (HR: 0.58, 95% CI 0.35-0.97, p=0.03). Conversely, the risk of death was significantly higher for patients with poor performance status (PS 2) (HR 3.86, 95% CI: 1.76-8.46, p=0.001).

TABLE 3

Epidermal growth factor receptor gene status determined by FISH and patients' characteristics.

| | | | Number of Patients | FISH Patterns[1] | | P value |
|---|---|---|---|---|---|---|
| Characteristics | | | | Group 1 | Group 2 | |
| Total of Patients | | No. | 102 | 69 | 33 | |
| Evaluated by FISH | | % | 100 | 67.6 | 32.4 | |
| Gender | Male | No. | 67 | 50 | 17 | 0.037* |
| | | % | 100 | 74.6 | 25.4 | |
| | Female | No. | 35 | 19 | 16 | |
| | | % | 100 | 54.3 | 45.7 | |
| Histology | Adenocarcinoma | No. | 54 | 36 | 18 | 0.788[2] |
| | | No. | 100 | 66.7 | 33.3 | |
| | Bronchiolo-alveolar Carcinoma | No. | 9 | 6 | 3 | |
| | | % | 100 | 66.7 | 33.3 | |
| | Squamous Cell Carcinoma | No. | 26 | 17 | 9 | |
| | | % | 100 | 65.4 | 34.6 | |
| | Large Cell Carcinoma | No. | 2 | 1 | 1 | |
| | | % | 100 | 50.0 | 50.0 | |
| | Indifferentiated Carcinoma | No. | 11 | 9 | 2 | |
| | | % | 100 | 81.8 | 18.2 | |

TABLE 3-continued

Epidermal growth factor receptor gene status determined by FISH and patients' characteristics.

| | | | Number of Patients | FISH Patterns[1] | | P value |
|---|---|---|---|---|---|---|
| Characteristics | | | | Group 1 | Group 2 | |
| Smoking History | Never Smoker | No. | 15 | 4 | 11 | 0.001*[3] |
| | | % | 100 | 26.7 | 73.3 | |
| | Former Smoker | No. | 33 | 25 | 8 | |
| | | % | 100 | 75.8 | 24.2 | |
| | Current Smoker | No. | 54 | 40 | 14 | |
| | | % | 100 | 74.1 | 25.9 | |

*Statistically significant.
[1]FISH Group 1 includes tumors with disomy, low trisomy, high trisomy and low polysomy; FISH Group 2 includes tumors with high polysomy and gene amplification.
[2]Adenocarcinoma + Bronchioloalveolar Carcinoma vs. others.
[3]Never smoker vs. Former Smoker + Current Smoker.

In summary, these studies examined the correlation between the number of copies per cell of the EGFR gene and gefitinib activity in NSCLC in 102 NSCLC patients who had progressed or relapsed with chemotherapy and were treated with gefitinib at a daily dose of 250 mg. The majority of these patients were male (67%), with ECOG performance status of 0/1 (88%) and the median age was 62 years (range 25-83). Adenocarcinoma was the main histology (52%), followed by squamous-cell carcinoma (26%), undifferentiated carcinoma (11%) and bronchioloalveolar carcinoma (9%). The majority of patients were current (53%) or former smokers (32%). The inventors observed one complete (CR) and 13 partial (PR) responses and 26 disease stabilizations (SD), for an objective response rate (OR=CR+PR) of 14%, and a disease control rate (DCR=CR+PR+SD) of 39%. For the whole population, the median time to progression (TTP) was 2.9 months, and the median survival 7.0 months. Tumor tissue specimens collected at disease diagnosis prior to any cancer therapy were used for determination of the copy number of the EGFR gene per cell by fluorescence in situ hybridization (FISH). The LSI EGFR SpectrumOrange/CEP 7 SpectrumGreen dual color probe (Vysis/Abbott) was used and approximately 100 tumor cells were scored per specimen. According to the number of copies per cell of the EGFR gene and chromosome 7 centromere, patients were classified into two major groups: Group 1 included 69 patients (68%) with no or very low genomic gain (disomy, trisomy, low polysomy); Group 2 included 33 patients (32%) with high polysomy and gene amplification. Group 2 patients had significantly better objective response (OR) and disease control (DCR) rates (OR=36.4%, DCR=66.7%) than patients in Group 1 (OR=2.9%, DCR=26.1%; p<0.001 for both comparisons). In patients with gene amplification, objective response was seen in 53.8% and 76% had disease control. Median time to progression and overall survival were significantly longer in Group 2 (6.3 and 9.0 months) than in Group 1 (2.5 and 6.5 months; p<0.001 and 0.03, respectively). In the multivariate analysis Group 2 had a significantly lower risk of death (Hazard Ratio: 0.44, 95% CI=0.23 to 0.82). In conclusion, EGFR gene amplification and high polysomy identified by FISH are highly effective molecular predictors for gefitinib activity in advanced NSCLC.

The results from the studies described herein demonstrate that gefitinib is highly active in advanced NSCLC patients with EGFR gene amplification or high level of polysomy and support the use of the EGFR-FISH assay for selection of NSCLC patients for tyrosine kinase inhibitor therapy. The strong correlation between response to gefitinib and EGFR genomic gain detected by FISH is expected to be a powerful factor to define patient eligibility for this drug. A positive correlation between clinical outcome and chromosomal polysomy also suggest that assessing chromosome 7 centromeric sequences may contribute to a panel of multiple tests for response prediction. The lack of correlation between patients with no or low genomic gain indicates that the treatment is not effective in this particular patients set, therefore minimizing possibly clinical and certainly financial burden of this therapeutic approach.

The inventors also demonstrated that genomic gains in the EGFR gene can be identified by other molecular techniques such as quantitative real-time PCR, which results correlated in a significant positive pattern with the FISH results.

The question could be raised whether increased EGFR copy number per se has a positive impact on prognosis, independent of the treatment. However, the opposite appears to be the case. The inventors have previously reported that NSCLC patients with resected tumors carrying high EGFR gene copy number have a tendency to a shorter survival (Hirsch et al., 2003, *J. Clin. Oncol.*). Thus, similar to the findings in breast cancer for HER2 and trastuzumab (Herceptin®, Genentech/Roche), increased EGFR gene copy number in NSCLC seems to be a poor prognostic feature but a good predictor for sensitivity to EGFR inhibitors.

Example 2

The following example demonstrates the use of detection of EGFR gene amplification and polysomy to predict treatment outcome of patients with BAC tumors to EGFR inhibitors (based on the SWOG cohort).

Bronchioalveolar carcinoma (BAC) subtypes of NSCLC are characterized by unique pathologic, radiographic, and clinical features (Travis et al., 1999), and appears to be increasing in incidence, particularly in younger non-smoking women (Barsky et al., 1994; Furak et al., 2003). BAC and adenocarcinoma with BAC features have been reported to be particularly sensitive to EGFR tyrosine kinase inhibitors, with response rates of 25-30% (Miller et al., 2003) and prolonged survival in a subset of patients. The inventors and colleagues have previously reported the efficacy of gefitinib in a large cohort of advanced stage BAC patients treated on a prospective clinical trial of the Southwest Oncology Group (S0126) (Gandara et al., 2004). Since archival tumor tissue was collected from the great majority of patients enrolled, the S0126 trial represents a unique pathologic resource for study of EGFR pathways. Based on the inventors' prior experience with NSCLC patients treated with gefitinib it was hypothesized that increased EGFR and/or HER2 gene copy numbers detected by FISH would be associated with increased efficacy of gefitinib in the subset of NSCLCs who have BAC or adenocarcinoma with BAC features. This example reports the results of this analysis in patient tumor tissue from the S0126 study, correlated with clinical outcome.

Material and Methods

All patients enrolled were required to have histologically proven, stage IIIB (by pleural effusion) or IV BAC or adenocarcinoma with BAC features. Pathologic eligibility was based on an institutional definition of BAC, although a central review was subsequently carried out using the World Health Classification (Travis et al., 1999). Histopathological subtypes in this report are based on this central pathology review. Cytologic specimens were not accepted for the BAC diagnosis, and patients with only cytological diagnosis were not eligible for S0126.

Patients were required to have a SWOG performance status of 0-2. Pre-study evaluation included: history and physical examination; complete blood count with differential and platelets, serum chemistries of alkaline phosphatase, SGOT or SGPT, LDH and albumin; chest radiograph; CT of chest, liver, and adrenal glands. Bone scan and/or brain CT or MRI were required only if clinically indicated based on symptoms and physician judgment. Patients with a history of brain metastases were ineligible for the present study. Pregnant or nursing women were ineligible, and women and men of reproductive potential were unable to participate unless they agreed to use an effective contraceptive method. Eligible patients had no other prior malignancy except for adequately treated basal cell or squamous cell skin cancer, in situ cervical cancer, adequately treated stage I or II cancer from which the patient was in complete remission, or any other cancer from which the patient was disease-free for at least five years.

All patients were informed of the investigational nature of this study and signed a written informed consent in accordance with local institutional review board and federal guidelines. All patients had measurable or evaluable disease.

The study consisted of 137 eligible patients divided into two cohorts: chemonaive patients (N=101), and those with previous chemotherapy (N=36); one patient died prior to initiation of treatment. Patients were treated with daily oral gefitinib a dose of 500 mg/day until progression or prohibitive toxicity. Patient characteristics were median age 68 years (range 34-88), male/female distribution 45%/51%, performance status 0-1/2 89%/11%, and stage IIIB/IV 11%/89%.

Histopathological diagnosis and subtyping of BAC was performed on hematoxylin-eosin stained sections by consensus reading by two of the authors (WAF and FRH) using the WHO criteria (Travis et al., 1999). For each patient, serial 4-µm paraffin-embedded tissue sections containing representative malignant cells were sliced. Cell copy number were investigated by FISH using the LSI EGFR SpectrumOrange/CEP 7 SpectrumGreen probe according to protocols described elsewhere (Hirsch et al., 2003, *J. Clin. Oncol.*; Hirsch et al., 2002, *Br. J. Cancer*). Using the reference HE-stained slide of the adjacent section where the dominant tumor foci were identified, copy numbers of the EGFR and HER2 genes and chromosome 7 and 17 probes were assessed and recorded independently in at least 100 non-overlapping nuclei with intact morphology. The FISH analysis was performed independently by two observers (MVG, ACX) blinded to the patients' clinical characteristics. According to the frequency of tumor cells with specific number of copies of the EGFR or HER2 genes and chromosome 7 and 17 centromeres, patients were classified into two strata: FISH negative, with no or low genomic gain (≤4 copies of the gene in ≥40% of cells) and FISH positive, with high level of polysomy (≥4 copies of the gene in ≥40% of cells) or gene amplification, defined by presence of tight gene clusters and a ratio gene/chromosome per cell ≥2, or ≥15 copies of the genes per cell in ≥10% of analyzed cells.

Statistical Methods:

Outcome Definitions

Response evaluation was performed by standard criteria (RECIST) (Therasse et al., 2000). Only patients with measurable disease were included in the response evaluation, while the survival analysis included all the patients. Survival data were analysed from the day the patient started gefitinib treatment until death. Overall survival (OS) was calculated as the time from registration to S0126 to death from any cause or last contact. Progression-free survival (PFS) was calculated as the time from registration to S0126 to either progression of disease or death from any cause or last contact.

Analysis Methods

Survival curves were estimated by the product-limit method (Kaplan and Meier; 1958) and compared using the log rank test (Mantel, 1966). Cox proportional hazards regression was used to assess the influence of EGFR FISH and standard prognostic factors on survival outcomes and to estimate hazard ratios (Cox, 1972). Multivariate models were constructed using backward stepwise regression methods. All univariately significant covariates were included in the stepwise selection.

Results

Protocol S0126 enrolled 145 patients, of whom 8 were ineligible and one did not receive protocol treatment, leaving 136 eligible patients for analysis. Among those, 81 patients had tumour tissue available for EGFR gene analysis by FISH analysis (Table 4) and 56 had tissue available for HER2 gene analysis by FISH.

TABLE 4

Demographic data of the FISH cohort compared to the total SWOG S0126 cohort.

| Characteristics | S0126 Cohort (N = 136) | EGFR/FISH (N = 81) | | |
|---|---|---|---|---|
| | | Positive | Negative | Total |
| Females | 69 (51%) | 13 (50%) | 28 (51%) | 41 (51%) |
| Males | 67 (49%) | 13 (50%) | 27 (49%) | 40 (49%) |
| Smokers | 97 (71%) | 20 (77%) | 39 (71%) | 59 (73%) |
| Never smokers | 39 (29%) | 6 (27%) | 16 (29%) | 22 (27%) |
| PS = 0 | 62 (46%) | 13 (50%) | 22 (40%) | 35 (43%) |
| PS = 1 | 59 (43%) | 11 (42%) | 23 (42%) | 34 (42%) |
| PS = 2 | 15 (11%) | 2 (8%) | 10 (18%) | 12 (15%) |
| ADC | 11 (11%) | 5 (20%) | 2 (4%) | 7 (9%) |
| ADC with BAC | 34 (34%) | 8 (32%) | 16 (29%) | 24 (30%) |
| BAC Mucinous | 17 (17%) | 1 (4%) | 13 (24%) | 14 (18%) |
| BAC non-Mucinous | 37 (37%) | 11 (44%) | 24 (44%) | 35 (44%) |

Figure 4A:
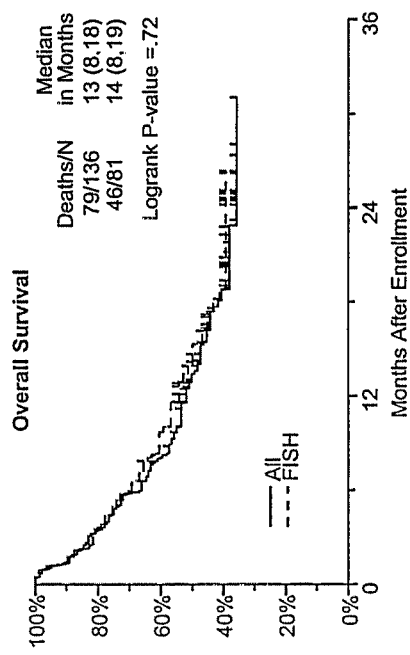
FIG. 4A shows survival curves for the whole S 0126 cohort (N=136 patients) compared to the EGFR FISH sub cohort (N=81 patients).

There were no statistical differences in gender, smoking status, performance status and histology between the total S0126 cohort and the sub-cohort of 81 patients who underwent EGFR FISH analysis (Table 4). Similarly, no statistical difference in survival outcome between the total S0126 population and the EGFR FISH sub-cohort was observed (FIG. 4A). Thus, the EGFR FISH sub-cohort appeared representative of the total S0126 population.

The number of patients in each EGFR FISH category is shown in Table 5. Altogether, 26/81 patients (32%) were positive for EGFR FISH, and there were no significant differences between the EGFR FISH positive and negative groups in terms of gender, histology, smoking status or performance status (Table 4). For response analysis, 55 out of the 81 EGFR FISH patients had measurable disease. In the FISH positive group 5 of 19 patients (26%) had objective response and 12 patients (63%) had disease control (objective response or stable disease), while in the FISH negative group 4 of 36 patients (11%) had objective response (p=0.14) and 14 patients (39%) had disease control (p=0.087) (Table 5).

TABLE 5

Treatment outcome according to EGFR FISH strata.

| EGFR FISH result | No. pts. | RSP (%)[1] | DCR (%)[1] | TTP (mo) (95% CI) | Median survival (mo) | 1-year survival (%) |
|---|---|---|---|---|---|---|
| FISH negative | 55 | 4/36 (11%) | 14/36 (39%) | 4 (2-5) | 4 (2-5) | 42% (29%-55%) |
| FISH positive | 26 | 5/19 (26%)* | 12/19 (63%)** | 9 (3-20) | >18*** | 81% (65%-96%) |
| TOTAL | 81 | 9/55 (16%) | 26/55 (47%) | 4 (2-6) | 14 (8-19) | 54% (43%-65%) |

[1]Limited to the subgroup of patients with measurable disease.
*p = 0.15,
**p = 0.087
***Median survival not yet reached.

Figure 4B:
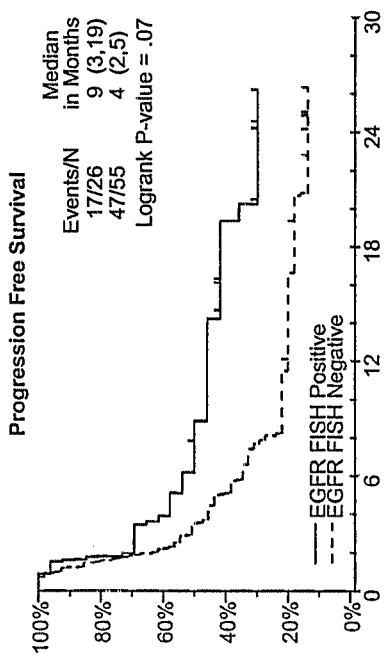
FIG. 4B shows progression free survival for the EGFR FISH positive and FISH negative groups.
Figure 4C:
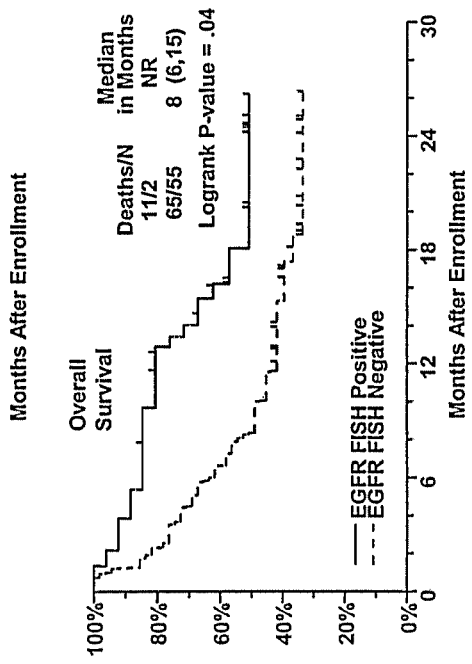
FIG. 4C shows the overall survival curves for the EGFR FISH positive and FISH negative groups.

All 81 eligible patients with assessable tumor tissue for EGFR FISH analysis were included in the survival analysis. The progression free survival and overall survival curves for patients with FISH positive and negative tumors are shown in FIGS. 4B and 4C, respectively. The median progression-free survival time for the FISH negative patients was 4 months (95% C.I.: 2, 5) versus 9 months (95% C.I.: 3, 20) for the FISH positive patients with a hazard ratio of 1.67 (p=0.072) (95% CI: 0.96, 2.91, p=0.072) (FIG. 4B). The median survival time for the FISH negative patients was 8 months (95% C.I.: 6, 15). While the median survival for the FISH positive patients has not yet been reached, it is approaching 18 months, with a hazard ratio of 2.02 (95% CI: 1.03, 3.99, p=0.042) (FIG. 4C).

The response rates and survival were also analyzed with respect to histological subtypes. Among the 8 patients with adenocarcinoma no responders were observed, but 2 patients had stable disease (DCR 2/8=25%). However, among 27 patients with adenocarcinoma with BAC features 5 patients (19%) achieved response and 12 patients (44%) stable disease (DCR 17/27=63%). In the BAC non-mucinous group 6 out of 20 patients (30%) had response and 8 patients (40%) had stable disease (DCR 14/20=70%), while in the BAC mucinous group none of the 11 patients had response or stable disease (chi-square p=0.0004).

A multivariate Cox regression model (Table 6) was used to assess the possibility that the effect of EGFR copy number by FISH on survival could be explained by other standard prognostic factors. EGFR copy number by FISH remained a significant prognostic factor for both overall (p=0.0261) and progression-free survival (p=0.034) after accounting for smoking status, sex, histology and performance status.

TABLE 6

Multivariate analysis for overall survival in patients with data for all the variables (N = 80 pts)

| Variable | No. Pts (%) | Hazard Ratio (95% CI) | P-value |
| --- | --- | --- | --- |
| Current/Former Smokers | 58 (73%) | 3.72 (1.67-8.30) | 0.0013 |
| Adenocarcinoma | 7 (9%) | 4.86 (1.69-14.01) | 0.0034 |
| Performance status 2 | 12 (15%) | 4.24 (1.95-9.25) | 0.0003 |
| BAC Mucinous | 14 (18%) | 2.86 (1.43-5.73) | 0.0030 |
| EGFR FISH negative | 55 (69%) | 2.50 (1.12-5.62) | 0.0261 |

Discussion

This study demonstrates that increased EGFR gene copy number detected by FISH is associated with improved survival after gefitinib therapy in patients with advanced stage BAC and adenocarcinoma with BAC features, a subset of NSCLC that may serve as a model for study of EGFR pathways due to its underlying biologic characteristics (Gandara et al., 2004). In the current study, about one third of the patients had increased EGFR gene copy number, and these patients also had a trend for higher response rates and a longer time to progression after gefitinib therapy. While RECIST response assessment is commonly not applicable in patients with BAC because the diffuse pulmonary infiltration cannot be measured, without being bound by theory, the inventors believe that the significant difference in survival between patients with EGFR FISH positive and negative tumors strongly support the hypothesis that increased gene copy number associates with increased efficacy of gefitinib. There is very little information in the literature regarding survival for patients with advanced BAC. In a study by Breathnach et al (Breathnach et al., 1999), 28 patients with advanced BAC treated with chemotherapy or radiotherapy were analyzed. The median survival time from start of initial treatment was 11.7 months (95CI 8.7-16.7). In a previous SWOG trial (S9714) evaluating paclitaxel in advanced BAC, the median survival was 12 months (West et al., 2005). In the current study, the median survival time for the FISH positive group has not yet been reached but is approaching 18 months versus 8 months for the FISH negative group. The inventors and colleagues have previously reported that increased EGFR gene copy number was associated with a poor prognosis in patients with surgically resected NSCLC (Hirsch et al., 2003, J. Clin. Oncol.). In this study, the inventors verify that increased EGFR gene copy number is a positive predictive marker for improved survival under the influence of gefitinib therapy. These observations are similar to data reported for breast cancer patients with HER2 gene amplification, who have a poor prognosis but a greater likelihood of benefiting from trastuzumab (Herceptin®) (Slamon et al., 2001).

Demographic and survival data were compared between the EGFR FISH positive subpopulation and the total study population, and no differences were observed in terms of known prognostic factors such as gender, smoking status, performance status or histology. In addition, there was no difference in overall survival between the total population and the FISH-tested cohort.

The focus of this example is the predictive value of EGFR FISH for survival in patients with advanced stage BAC. Correlation with other methods of assessing the biologic viability of EGFR and associated signal transduction pathways, such as EGFR protein levels, EGFR mutation analysis, and measurement of downstream markers like AKT and MAPK is discussed elsewhere herein and can be further described with regard to advanced BAC. MAPK levels, as assessed by immunohistochemistry (IHC), are predictive of sensitivity to gefitinib in BAC tumors (Gandara et al., 2004) and may be included as an additional biomarker in the methods herein.

The clinical implications of these findings are considerable in regard to patient selection for therapy with EGFR tyrosine kinase inhibitors (EGFR TKIs). BAC is a disease entity that appears to be increasing in incidence (Barsky et al., 1994; Furak et al., 2003). While preliminary studies have demonstrated relatively high response rates for EGFR inhibitors in patients with BAC and its histological subtypes (West et al., 2005; Patel et al., 2003; Miller et al., 2004), no studies have yet demonstrated survival benefit from these agents in this patient population. The current study demonstrated a significant survival benefit in EGFR FISH positive patients indicating that increased EGFR gene copy numbers detected by FISH can be used as a marker to assess survival potential in patients to be treated with EGFR TKIs. FISH technology is applicable for clinical use, as analysis is performed on routine paraffin embedded material.

Example 3

The following example demonstrates the use of EGFR protein expression, phosphorylated AKT expression, and the combination of these markers with EGFR gene copy numbers and EGFR mutation to predict outcome to EGFR inhibitor therapy in NSCLC patients (Italian cohort).

Methods

Patient Selection and Study Design

Patients included in this study were accrued from a prospective study of gefitinib (Cappuzzo et al., 2004, *J. Natl. Cancer Inst.*) and the Expanded Access Study of gefitinib conducted at Bellaria Hospital (Bologna), Scientific Institute University Hospital San Raffaele (Milano), and Policlinico Monteluce (Perugia). Complete clinical information and tissue blocks were available from 80 out of 106 patients enrolled in the Akt clinical trial (Cappuzzo et al., ibid.), and from an additional 22 patients in the Expanded Access Study who were treated consecutively at the end of the Akt study and followed in the same way as patients in the Akt trial. These studies were approved by the Bellaria Hospital institutional ethical review board, and written informed consent was obtained from each patient before enrollment. In the subgroup of patients participating in the Expanded Access Study of gefitinib, institutional review board approval was obtained according to Good Clinical Practice, and specific written informed consent was obtained from each patient (Expanded Access Study consent form, Italian version).

Eligibility for both studies included histologically confirmed NSCLC with measurable, locally advanced or metastatic disease, progressing or relapsing after chemotherapy or with medical contraindications for chemotherapy. Patients had performance status ranging from grade 0 to 2. Performance status was defined according to Eastern Cooperative Oncology Group (Oken et al., 1982) and considered grade 0 when the patient was fully active and able to perform all pre-disease activities without restriction, grade 1 when the patient was restricted in physically strenuous activity but ambulatory and able to perform work of a light or sedentary nature, and grade 2 when the patient was ambulatory and capable of all self-care but unable to perform any work activities.

Patients received gefitinib (250 mg per day) and were evaluated for response according to the Response Evaluation Criteria in Solid Tumors criteria (Therasse et al., 2000). Tumor response was assessed by computer tomography scan after 2 months, with a confirmatory evaluation to be repeated in responders and in patients with stable disease at least 4 weeks after the initial determination of response. Time to disease progression was calculated from the date of initiation of gefitinib treatment to the date of detection of progressive disease or to the date of last contact. Survival was calculated from the date of therapy initiation to the date of death or to the date of last contact.

Tissue Preparation and Protein Analysis

Tumor specimens were obtained before any cancer therapy and embedded in paraffin. Serial sections (4 μm) containing representative malignant cells were stained with hematoxylin and eosin and classified based on the World Health Organization criteria (Travis et al., 1999).

EGFR protein expression was evaluated by immunohistochemistry using methods and assessment criteria described elsewhere (Hirsch et al., 2003, *J. Clin. Oncol.*) with the mouse anti-human EGFR, clone 31G7 monoclonal antibody (Zymed Laboratories, Inc., San Francisco, Calif.). P-Akt was also detected by immunohistochemistry using the rabbit anti-mouse P-Akt (Ser 473) polyclonal antibody (Cell Signaling Technology, Beverly, Mass., USA), according to the manufacturer's protocol. P-Akt expression and EGFR expression were scored based on intensity and fraction of positive cells. The intensity score was defined as follows: 0=no appreciable staining in the tumor cells, 1=barely detectable staining in the cytoplasm and/or nucleus as compared with the stromal elements, 2=readily appreciable brown staining distinctly marking the tumor cell cytoplasm and/or nucleus, 3=dark brown staining in tumor cells obscuring the cytoplasm and/or nucleus, or 4=very strong staining of nucleus and/or cytoplasm. The score was based on the fraction of positive cells (0%-100%). The total score was calculated by multiplying the intensity score and the fraction score producing a total range of 0 to 400. For statistical analyses, scores of 0-200 were considered negative/low expression, and scores of 201-400 were considered positive/high expression. This cut-off level was based on consistency with previous studies from our group, in which we found a correlation between increased EGFR protein expression and increased gene copy number (Hirsch et al., 2003, ibid.) Immunohistochemistry assays were scored jointly by two investigators, blinded to clinical, FISH, and EGFR mutation results, and if discrepancies occurred, a consensus score was made by the two readers after discussion of the slide.

Statistical Analysis:

Differences between and among groups were compared using Fisher's exact test or Pearson's chi square test for qualitative variables and using student's t test or analysis of variance for continuous variables. Normality of the distribution was assessed using the Kolmogorov-Smirnov test (Curiel et al., 1990). Time to progression, overall survival, and 95% confidence intervals were calculated and evaluated by the Kaplan-Meier method (Don et al., 1991); different groups were compared using the log-rank test. Association of risk factors associated with survival was evaluated using Cox proportional hazards regression modeling with a step-down procedure (Armitage and Berry, 1994). Only those variables with significant results in univariate analysis were included in the multivariable analysis. The criterion for variable removal was the likelihood ratio statistic, based on the maximum partial likelihood estimates (default P value of 0.10 for removal from the model). The study design guarantees independence of the observations. The proportional hazard assumption was tested by log-survival function analysis and found to hold. All statistical tests were two-sided and statistical significance was defined as P<0.05. All analyses were performed using the statistical package SPSS version 11.5 (SPSS Italia srl, Bologna, Italy).

Results

Clinical Characteristics

The clinical outcome based on gender, stage, histology, performance status, and smoking status, most of which was reported in previous publication (Cappuzzo et al, JNCI, 2004), is shown in Table 1 (see Example 1). For the entire group, the objective response rate was 14%, the progression rate was 60%, the median time to progression was 2.9 months, the median survival was 9.4 months, and 1-year survival was 40.7%. Female sex (mean difference 22.6%, 95% CI: 6.6 to 38.6, P=0.004) and never smoking status (mean difference 30.8%, 95% CI: 5.3 to 56.3, P=0.006) were statistically significantly associated with better response, and female sex (mean difference 3.0 months, 95% CI: 4.5 to 10.5 months, P=0.03,), adenocarcinoma and bronchioloalveolar histology (mean difference 5.0 months, 95% CI: 2.8 to 7.2 months, P=0.03), and performance status 0-1 (mean difference 7.4 months, 95% CI: 5.6 to 9.1 months, P=0.004) were statistically significantly associated with longer survival.

Time to disease progression was calculated from the date of initiation of gefitinib treatment to the date of detection of progressive disease or to the date of last contact. Survival was calculated from the date of therapy initiation to the date of death or to the date of last contact. Statistical significance of differences between groups were evaluated with the log-rank test.

EGFR Protein Expression and Clinical Outcome

Figure 3A:
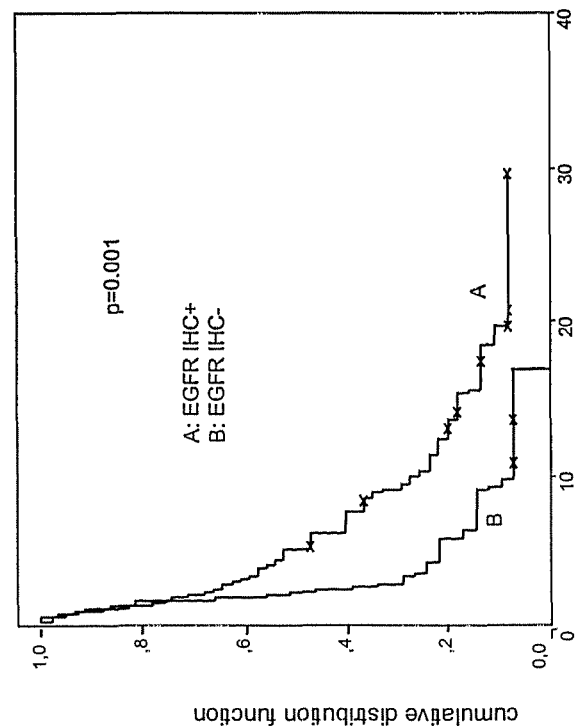
FIGS. 3A and 3B show Kaplan-Meier curves for time to disease progression (FIG. 3A) and survival (FIG. 3B), analyzed according to level of protein expression.
Figure 3B:
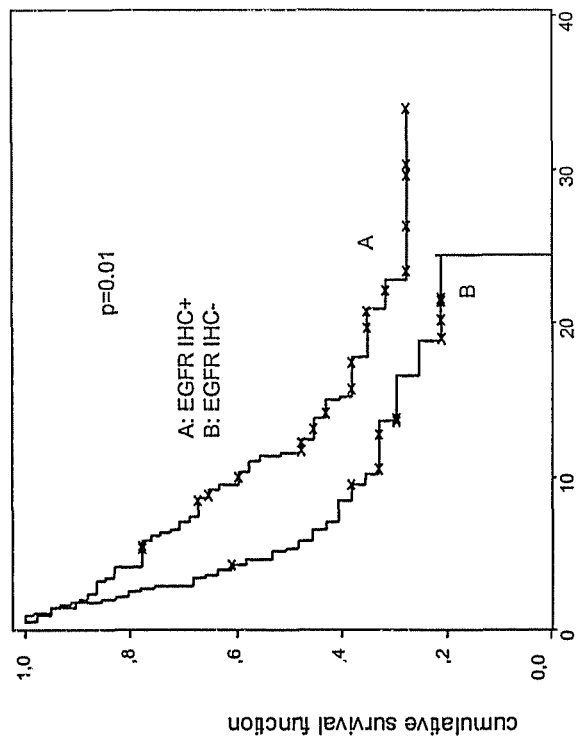

EGFR protein expression was evaluated by immunohistochemistry in 98 patients (data not shown) and the outcome of patients according to protein score is shown in Table 7a and FIG. 3A-3B. Patients with the lowest scores (0-99) had no response, and only one had stable disease. These patients had a short time to progression (median 2.1 months) and short median survival (4.5 months) and 27% had 1-year survival. Patients with scores of 100-199 also had a poor outcome, with a 65% rate of progressive disease, short time to progression (median 2.3 months), and poor survival (only 35% of the patients alive at 1 year). Because their outcomes were similarly poor, the 40 patients (41%) with scores below 100 and 100-199 were combined (EGFR IHC−). Patients with EGFR immunohistochemistry scores of 200-299 and of 300-399 had much better outcomes than patients in the EGFR IHC− group, and because they had similar response rates, progression times, and survival, they were also grouped together (EGFR IHC+). EGFR IHC+ patients, compared with IHC− patients, had significantly higher objective response rate (21% versus 5%, P=0.03), lower progression rate (44.8% versus 80%, P<0.001), longer time to progression (5.2 versus 2.3 months, P=0.001), and longer survival (11.5 versus 5.0 months, P=0.01). Protein status was not associated with clinical characteristics (Table 8) but was statistically significantly correlated with gene copy numbers (Pearson r=0.28, P=0.006).

TABLE 7a

EGFR-Protein Expression and Clinical Outcome in 98 patients with advanced NSCLC treated with gefitininb.

| IHC Score | N | OR | PD | TTP (mo) | MS (mo) | 1-year |
|---|---|---|---|---|---|---|
| Total: | 98 (100%) | 14 (14%) | 58 (59%) | 2.9 | 9.5 | 41 ± 5 |
| 0-99 | 20 (20%) | 0 (0%) | 19 (95%) | 2.1 | 4.5 | 27 ± 10 |
| 100-199 | 20 (20%) | 2 (10%) | 13 (65%) | 2.3 | 5.3 | 35 ± 10 |
| 200-299 | 15 (15%) | 4 (26%) | 5 (33%) | 8.6 | 15.2 | 71 ± 12 |
| 300-400 | 43 (44%) | 8 (19%) | 21 (49%) | 4.5 | 11.3 | 41 ± 8 |
| EGFR IHC ÷ (<200) | 40 (41%) | 2 (5%) | 32 (80%) | 2.3 | 5.0 | 31 ± 7 |
| EGFR IHC + (≥200) | 58 (59%) | 12 (21%) | 26 (45%) | 5.2 | 11.5 | 48 ± 7 |
| P (IHC÷ vs. IHC+) | | 0.03 | <0.001 | 0.001 | 0.01 | 0.01 |

*Characteristics of 102 patients with histologically confirmed non-small cell lung cancer with measurable, locally advanced or metastatic disease, progressing or relapsing after chemotherapy, or medical contraindications for chemotherapy that were subsequently treated with 250 mg gefitinib daily. OR = objective response, PD = progressive disease, TTP = time to progression MS = median overall survival. Protein status by immunohistochemistry (IHC) was defined was based on fraction of positive cells; 0-100% and staining intensity in a scale from 1-4. The total score was calculated by multiplying the intensity score and the fraction score, making a total range of 0-400.
† P values (two-sided) calculated using the log rank test
‡P values (two-sided) calculated using Pearson's chi-square test
§ P values (two-sided) calculated using Fisher's exact test

EGFR Mutation and Clinical Outcome

Mutation analysis for EGFR exons 18, 19, and 21 was performed in a total of 89 case patients (60 microdissected and 29 non-microdissected specimens). EGFR mutations were found in 15 patients (EGFR mutation positive=17%), 12 from microdissected and three from non-microdissected specimens (P=0.30), and consisted of missense mutations in exon 21 (n=8) or small in-frame deletions in codons 746-753 in exon 19 (n=7) (Tables 7b and 9). All of these mutations have previously been described (11-13), with the exception of the missense mutation in exon 21 (valine 851 to isoleucine, V851I), which occurred in a male patient experiencing progressive disease. The presence of EGFR mutations was associated with never-smoking history (P=0.007). The associations with sex and histology were not statistically significant (P=0.10 for both), although mutations were more frequent in women and in patients with adenocarcinoma (Table 8).

TABLE 7b

EGFR Mutation and Clinical Outcome in 89 patients with advanced NSCLC treated with gefitininb.

| EGFR Mutations | N | OR | PD | TTP (mo) | MS (mo) | 1-year |
|---|---|---|---|---|---|---|
| Total: | 89 (100%) | 12 (13%) | 56 (63%) | 2.9 | 9.4 | 41 ± 5 |
| Mutation Absent | 74 (83%) | 4 (5%) | 50 (68%) | 2.6 | 8.4 | 38 ± 6 |
| Mutation Present | 15 (17%) | 8 (53%) | 6 (40%) | 9.9 | 20.8 | 57 ± 13 |
| P (Mutation Absent vs. Present) | | 0.001 | 0.04 | 0.02 | 0.09 | 0.22 |

TABLE 8

Epidermal growth factor receptor (EGFR) and characteristics of the non-small-cell lung cancer patients according to FISH, protein and gene mutation status*

| Patient Characteristics | EGFR FISH status | | EGFR protein status | | EGFR gene mutation | |
|---|---|---|---|---|---|---|
| | Positive, N/% | Negative, N/% | Positive, N/% | Negative, N/% | Present, N/% | Absent, N/% |
| Total | 33/32 | 69/68 | 58/59 | 40/41 | 15/17 | 74/83 |
| Sex | | | | | | |
| Male | 17/51 | 50/72 | 37/64 | 27/67 | 7/47 | 51/69 |
| Female | 16/48 | 19/28 | 21/36 | 13/32 | 8/53 | 23/31 |
| P | .04† | | .70† | | .10† | |
| Histology | | | | | | |
| Adenocarcinoma^A | 18/54 | 36/52 | 29/50 | 22/55 | 10/67 | 40/54 |
| Bronchioloalveolar^A | 3/9 | 6/9 | 4/7 | 5/12 | 2/13 | 6/8 |
| Squamous cell^B | 9/27 | 17/25 | 18/31 | 8/20 | 1/7 | 20/27 |
| Large cell^B | 1/3 | 1/1 | 1/2 | 1/2 | 0 | 1/1 |
| Undifferentiated^B | 2/6 | 9/13 | 6/10 | 4/10 | 2/13 | 7/9 |
| P (^A versus ^B) | .78† | | .29† | | .10† | |
| Performance status | | | | | | |
| 0 | 13/39 | 36/52 | 27/47 | 20/50 | 8/53 | 35/47 |
| 1 | 13/39 | 28/40 | 27/47 | 12/30 | 5/33 | 31/42 |
| 2 | 7/21 | 5/7 | 4/7 | 8/20 | 2/13 | 8/11 |
| P (0 + 1 versus 2) | .053‡ | | .06‡ | | .60‡ | |
| Smoking status | | | | | | |
| Never smoker | 11/33 | 4/6 | 10/17 | 5/12 | 6/40 | 7/9 |
| Former smoker | 8/24 | 25/36 | 21/36 | 11/27 | 5/33 | 24/32 |

TABLE 8-continued

Epidermal growth factor receptor (EGFR) and characteristics of the non-small-cell lung cancer patients according to FISH, protein and gene mutation status*

| Patient Characteristics | EGFR FISH status Positive, N/% | EGFR FISH status Negative, N/% | EGFR protein status Positive, N/% | EGFR protein status Negative, N/% | EGFR gene mutation Present, N/% | EGFR gene mutation Absent, N/% |
|---|---|---|---|---|---|---|
| Current smoker | 14/42 | 40/58 | 27/47 | 24/60 | 4/26 | 43/58 |
| P (Never versus others) | .001‡ | | .52† | | .007‡ | |

*Characteristics of 102 patients with histologically confirmed non-small-cell lung cancer patients with measurable, locally advanced or metastatic disease, progressing or relapsing after chemotherapy, or medical contraindications for chemotherapy who were subsequently treated with 250 mg gefitinib daily Performance status was defined as 0 = Fully active, able to carry on all pre-disease performance without restriction; 1 = Restricted in physically strenuous activity but ambulatory and able to perform work of a light or sedentary nature, e.g., light house work, office work; and 2 = Ambulatory and capable of all self care but unable to perform any work activities, and up and about more than 50% of waking hours (Eastern Cooperative Oncology Group criteria, 34) FISH = fluorescence in situ hybridization.
†P values (two-sided) calculated using Pearson's chi-square test
‡P values (two-sided) calculated using Fisher's exact test

TABLE 9

```
Exon 19 deletions

EGFR          739   K   I   P   V   A   I   K   E   L   R   E   A   T   S   P   K   A   N       756
protein             SEQ ID NO: 4
EGFR         2215   AAA ATT CCC GTC GCT ATC AAG GAA TTA AGA GAA GCA ACA TCT CCG AAA GCC AAC      2268
gene                SEQ ID NO: 5
Patient             AAA ATT CCC GTC GCT ATC AAG ... ... ... ... ...         TCT CCG AAA GCC AAC
15                  SEQ ID NO: 6
Patients            AAA ATT CCC GTC GCT ATC AA. ... ... ... ... .A ACA TCT CCG AAA GCC AAC
19, 30,             SEQ ID NO: 7
41 and
53*
Patient             AAA ATT CCC GTC GCT ATC AAG GAA T.. ... ... ... ... .CT CCG AAA GCC AAC
57                  SEQ ID NO: 8
Patient             AAA ATT CCC GTC GCT ATC AAG ... ... ... ... ... ACA TCT CCG AAA GCC AAC
75†                 SEQ ID NO: 9

Exon 21 mutations

EGFR          850   H   V   K   I   T   D   F   G   L   A   K   L   L   G               863
protein             SEQ ID NO: 10
EGFR         2538   CAT GTC AAG ATC ACA GAT TTT GGG CTG GCC AAA CTG CTG GGT             2589
gene                SEQ ID NO: 11
Patients            H   V   K   I   T   D   F   G   R   A   K   L   L   G
1, 2,               SEQ ID NO: 12
16, 26,             CAT GTC AAG ATC ACA GAT TTT GGG CGG GCC AAA CTG CTG GGT
31, 38,             SEQ ID NO: 13
100
(substi-
tution
2573
T > G)‡
Patient             H   I   K   I   T   D   F   G   L   A   K   L   L   G
3                   SEQ ID NO: 14
(Substi-            CAT ATC AAG ATC ACA GAT TTT GGG CTG GCC AAA CTG CTG GGT
tution              SEQ ID NO: 15
2541
G > A)#

Primers used for Mutation Analysis

Exon 18        GACCCTTGTCTCTGTGTTCTTGT
forward        SEQ ID NO: 16
Exon 18        TATACAGCTTGCAAGGACTCTGG
reverse        SEQ ID NO: 17
outside
Exon 18        CCAGACCATGAGAGGCCCTG
reverse        SEQ ID NO: 18
inside
Exon 19        CACAATTGCCAGTTAACGTCTTC
forward        SEQ ID NO: 19
Exon 19        AGGGTCTAGAGCAGAGCAGC
reverse        SEQ ID NO: 20
outside
Exon 19        GCCTGAGGTTCAGAGCCAT
reverse        SEQ ID NO: 21
inside
Exon 21        CATGATGATCTGTCCCTCACAG
forward        SEQ ID NO: 22
```

TABLE 9-continued

| | | |
|---|---|---|
| Exon 21 reverse outside | CTGGTCCCTGGTGTCAGGAA | SEQ ID NO: 23 |
| Exon 21 reverse inside | GCTGGCTGACCTAAAGCCACC | SEQ ID NO: 24 |

Notes
*Similar to patient 1 in (11)
†Similar to the Del-1b (12)
‡Patient 38 predominantly mutant.
Patient 3 mutation has not been reported in SNP database.

The inventors also compared associations between EGFR mutation status, FISH status, and level of protein expression in each tumor with patient outcome. EGFR mutations were statistically significantly associated with FISH+ status (P=0.01), but not with high protein expression (P=0.10). Gene mutations were statistically significantly associated with better response (54% versus 5%, mean difference 47.9%, 95% CI: 22.2 to 73.7, P<0.001) and longer time to progression (9.9 versus 2.6 months, mean difference 7.3 months, 95% CI: 2.1 to 16.7 months, P=0.02) (Table 7). Patients with EGFR mutations had better survival, although it was not statistically significant (median 20.8 versus 8.4 months, mean difference 12.4 months, 95% CI: 1.7 to 26.4 months, P=0.09). However, six of the 15 patients with mutations (40%), five of whom carried point mutations in exon 21 (patients 1, 2, 3, 16, and 100; Tables 9 and 10) and one of whom had an exon 19 deletion (patient 41, Tables 9 and 10) had progressive disease. Among the eight patients with EGFR mutations responding to the treatment, seven were also FISH+, whereas four of six progressing patients with mutations were FISH− (disomy, Table 10). Moreover, among the 21 patients with stable disease, only one presented EGFR mutations.

TABLE 10

Epidermal growth factor receptor (EGFR) and phosphorylated (P)-Akt protein levels and outcome for non-small-cell lung cancer patients presenting EGFR mutation or gene amplification*

| Patient | EGFR Gene Amplification | EGFR Gene Mutation | EGFR IHC | P-Akt | Response | Time to Progression, months | Overall Survival, months |
|---|---|---|---|---|---|---|---|
| 1 | − | L858R | − | + | PD | 2.11 | 2.11 |
| 2 | − | L858R | + | − | PD | 2.18 | +5.3 |
| 3 | − | V852I | + | + | PD | 4.05 | 4.05 |
| 4 | + | ND | − | + | PD | 2.2 | 2.73 |
| 12 | + | none | − | + | SD | 5.99 | 8.32 |
| 15 | + | Exon 19 del | + | + | PR | +5.33 | +5.33 |
| 16 | − | L858R | + | − | PD | 1.61 | 3.16 |
| 19 | + | Exon 19 del | − | + | PR | 9.18 | +18.9 |
| 26 | − | L858R | + | + | PR | 13.6 | +26.2 |
| 30 | − | Exon 19 del | + | + | SD | 9.87 | 11.5 |
| 31 | + | L858R | + | + | PR | +17.4 | +17.4 |
| 37 | + | none | + | + | PD | 2.66 | 4.05 |
| 38 | + | L858R | + | + | CR | 19.7 | 20.8 |
| 41 | − | Exon 19 del | − | + | PD | 2.89 | 5.72 |
| 51 | + | ND | + | + | SD | 7.7 | +8.75 |
| 53 | + | Exon 19 del | + | + | PR | +20.7 | +20.7 |
| 57 | − | Exon 19 del | + | + | PR | 11.3 | +12.2 |
| 75 | + | Exon 19 del | + | + | PR | 15.6 | +30.2 |
| 91 | + | ND | + | + | SD | 5.16 | 8.098 |
| 100 | − | L858R | − | ND | PD | 1.55 | 2.86 |
| 101 | + | ND | + | + | PR | 9.05 | 10.3 |
| 102 | + | none | + | + | PD | 3.22 | 3.95 |

*Characteristics of 102 patients with histologically confirmed non-small-cell lung cancer with measurable, locally advanced or metastatic disease, progressing or relapsing after chemotherapy, or medical contraindications for chemotherapy who were subsequently treated with 250 mg gefitinib daily. ND: not determined; PD = progressive disease, SD = stable disease, PR = partial response; CR = complete response. IHC = immunohistochemistry. EGFR gene amplification+ = Presence of gene amplification. EGFR gene amplification− = Absence of amplification. EGFR IHC+ = Positive. EGFR IHC− = Negative. P-Akt+ = Positive. P-Akt− = Negative. Time to progression and survival+ = Censored EGFR Multivariable Analysis To define which variables were predictive for survival, those factors that were significant in the univariate analysis (sex, histology, performance status, FISH, and protein status) were included in a multivariable model. Mutation and smoking status were not included because they were not associated with survival (P=0.09 and P=0.20, respectively) in univariate analyses. Poor performance status (PS 2) remained statistically significantly associated with increased risk of death (hazard ratio [HR]=3.27, 95% CI=1.49 to 7.17, P=0.003), whereas adenocarcinoma/bronchioloalveolar histologies (HR=0.58, 95% CI=0.35 to 0.96, P=0.035) and FISH status (HR=0.44, 95% CI=0.23 to 0.82, P=0.01) were statistically significantly associated with better survival. Protein status (HR=0.60, 95% CI=0.36 to 1.01, P=0.056) and sex (HR=1.43, 95% CI=0.79 to 2.6, P=0.20) were not statistically significantly associated with survival.

Association Between EGFR and P-Akt

Evaluation of the P-Akt protein was successful in 98 patients. P-Akt positive status was significantly associated with better response rate (21% versus 0%, mean difference 20.6%, 95% CI: 11.0 to 30.2, P=0.004), disease control rate (50% versus 22%, mean difference 28.1%, 95% CI: 9.5 to 46.7, P=0.008), longer time to progression (4.2 versus 2.1 months, mean difference 2.1 months, 95% CI: 0.7 to 3.4 months, P=0.01), but not with survival (11.4 versus 9.4 months, mean difference 2.0 months, 95% CI: 1.3 to 5.3 months, P=0.20). P-Akt positive status was also significantly associated with EGFR gene gain (FISH+ Pearson r=0.30, P=0.01) and high level of protein expression (EGFR IHC+ Pearson r=0.27, P=0.01), but not with EGFR mutation (P=0.08).

Combining FISH and P-Akt data (Table 11), the inventors observed that double positive patients (EGFR FISH+/P-Akt+) had a significantly higher response rate (41% versus 3%, mean difference 38.5%, 95% CI: 20.1 to 56.8, P<0.001) and disease control rate (72% versus 28%, mean difference 44.9%, 95% CI: 26.6 to 65.3, P <0.001), longer time to progression (9.0 versus 2.5 months, mean difference 6.5 months, 95% CI: 3.3 to 9.8 months, P<0.001) and survival (18.7 versus 9.4 months, mean difference 9.3 months, 95% CI: 4.7 to 13.9 months, P=0.04) compared with patients EGFR FISH− and/or P-Akt− patients. Similar findings were observed when EGFR immunohistochemistry and mutation data were combined with P-Akt data. Compared with EGFR− and/or P-Akt− patients, EGFR IHC+/P-Akt+ patients had a significantly better response rate (29% versus 4%, mean difference 25.8%, 95% CI: 10.9 to 40.4, P<0.001), disease control rate (66% versus 23%, mean difference 43.1%, 95% CI: 23.9 to 60.6, P<0.001), longer time to progression (6.2 versus 2.3, mean difference 3.9 months, 95% CI: 1.5 to 6.3 months, P=0.001), and longer survival (14.9 versus 8.3 months, mean difference 6.6 months, 95% CI: 4.0 to 9.2 months, P=0.03). EGFR mutation+/P-Akt+ patients had a statistically significantly better response rate (67% versus 6%, mean difference 61.2%, 95% CI: 34.0 to 88.4, P<0.001), disease control rate (75% versus 32%, mean difference 43.5%, 95% CI: 16.8 to 70.2, P=0.008), longer time to progression (11.2 versus 2.6 months, mean difference 8.6 months, 95% CI: 3.3 to 14.0 months, P=0.004), and longer survival (20.8 versus 9.3 months, mean difference 11.5 months, 95% CI: 1.1 to 24.2 months, P=0.044) than EGFR mutation− and/or P-Akt− patients.

TABLE 11

Association between epidermal growth factor receptor (EGFR) fluorescence in situ hybridization (FISH), immunohistochemistry (IHC), and mutation with phosphorylated (P)-Akt in non-small-cell lung cancer patients*

| Markers | No. of Patients/% | Objective Response, N/% | Disease Control Rate, N/% | Median Time to Progression, months | Median Survival, months | 1-year Cumulative Survival ± SD, % |
|---|---|---|---|---|---|---|
| EGFR FISH/P-Akt | 98/100 | 14/14 | 40/40 | 4.5 | 11.5 | 47 ± 6 |
| EGFR FISH+/P-Akt+ | 29/30 | 12/41 | 21/72 | 9.0 | 18.7 | 33 ± 9 |
| EGFR FISH+/P-Akt− | 4/4 | 0 | 1/25 | 1.1 | 13.8 | 75 ± 22 |
| EGFR FISH−/P-Akt+ | 38/39 | 2/5 | 12/32 | 2.6 | 8.4 | 38 ± 8 |
| EGFR FISH−/P-Akt− | 27/28 | 0 | 6/22 | 2.4 | 6.0 | 57 ± 9 |
| Any Negative | 69/70 | 2/3 | 19/27 | 2.5 | 9.4 | 37 ± 6 |
| P (Any-versus +/+) | | <.001§ | <.001‡ | <.001† | .041† | .075† |
| EGFR IHC/P-Akt | 98/100 | 14/14 | 40/40 | 3.2 | 11.3 | 45 ± 6 |
| EGFR IHC+/P-Akt+ | 41/42 | 12/29 | 27/66 | 6.2 | 14.9 | 29 ± 14 |
| EGFR IHC+/P-Akt− | 17/17 | 0 | 5/29 | 1.8 | 9.4 | 35 ± 12 |
| EGFR IHC−/P-Akt+ | 26/27 | 2/8 | 7/27 | 2.3 | 6.4 | 38 ± 10 |
| EGFR IHC−/P-Akt− | 14/14 | 0 | 1/7 | 2.0 | 4.2 | 54 ± 8 |
| Any negative | 57/58 | 2/3 | 13/23 | 2.3 | 8.3 | 35 ± 7 |
| P (Any-versus +/+) | | <.001‡ | <.001‡ | .001† | .029† | .032† |
| EGFR Mutation/P-Akt | 85/100 | 12/14 | 32/38 | 2.9 | 10.1 | 43 ± 5 |
| EGFR Mutation+/P-Akt+ | 12/14 | 8/67 | 9/75 | 11.2 | 20.8 | 38 ± 10 |
| EGFR Mutation+/P-Akt− | 2/2 | 0 | 0 | 1.1 | 3.1 | 40 ± 7 |
| EGFR Mutation−/P-Akt+ | 44/52 | 4/9 | 17/39 | 2.7 | 8.4 | 50 ± 35 |
| EGFR Mutation−/P-Akt− | 27/32 | 0 | 6/22 | 2.4 | 9.4 | 65 ± 14 |
| Any Negative | 73/86 | 4/5 | 23/31 | 2.6 | 9.3 | 39 ± 6 |
| P (Any-versus +/+) | | <.001§ | .008§ | .004§ | .044† | .116† |

*Characteristics of 102 patients with histologically confirmed non-small-cell lung cancer with measurable, locally advanced or metastatic disease, progressing or relapsing after chemotherapy, or medical contraindications for chemotherapy who were subsequently treated with 250 mg gefitinib daily.
†P values (two-sided) calculated using the log-rank test.
‡P values (two-sided) calculated using Pearson's chi-square test.
§P values (two-sided) calculated using Fisher's exact test.

Independent of the method of EGFR assessment, patients who were EGFR positive and P-Akt negative did not respond to gefitinib treatment (Table 11). The group of patients EGFR IHC+/P-Akt− had a significantly worse outcome than the group positive for both proteins, in terms of response rate (0% versus 29%, mean difference 29.3%, 95% CI: 15.3 to 43.2, P=0.012), disease control rate (29% versus 66%, mean difference 36.5%, 95% CI: 10.4 to 62.5, P=0.011), and had a not significant tendency toward shorter time to progression (1.8 versus 6.2 months, mean difference 4.4 months, 95% CI: 2.3 to 6.4 months, P=0.08) and survival (9.4 versus 14.9 months, mean difference 5.5 months, 95% CI: 1.6 to 9.3 months, P=0.21). No comparisons were made with EGFR FISH and EGFR mutation because of the small number of patients (i.e. 4 and 2, respectively) in the group positive for EGFR and negative for P-Akt.

Unfavorable outcomes were also observed in the group of patients negative for EGFR but positive for P-Akt (Table 11). Compared with the double positive group, the EGFR FISH−/P-Akt+ group had a statistically significant worse response rate (5% versus 41%, mean difference 36.1%, 95%

CI: 16.8 to 55.4, P<0.001), disease control rate (32% versus 72%, mean difference 40.8%, 95% CI: 18.9 to 62.8, P=0.001), and time to progression (2.6 versus 9.0 months, mean difference 6.4 months, 95% CI: 3.7 to 9.1 months, P=0.001) and a non-statistically significant shorter survival (8.4 versus 18.7 months, mean difference 10.3 months, 95% CI: 7.2 to 13.4 months, P=0.083). Similar findings were observed when EGFR was evaluated by immunohistochemistry or for mutations. In both cases, the EGFR−/P-Akt+ group had a statistically significantly worse response rate (P=0.034 and P<0.001, respectively, for protein and mutation), disease control rate (P=0.002 and P=0.025), time to progression (P=0.010 and P=0.009) and had a non-statistically significant worse survival (P=0.080 and P=0.070), compared with the double positive group.

Discussion

In this study, the inventors have shown that EGFR protein expression was associated to improved response rate, statistically significant prolonged time to progression and survival. Patients with low IHC scores (<200) had an outcome as poor as those with low gene copy numbers or lacking mutations. In addition, in patients with positive EGFR status by any means, the presence of Akt phosphorylation was significantly related to better response, disease control rate, time to progression, and survival. The results indicate that high EGFR protein expression is an effective molecular predictive marker for gefitinib sensitivity in patients with advanced NSCLC.

The presence of EGFR gene mutations was also related to better response to gefitinib and time to progression, but the difference in survival did not reach statistical significance. An interesting finding was the association between EGFR mutations and increased gene copy number, a phenomenon that was recently described in the human lung cancer cell line H3255 (Tracy et al., *Cancer Res,* 2004; 64:7241-44) and that is probably relevant to gefitinib sensitivity. In fact, among the eight patients with EGFR mutations who responded to gefitinib therapy, seven were also FISH+, and among the six non-responding patients with EGFR mutations, four presented a disomic pattern. This observation suggests that the impact of genomic gain is critical for EGFR mutations to predict gefitinib sensitivity.

Another important finding from these studies was the virtual absence of EGFR mutations in patients with stable disease. Among the 21 patients with stable disease who were assessed for EGFR mutations, only one patient had an EGFR mutation. Stable disease was defined here as neither sufficient shrinkage to qualify for partial response, nor sufficient increase to qualify for progressive disease, as confirmed by two consecutive observations no less than 4 weeks apart. The small number of mutations in patients with stable disease is of clinical relevance because data from the BR.21 trial (Shepherd et al., 2004) show that the survival benefit of gefitinib is not confined to responding patients. It is possible that survival improvement in the gefitinib-treated patients, as a whole, is due to the presence of a group of patients with an intermediate benefit from the treatment, such as those with stable disease, who would be excluded from tyrosine kinase inhibitor treatment if mutation analysis were established as the test of choice for patient selection. Moreover, although previous studies suggested that EGFR mutations are present in the vast majority of responding patients (Lynch et al., 2004; Paiez et al., 2004; Pao et al., 2004), in this study, the inventors observed that 40% of patients with EGFR mutations had progressive disease. These results could be explained by the fact that this is the first study conducted in a large and unselected cohort of gefitinib treated patients, in whom clinical results are similar to those obtained in large clinical trials with gefitinib (Fukuoka et al., 2003; Kris et al., 2003, *JAMA*).

In this study, gefitinib sensitivity was associated with high EGFR protein expression; outcomes in patients with low EGFR expression scores (<200) were as poor as those in patients with low gene copy numbers or lacking mutations, which is different from what has been observed in previous studies (Cappuzzo et al., 2003, *J. Clin. Oncol.*; Bailey et al., 2003; Parra et al., 2004). Differences in staining procedures and guidelines for interpretation of the EGFR assessment may be the major reason for the conflicting results across studies. The sampling size and selection of tissue material for immunohistochemical staining might also contribute to differences in results across the studies. For instance, tumors from only 43 and 50 patients were evaluated by Cappuzzo et al. (Cappuzzo et al., 2003, *J. Clin. Oncol.*) and Parra et al. (Parra et al., 2004), respectively. In the retrospective immunohistochemical analysis of tumor tissue from the IDEAL trials, less than 40% of the total population of patients were studied (Bailey et al., 2003), whereas in the present study, more than 90% of patients had tissue available for immunohistochemical staining.

In this study, the inventors also found an association between activated Akt pathway (e.g. expression of phosphorylated Akt) and gefitinib sensitivity, an association that has also been described and discussed by others (Sordella et al., 2004; Cappuzzo et al., 2004, *J. Natl. Cancer Inst.*). The combinatorial analysis of EGFR and P-Akt status indicated that, independent of the method of EGFR assessment, when EGFR status was positive, the presence of Akt phosphorylation was significantly related to better response, disease control rate, time to progression, and survival. Importantly, better outcome was observed not only when the subset of EGFR+/P-Akt+ patients was compared with all the other groups combined but also when this subset was compared with patients EGFR positive but P-Akt negative. These findings support the hypothesis that, when the gefitinib target is present but the anti-apoptotic pathway is not activated, the patient is not sensitive to the inhibitory effects of gefitinib, as suggested previously (Cappuzzo et al., 2004, *J. Natl. Cancer Inst.*) and as demonstrated in preclinical models (Ono et al., 2004; Bianco et al., 2003). As expected, the EGFR+/P-Akt+ group also had a significantly better outcome compared with the EGFR negative and P-Akt positive group, confirming preclinical data indicating that aberrant, EGFR-independent Akt activation may lead to gefitinib resistance (Bianco et al., 2003; Janmaat et all, 2003). These data indicate that P-Akt positive status is relevant in EGFR-positive patients for the identification of a subgroup of patients particularly sensitive to the drug. In EGFR-negative patients, P-Akt positive status may identify a group of patients with a very low chance of benefiting from gefitinib treatment.

Information regarding the relationship between EGFR protein expression and Akt pathway activation would greatly advance the understanding of the mechanisms of gefitinib sensitivity. The inventors compared EGFR protein and P-Akt expression in a subgroup of patients and, in general, expression of EGFR and P-Akt proteins was found in the same cell populations (data not shown), indicating that the observed P-Akt was a result of EGFR activity. However, in some cases discrepancies were found in the expression (i.e., some cells expressed EGFR and not P-Akt and vice versa.), which may be due to biological causes or technical causes.

In conclusion, results from this study demonstrate that gefitinib is effective in advanced NSCLC patients with high EGFR protein expression and combinations of EGFR protein/mutation, EGFR protein/FISH. IHC represents an ideal test for selecting candidate NSCLC patients for gefitinib therapy. Because patients who had either high EGFR expression and P-Akt had a better response, disease control rate, time to progression, and survival, analysis of the activating status of the Akt protein is also believed to be relevant for proper patient selection.

Example 4

The following example summarizes results of studies demonstrating the use of HER2 gene amplification and HER2 polysomy to predict outcome to EGFR inhibitors in NSCLC patients (Italian cohort).

In these experiments, HER2 gene copy numbers per cell were measured by FISH, HER2 protein levels were measured by immunohistochemistry and mutations in HER2 exon 20 were evaluated in a cohort of 102 advanced stage NSCLC patients treated with gefitinib.

Results and Conclusions

HER2 FISH analysis was completed in 102 patients. Patients with HER2 high copy number (high polysomy and gene amplification: HER2 FISH+) represented 22.8% of cases and compared with patients with no or low gain (HER2 FISH−) had significantly better objective response (OR: 34.8% versus 6.4%, p=0.001), disease control rate (DCR: 56.5% versus 33.3%, p=0.04), time to progression (TTP: 9.05 versus 2.7 months, p=0.02) and a trend toward longer survival (OS: 20.8 versus 8.4 months, p=0.056).

HER2 protein expression was investigated in 72 patients and 5 (7%) patients were positive for high level of HER2 expression. No significant association was detected with response or survival in this cohort but the ultimate clinical role of HER2 protein expression in relation to tyrosine kinase inhibitors needs to be investigated in a larger study population.

Exon 20 of the HER2 gene was sequenced in 89 patients and all were negative for mutations. Therefore, mutations in the tyrosine kinase domain of the HER2 gene seem to be infrequent and not clinically relevant.

In conclusion, this study showed that patients with HER2 FISH+ NSCLC have clinical benefit from the TKI gefitinib treatment, represented by higher response rate, disease control rate and longer time to progression.

Example 5

The following example summarizes results of studies demonstrating the use of HER2 gene amplification and polysomy together with EGFR gene amplification and polysomy to predict outcome to EGFR inhibitors in NSCLC patients) Italian cohort).

In this study, HER2 FISH pattern analysis was combined with EGFR FISH pattern analysis, using the methodology previously described herein.

Results showed that patients with HER2 FISH+/EGFR FISH+ tumors had a significantly better OR and DCR than patients negative for both receptors. Patients with high copy number of both genes (HER2 FISH+/EGFR FISH+) had the highest OR (53.8%) and DCR (76.9%), and these results were significantly better than those observed in patients with HER2 FISH− and/or EGFR FISH− tumors (OR: 6.8%, p<0.001; DCR: 33.0%, p=0.002). The HER2 FISH+/EGFR FISH− patients had lower OR than double positive patients, although the difference was not statistically significant (OR: 21.0%, p=0.07). No difference response was observed between HER2 FISH−/EGFR FISH+ patients and the double negative HER2 FISH−/EGFR FISH− patients (OR: 10.0% versus 1.6%, p=0.27; DCR: 30.0% versus 25.4%, p=0.71), although the latter group had a significantly worse outcome when compared to HER2 FISH+ and/or EGFR FISH+ (OR: 1.6% versus 28.6%, p<0.001; DCR: 25.4 versus 57.1%, p=0.001).

Patients with HER2 FISH+/EGFR FISH+ tumors had a significantly longer time to progression and overall survival than patients negative for both receptors. In the double positive HER2 FISH+/EGFR FISH+ patients, the median TTP and OS were 9.8 and 20.8 months, respectively, significantly longer than those observed in the HER2 FISH− and/or EGFR FISH− groups (TTP: 2.6 months, p=0.007; OS: 8.3 months, p=0.04), and with a non significant trend when compared to the HER2 FISH−/EGFR FISH+ patients (TTP: 5.3 months, p=0.20; OS:9.3 months, p=0.13). Patients with HER2 FISH+/EGFR FISH− tumors had the same poor outcome as the double negative group (TTP: 2.3 versus 2.6 months, p=0.4, OS: 6.0 versus 7.3 months, p=0.4).

Example 6

The following example summarizes the results of studies demonstrating the use of HER2 gene amplification and HER2 polysomy together with detection of EGFR protein levels to predict outcome to EGFR inhibitors in patients with NSCLC tumors.

In these studies, HER2 FISH pattern was combined with EGFR protein expression determined by immunohistochemistry (IHC), using the methodology described previously herein.

Patients with HER2 FISH+/EGFR IHC+ tumors had significantly better OR and DCR than patients negative for both receptors. OR and DCR were significantly better in double positive HER2 FISH+/EGFR IHC+ patients when compared to all other groups of patients (OR: 53.8% versus 7.1%, p<0.001; DCR: 76.9 versus 34.5, p=0.004). Significant difference in OR was observed between double positive and HER2 FISH−/EGFR IHC+ patients (OR: 11.1%, p=0.003). No difference was found between HER2 FISH+/EGFR IHC− and double negative HER2 FISH−/EGFR IHC− patients, in which OR and DCR were significantly worse than in the other three groups combined (OR: 0% versus 19.1%, p=0.009; DCR: 13.7% versus 51.5%, p=0.001).

Patients with HER2 FISH+/EGFR IHC+ tumors also had a significantly longer time to progression and overall survival than patients negative for both receptors. TTP and survival were significantly longer in double positive patients (HER FISH+/EGFR IHC+) when compared with the other three group of patients combined (HER2 FISH− and/or EGFR IHC−; TTP: 12.3 versus 2.6 months, p=0.006; OS: 20.8 versus 8.4 months, p=0.030) and with a statistically significant longer TTP and trend toward better survival when compared to patients with HER2 FISH−/EGFR IHC+ tumors (TTP: 4.2 months, p=0.046; OS: 11.3, p=0.12). The patients with HER2 FISH+/EGFR IHC− tumors had similarly poor outcome than the double negative group (TTP: 2.3 versus 2.1 months, p=0.06; OS: 3.3 versus 5.0 months, p=0.39).

Example 7

The following example summarizes the results of studies demonstrating the use of HER2 gene amplification and HER2 polysomy together with detection of mutations in the EGFR gene to predict outcome to EGFR inhibitors in patients with NSCLC tumors.

In this example, HER2 FISH pattern was combined with presence of mutations in the EGFR gene determined by DNA sequencing, using the methodology described previously herein.

Patients with HER2 FISH+/EGFR mutation+ tumors had the best OR and DCR (87.5% for both), which were significantly higher than in patients HER2 FISH− and/or EGFR mutation− (OR: 5.0%, p<0.001; DCR: 31.3%, p=0.003). Among the 7 HER2 FISH−/EGFR mutation+ patients, a single patient responded (OR: 14.2%) and a single patient had disease stabilization (DCR: 28.5%). In the HER2 FISH+/EGFR mutation− group, no patient responded and DCR was 27.2%. These results were not different than those observed in double negative HER2 FISH−/EGFR mutation− patients (OR: 4.8%, p=1.0; DCR: 32.2%, p=1.0), in whom OR was significantly worse than in the other groups combined (OR: 30.8%, p=0.002).

Patients with HER2 FISH+/EGFR mutation+ tumors had a significantly longer TTP and OS when compared to other patients combined (TTP: 15.5 versus 2.6 months, p=0.003; OS: not reached versus 8.3, p=0.001), but also when compared to patients HER2 FISH−/EGFR mutation+ (TTP: 2.8 months, p=0.004; OS: 5.7, p=0.030). The group of patients EGFR mutation−/HER2 FISH+ had the worst outcome in terms of TTP (2.3 months) and OS (6.5 months).

Example 8

Based on studies combining the Italian study cohort and the Southwest Oncology Group study 0126 further support of the predictive role of the individual test as well as combinations of tests is given:
(1) Support of Increased EGFR Gene Copy Number as Predictive Marker for Clinical Effect from EGFR Inhibitors in NSCLC Patients The University of Colorado Cancer Center has performed laboratory analysis from two clinical trials. In order to make a more substantial statistical analysis and power, the inventors have analyzed the combined data set, which includes altogether 204 patients with NSCLC. One trial from Italy (102 patients), in which patients with advanced non-small cell lung cancer (NSCLC) have been treated with gefitinib 250 mg daily after failure of at least one prior chemotherapy regimen. The other clinical trial is performed by the Southwest Oncology Group (SWOG) in 136 patients with bronchioloalveolar carcinoma (BAC) or adenocarcinoma with BAC features. Tables 12 and 13 show the characterization of the combined patients and EGFR IHC, EGFR FISH, EGFR mutation, phosphorylated Akt and KRas status.

TABLE 12

|  | Italian Cohort | S0126 Cohort | Total |
|---|---|---|---|
| Male | 68 (65%) | 48 (48%)* | 116 (57%) |
| Female | 36 (35%) | 52 (52%) | 88 (43%) |
| Current/Former Smokers | 89 (86%) | 73 (73%)* | 162 (79%) |
| Never Smoked | 15 (14%) | 27 (27%) | 42 (21%) |
| Performance Status 0-1 | 91 (87%) | 86 (86%) | 177 (87%) |
| Performance Status 2 | 13 (13%) | 14 (14%) | 27 (13%) |
| Adenocarcinoma | 55 (53%) | 44 (45%) | 99 (49%) |
| BAC | 9 (9%) | 54 (55%) | 63 (31%) |
| Large Cell | 2 (2%) |  | 2 (1%) |
| Squamous Cell | 26 (25%) |  | 26 (13%) |
| Undifferentiated | 12 (12%) |  | 12 (6%) |
| Stage III Disease | 14 (13%) | 7 (7%) | 21 (11%) |
| Stave IV Disease | 90 (87%) | 89 (93%) | 179 (89%) |
| Overall Response | 13% | 17% | 15% |
| Disease Control Rate | 39% | 48% | 43% |
| Median Time to Progression | 3 (2-4) | 4 (3-6)* | 3 (3-4) |
| Median Survival | 9 (6-11) | 14 (10-18)* | 11 (8-14) |
| One-YR Survival | 41% (31-51) | 55% (45-64) | 48% (41-55) |

*p < 0.055

TABLE 13

|  | EGFR IHC+ | EGFR IHC− | EGFR FISH+ | EGFR FISH − | EGFR M+ | EGFR M− | PAKT+ | PAKT− | KRAS+ | KRAS− |
|---|---|---|---|---|---|---|---|---|---|---|
| Male | 68/121 (56%) | 45/79 (57%) | 30/59 (51%) | 77/124 (62%) | 18/43 (42%) | 72/113 (64%) | 72/127 (57%) | 30/57 (53%) | 25/36 (69%) | 58/102 (57%) |
| Female | 53/121 (44%) | 34/79 (43%) | 29/59 (49%) | 47/124 (38%) | 25/43 (58%) | 41/113 (36%) | 55/127 (43%) | 27/57 (47%) | 11/36 (31%) | 44/102 (43%) |
|  | Chi Square p-value = 0.915 | | Chi Square p-value = 0.149 | | Chi Square p-value = 0.014 | | Chi Square p-value = 0.608 | | Chi Square p-value = 0.185 | |
| Current/Former Smokers | 99/121 (82%) | 59/79 (75%) | 42/59 (71%) | 104/124 (84%) | 30/43 (70%) | 96/114 (84%) | 26/127 (20%) | 12/57 (21%) | 33/36 (92%) | 80/102 (78%) |
| Never Smoked | 22/121 (18%) | 20/79 (25%) | 17/59 (29%) | 20/124 (16%) | 13/43 (30%) | 18/114 (16%) | 101/127 (80%) | 45/57 (79%) | 3/36 (8%) | 22/102 (22%) |
|  | Chi-square p-value = 0.226 | | Chi-square p-value = 0.046 | | Chi-square p-value = 0.045 | | Chi Square p-value = 0.928 | | Chi Square p-value = 0.076 | |
| Adenocarcinoma | 58/120 (48%) | 38/78 (49%) | 31/58 (53%) | 54/124 (44%) | 24/42 (57%) | 58/112 (52%) | 59/126 (47%) | 26/57 (46%) | 21/36 (58%) | 45/101 (45%) |

TABLE 13-continued

| | EGFR IHC+ | EGFR IHC− | EGFR FISH+ | EGFR FISH − | EGFR M+ | EGFR M− | PAKT+ | PAKT− | KRAS+ | KRAS− |
|---|---|---|---|---|---|---|---|---|---|---|
| BAC | 36/120 (30%) | 27/78 (35%) | 15/58 (26%) | 43/124 (35%) | 13/42 (31%) | 27/112 (24%) | 43/126 (34%) | 19/57 (33%) | 14/36 (39%) | 29/101 (29%) |
| Large Cell | 1/120 (1%) | 1/78 (1%) | 1/58 (2%) | 1/124 (1%) | 0/42 (0%) | 1/112 (1%) | 1/126 (1%) | 1/57 (2%) | 0/36 (0%) | 1/101 (1%) |
| Squamous Cell | 18/120 (15%) | 8/78 (10%) | 9/58 (16%) | 17/124 (14%) | 2/42 (5%) | 19/112 (17%) | 17/126 (13%) | 8/57 (14%) | 1/36 (3%) | 18/101 (18%) |
| Undifferentiated | 7/120 (6%) | 4/78 (5%) | 2/58 (3%) | 9/124 (7%) | 3/42 (7%) | 7/112 (6%) | 6/126 (5%) | 3/57 (5%) | 0/36 (0%) | 8/101 (8%) |
| | Chi-square p-value = 0.867 | | Chi-square p-value = 0.536 | | Chi-square p-value = 0.347 | | Chi Square p-value = 0.984 | | Chi Square p-value = 0.051 | |

As shown in Table 14 (see below), in the study 183 patients had FISH analysis performed, and 52 patients (32%) were EGFR "FISH-positive" (had high polysomy or gene amplification). The "overall response" rate was 33% for the FISH-positive group versus 6% for the FISH-negative (disomy, trisomy and low polysomy) group (p<0.001). The "disease control" rate (objective response+stable disease) was 65% in the FISH positive group versus 30% in the FISH negative group (p<0.001). Time to progression (TTP) was in median 9 months (95% CI 5-10) for the FISH positive group versus 3 months (95% CI 2-3) for the FISH negative group (p<0.001). Median survival was 18 months (95% CI 14-21) in the FISH positive group versus 8 months (95% CI 6-11) in the FISH negative group (p=0.002) and 1 year survival rate was 68% (95% CI 56-80%) in the FISH positive group versus 37% (95% CI 29-46%) in the FISH negative group.

In conclusion this combined data analysis demonstrated statistically significant better response, disease control, time to progression and survival for patients with increased EGFR gene copy number ("FISH-positive") compared to FISH-negative patients. These analyses which now include 183 patients support the individual results from the Italian study cohort (Cappuzzo et al., 2005 JNCI) and the Southwest Oncology Group Study (Hirsch et al., JCO in press 2005).

(2) Support of EGFR Protein Expression Detected by Immunohistochemistry as a Predictive Marker for Clinical Effect of EGFR Inhibitors in NSCLC Patients.

As shown in Table 14, EGFR protein expression was measured in 203 patients by immunohistochemistry. EGFR protein was considered positive in 121 patients (61%). The overall response in the EGFR-positive patients was 22% versus 5% in the EGFR-negative group (p=0.002) and disease control rate was 56% versus 27% (p<0.001). Time to progression was 5 months (95% CI 3-7) versus 3 months for the EGFR negative patients (p=0.006), and median survival was 14 months (95% CI 11-21) versus 7 months (5-10) (p=0.003). One year survival rates were 56% (95% CI 47-65%) for the EGFR positive group versus 37% (26-48%) for the EGFR negative group.

In conclusion, EGFR protein expression determined by immunohistochemistry predicted significant better response, disease control rate, median survival and 1-year survival after treatment with EGFR inhibitor compared to the EGFR-negative group of patients.

TABLE 14

| | No. pts | OR | DC | TTP | MS | 1-yr OS |
|---|---|---|---|---|---|---|
| FISH+ | 59 (32%) | 33% | 65% | 9 (5-10) | 18 (14-21) | 68% (56%-80%) |
| FISH− | 124 (68%) | 6% | 30% | 3 (2-3) | 8 (6-11) | 37% (29%-46%) |
| | | p-value <0.001 | p-value <0.001 | p-value <0.001 | p-value = 0.002 | |
| IHC+ | 121 (61%) | 22% | 56% | 5 (3-7) | 14 (11-21) | 56% (47%-65%) |
| IHC− | 79 (40%) | 5% | 27% | 3 (2-3) | 7 (5-10) | 37% (26%-48%) |
| | | p-value = 0.002 | p-value <0.001 | p-value = 0.006 | p-value = 0.003 | |
| EGFR Mutation+ | 43 (28%) | 39% | 52% | 3 (2-11) | 13 (6-21) | 52% (37%-68%) |
| EGFR Mutation− | 113 (72%) | 7% | 37% | 3 (2-4) | 11 (7-13) | 46% (37%-55%) |
| | | p-value <0.001 | p-value = 0.151 | p-value = 0.180 | p-value = 0.210 | |
| P-AKT+ | 127 (69%) | 20% | 49% | 4 (3-5) | 13 (10-16) | 52% (43%-61%) |
| P-AKT− | 57 (31%) | 2% | 33% | 3 (2-5) | 8 (6-14) | 41% (28%-54%) |
| | | p-value = 0.005 | p-value = 0.10 | p-value = 0.09 | p-value = 0.34 | |
| KRAS Mutation+ | 36 (26%) | 7% | 39% | 3 (2-4) | 11 (6-23) | 49% (33%-66%) |
| KRAS Mutation− | 102 (74%) | 19% | 40% | 3 (2-4) | 12 (8-15) | 50% (40%-60%) |
| | | p-value = 0.237 | p-value = 0.99 | p-value = 0.890 | p-value = 0.890 | |

(3) Combination of EGFR Protein Assessment by Immunohistochemistry and EGFR Gene Copy Number by FISH Strongly Predict Good Outcome After EGFR Inhibitor Therapy, and Patients with "Negative" Results for Both EGFR Protein and EGFR Gene Copy Number by FISH Can be Used to Select Lung Cancer Patients Who Will Not Have Any Clinical Benefit From EGFR Inhibitors in NSCLC Patients From the combined data analysis came two clear results:

As shown in Table 15, among 42 patients who were both "EGFR FISH-positive" and "EGFR IHC-positive", the response rate was high, 41%, and 76% had disease control. The time to progression for the "double positive" group of patients was 9 months (95% CI 6-16 months), median survival was 21 months (95% CI 15-21) and 1-year survival was 77% (95% CI 63-90). In contrast, the corresponding values for the "double negative" group of patients (patients with "EGFR FISH negative" and "EGFR IHC-negative") was response rate of 2%, disease control rate of 17%, time to progression was 2 months, median survival was 6 months and 1-year survival was 30%. There was statistical significance difference (p<0.001) in all parameters.

TABLE 15

Combined FISH and IHC results (n = 179 patients)

|  | No. pts | RSP | DCR | TTP (mo) | MS (mo) | 1-yr |
|---|---|---|---|---|---|---|
| FISH+/IHC+ | 42 | 41% | 76% | 9 (6-16) | 21 (15-21) | 77% (63-90) |
|  |  | p-value* <0.001 | p-value* <0.001 | p-value* <0.001 | p-value* <0.001 |  |
| FISH+ or IHC+ | 83 | 10% | 43% | 3 (2-5) | 11 (7-15) | 44% (33-55) |
| FISH−/IHC− | 54 | 2% | 17% | 2 (2-3) | 6 (4-8) | 30% (18-43) |

*p-value of FISH+/IHC+ versus other two groups

In conclusion, lung cancer patients, whose tumors strongly express both EGFR protein (detected by immunohistochemistry) and increased EGFR gene copy number (detected by FISH) have a high response rate, disease control rate and significantly prolonged survival after EGFR inhibitor therapy compared to patients with "double negative" assessments.

Patients with NSCLC, who tested "double negative" (no/low EGFR protein overexpression and no/low gain of the EGFR gene) will most likely not benefit from EGFR inhibitor therapy and should not be offered this therapy.

Thus, the combination of EGFR FISH− and IHC assay should be used to select NSCLC patients who will benefit and those without any expected clinical benefit from EGFR therapy.

(4) Combination of EGFR Mutation and EGFR Protein Expression

As shown in Table 16, among 28 patients with positive test both for EGFR mutation and EGFR protein expression the response rate for the patients with double positive test was 50%, disease control rate was 60%, time to progression was 10 months, median survival was 21 months and 1-year survival was 63%. Corresponding values for patients with double negative test was 12%, 25%, 2 months, 7 months and 37%.

TABLE 16

Combined EGFR mutation and IHC results (n = 152 patients)

|  | No. pts | RSP | DCR | TTP (mo) | MS (mo) | 1-yr |
|---|---|---|---|---|---|---|
| EGFR+/IHC+ | 28 | 50% | 60% | 10 (2-16) | 21 (10-21) | 63% (45-81) |
|  |  | p-value* <0.001 | p-value* = 0.086 | p-value* = 0.04 | p-value* = 0.06 |  |
| EGFR+ or IHC+ | 77 | 12% | 47% | 3 (2-5) | 12 (8-15) | 50% (39-61) |
| EGFR−/IHC− | 47 | 2% | 25% | 2 (2-3) | 7 (5-12) | 37% (23-51) |

*p-value of EGFR+/IHC+ versus other two groups

In conclusion, combination of EGFR mutation and EGFR protein expression can be used to select lung cancer patients, who will benefit from those, who most likely will not benefit from EGFR inhibitor therapy.

(5) Combination of EGFR Protein Expression and Activated (Phosphorylated) AKT Protein Expression as Predictor for Outcome to EGFR Inhibitors in NSCLC Patients As shown in Table 17, one hundred and eighty-two patients had a positive test for EGFR protein expression (detected by IHC) and phosphorylated AKT expression (detected by IHC). Double positive test was found in 78 patients, and they had a response rate of 30%, disease control rate of 64%, time to progression 6 months, median survival 16 months and 1-year survival 63%.

TABLE 17

Combined P-AKT and IHC results (n = 182 patients)

|  | No. pts | RSP | DCR | TTP (mo) | MS (mo) | 1-yr |
|---|---|---|---|---|---|---|
| P-AKT+/IHC+ | 78 | 30% | 64% | 6 (4-10) | 16 (12-21) | 63% (51-74) |
|  |  | p-value* <0.001 | p-value* = 0.003 | p-value* <0.001 | p-value* = 0.004 |  |
| P-AKT+ or IHC+ | 84 | 6% | 34% | 3 (2-3) | 8 (6-14) | 43% (32-54) |
| P-AKT−/IHC− | 23 | 0% | 21% | 2 (2-4) | 6 (5-9) | 30% (12-49) |

*p-value of P-AKT+/IHC+ versus other two groups

In contrast, among the 23 patients with double negative test none had objective response, 21% had disease control, time to progression was 2 months, median survival was 6 months and 1-year survival was 30%. In all the mentioned clinical outcome parameters was there a statistical difference (p<0.05) between the double positive group and the double negative group.

In conclusion, combination of EGFR protein expression detected by IHC and phosphorylated AKT detected by IHC can be used to select lung cancer patients, who will most likely have clinical benefit from EGFR inhibitor therapy, and those patients, who most likely will not have any clinical benefit from such a treatment.

(6) Combination of Increased Gene Copy Number Detected by FISH and EGFR Mutations as Predictor for Outcome to EGFR Inhibitors in NSCLC Patients.

As shown in Table 18, altogether 143 patients were studied both for EGFR gene copy number and EGFR mutations.

TABLE 18

Combined FISH and EGFR mutation results (n = 143 patients)

| | No. pts | RSP | DCR | TTP (mo) | MS (mo) | 1-yr |
|---|---|---|---|---|---|---|
| FISH+/ EGFR+ | 17 | 69% p-value* <0.001 | 69% p-value* = 0.031 | 16 (3-20) p-value* = 0.004 | NR p-value* = 0.003 | 67% (71-100) |
| FISH+ or EGFR + | 46 | 15% | 45% | 3 (2-5) | 10 (5-14) | 45% (30-59) |
| FISH−/EGFR− | 80 | 3% | 29% | 3 (2-3) | 10 (6-13) | 42% (31-53) |

*p-value of FISH+/EGFR+ versus other two groups

Among the 17 patients, who had double positive tests, the response rate was 69%, disease control rate was 69%, time to progression was 16 months, median survival was not yet achieved, but exceeding 20 months, and 1-year survival was 67%. All these parameters were statistical significantly better than the out come for the patients with the double negative tests. They had response rate of 3%, disease control rate of 29%, time to progression 3 month, median survival 10 months and 1-year survival 42%.

In conclusion, the combination of increased EGFR gene copy number detected by FISH and EGFR mutations can be used to select the patients, who will have clinical benefit from EGFR inhibitor therapy.

(7) Combination of Increased EGFR Gene Copy Number, EGFR Protein Expression and EGFR Mutation Predicts Superior Clinical Outcome to EGFR Inhibitor Therapy in NSCLC Patients.

As shown in Table 19, the combined data analysis from the Italian cohort and the Southwest Oncology Group study cohort demonstrated that among 12 patients, who had triple positive tests had very high response rate of 78%, disease control rate of 78%, time to progression of 20 months, median survival, which was not yet achieved but exceeding 20 months, and 1-year survival of 100%.

TABLE 19

| FISH | IHC | EGFR Mut | n | OR | DCR | TTP | OS | 1-yr surv |
|---|---|---|---|---|---|---|---|---|
| + | + | + | 12 | 78% | 78% | 20 (11-20) | NR | 100% |
| + | + | − | 20 | 22% | 61% | 5 (3-12) | 15 (6-16) | 64% (42-86) |
| + | − | + | 5 | 50% | 50% | 3 (2-9) | NR | 60% (17-100) |
| − | + | + | 12 | 22% | 44% | 4 (2-7) | 11 (3-11) | 42% (1470) |
| + | − | − | 8 | 0% | 39% | 2 (1-6) | 9 (1-9) | 38% (7-66) |
| − | + | − | 39 | 3% | 41% | 3 (2-5) | 11 (8-18) | 49% (33-64) |
| − | − | + | 6 | 0% | 0% | 2 (1-2) | 3 (1-3) | 0% (0-30) |
| − | − | − | 37 | 3% | 21% | 2 (2-3) | 6 (4-12) | 37% (21-52) |

In conclusion, combination of increased EGFR gene copy number detected by FISH, EGFR protein expression detected by IHC and EGFR mutations can be used to select patients, who will have good clinical outcome after EGFR inhibitor therapy.

(8) Combination of EGFR Gene Copy Number, EGFR Protein Expression and Phosphorylated AKT Expression Predicts Superior Clinical Outcome After EGFR Inhibitor Therapy of NSCLC Patients.

As shown in Table 20, in the combined data analysis from the Italian cohort and the Southwest Oncology Group Study cohort we demonstrated that the patients with triple positive tests had a high response rate of 43%, disease control rate of 80%, time to progression of 12 months, median survival not achieved yet, but exceeding 20 months and 1-year survival of 84%.

TABLE 20

| FISH | IHC | P-AKT | N | OR | DCR | TTP | OS | 1-yr surv |
|---|---|---|---|---|---|---|---|---|
| + | + | + | 34 | 43% | 80% | 12 (6-19) | NR | 84% (70-97) |
| + | + | − | 4 | 0% | 67% | 9 (2-9) | 18 (5-18) | 75% (33-100) |
| + | − | + | 15 | 15% | 46% | 3 (2-6) | 14 (3-19) | 53% (28-79) |
| − | + | + | 35 | 13% | 47% | 4 (2-6) | 11 (6-15) | 43% (26-59) |
| + | − | − | 2 | 0% | 0% | 2 (NA) | 9 (NA) | 0% (0-69) |
| − | + | − | 23 | 6% | 50% | 4 (2-7) | 9 (7-9) | 47% (27-68) |
| − | − | + | 32 | 4% | 18% | 2 (2-3) | 6 (4-10) | 29% (13-44) |
| − | − | − | 17 | 0% | 14% | 2 (2-5) | 6 (4-12) | 29% (8-51) |

(9) Multivariable Analysis Demonstrates That Both Increased EGFR Gene Copy Number and Increased EGFR Protein Expression are Independent Prognostic/Predictive Factors for Survival Outcome in NSCLC Patients Treated with EGFR Inhibitors:

Multivariable analysis including data from the Italian study cohort and the Southwest Oncology Group clinical trial 0126 demonstrated that both increased EGFR gene copy number detected by FISH and increased EGFR protein expression detected by IHC were independent prognostic/predictive factors for survival (Table 21). The multivariable analysis is based on an initial univariable analysis including clinical- and biological markers by using backward stepwise regression methods. All univariately significant covariates were included in the stepwise selection.

TABLE 21

Multivariabel analysis of predictive/prognostic factors in 179 NSCLC patients treated with gefitinib.

| VARIABLE | No. patients | HR | p-value |
|---|---|---|---|
| Current/Former smokers | 142 | 2.68 | 0.0005 |
| Performance status 2 | 24 | 3.64 | 0.0001 |
| FISH− | 120 | 1.87 | 0.006 |
| IHC− | 71 | 1.70 | 0.007 |

In conclusion, each of the markers: EGFR gene copy number detected by FISH, EGFR protein expression detected by IHC and expression of activated (phosphorylated) AKT, HER2 gene copy number and EGFR mutation analysis can be used for the selection of lung cancer patients, who will have a good clinical outcome after EGFR inhibitor therapy. The combined data analysis performed based on the two studies showed that combinations of tests gives a very high prediction of which patients will benefit from EGFR inhibitors and who will not. The combination of the analysis of EGFR gene copy number by FISH and EGFR protein expression by IHC demonstrated a very strong prediction for increased response, increased time to progression and significantly prolonged survival (median 21 months) compared to the results from unselected patients. The data showed also that patients with no or low EGFR gene copy number (FISH negative) and no or low EGFR protein expression did not benefit from EGFR inhibitor therapy as there were no responders and only one patients classified as having stable disease. However, the time to progression was very short and median survival in this group was 6 months. The group of patients with "double negative" tests had a similar outcome as the placebo treated patients in the Canadian study, BR-21, in which a similar group of advanced NSCLC patients, who had previously failed on at least one previous chemotherapy regimen were randomized to placebo or erlotinib (Tsao et al., JCO 23:16S:622S #7007). Thus, a combination of two established clinical applicable tests (FISH and IHC), are in the inventors' studies demonstrated to be of significant value for selection of cancer patients to EGFR inhibitors.

Example 9

The following example demonstrates that EGFR and HER2 gene copy numbers detected by FISH are associated with sensitivity to Cetuximab (C225, Erbitux™ BMS/Imclone) in NSCLC cell lines.

Studies performed in 25 NSCLC cell lines showed that 5 lines were sensitive to Cetuximab ($IC_{50} < 1$ uM) and 20 lines were resistant (IC50 >1 uM). All five sensitive cell lines, namely H827, H3255, H358, H2279 and Calu 3, displayed EGFR and/or HER2 gene amplification by FISH. Conversely, among the 20 NSCLC lines which were resistant to Cetuximab, none had EGFR or HER2 gene amplification and only 6 had high polysomy for EGFR and/or HER2. The distribution of NSCLC lines with high level of genomic gain and no/low level of genomic gain was significantly different between the Cetuximab sensitive and Cetuximab resistant lines (chi-square 10.84, p<0.001). These results support the conclusion that copy number status of the EGFR and HER2 genes is a predictor of sensitivity to antibody therapy.

Each reference cited herein is incorporated by reference in its entirety. U.S. Provisional Patent Application Ser. No. 60/575,789, filed May 27, 2004, is specifically incorporated herein by reference in its entirety.

REFERENCES

Arteaga, Sem Oncol 2002; 29:3-9.
Andrecheck et al. Proc Natl Acad Sc USA 2000; 97:3444-49.
Armitage and Berry, Statistical Methods in Medical Research. Blackwell Scientific Publication Limited, Oxford, 1994.
Bailey et al., Lung Cancer 2003; 41:s71 (abstr).
Barsky et al., Cancer 73: 1163-1170, 1994
Bartlett et al., J Pathol 2003; 199:411-7.
Baselga et al., J Clin Oncol. 2002; 20:4292-302.
Bianco et al., Oncogene 2003; 22:2812-22

Breathnach et al., *Cancer* 86: 1165-1173, 1999
Cappuzzo et al., *J Clin Oncol* 2003; 21:2658-63.
Cappuzzo et al., *Proc Am Soc Clin Oncol* 2004; 23:3004.
Cappuzzo et al., *Natl Cancer Inst* 2004; 96:1133-41.
Cappuzzo et al., *J Natl Cancer Inst*, in press.
Ciardello and Tortora, *Clin Cancer Res* 2001; 7:2958-70.
Ciardiello et al., *Clin Cancer Res* 2000; 6:2053-63.
Cox, *J R Stat Soc B* 1972; 34:187-220.
Datta S R, *Genes and Development* 1999; 13:2905-27.
Demetri et al., *N Engl J Med* 2002; 347:472-80.
Druker et al., *N Engl J Med* 2001; 344:1031-7.
Frederick et al., *Cancer Res* 2000; 60, 1383-87.
Fukuoka et al., *J Clin Oncol.* 2003; 21:2237-46.
Furak et al., *European J Cardio-Thoracic Surgery* 23:818-823, 2003.
Gandara et al., *Clin Cancer Res* 10: 4205-4209, 2004.
Giaccone et al., *J Clin Oncol* 2004; 22:777-84
Herbst et al., *J Clin Oncol.* 2002; 20:3815-25.
Herbst et al., *Proc Am Soc Clin Oncol* 23; 617, 2004.
Hidalgo et al., *J Clin Oncol.* 2001; 19:3267-79.
Hirsch et al., *Lung Cancer* 2003; 41 Suppl 1:S29-42.
Hirsch et al., *Br J Cancer* 86: 1449-1456, 2002
Hirsch et al., *J Clin Oncol* 2003; 21:3798-807.
Hirsch et al., *Lung Cancer* 2003; 41 Suppl 1:S29-42.
Janmaat et al., *Clin Cancer Res* 2003; 9:2316-26.
Kaplan and Meier, *J Am Stat Assoc* 1985; 53:457-81.
Kelly et al., *J Clin Oncol.* 2001; 19:3210-8.
Kris et al., *JAMA* 2003; 290:2149-58.
Kris et al., *Lung Cancer* 2000; Suppl 1; 29:233 abstract.
Levitt and Koty, *Investig New Drugs* 1999; 7:213-26.
Levitzki and Gazit, *Science* 1995; 267:1782-8.
Lynch et al., *N Engl J Med* 2004; 350:2129-39
Mantel N, *Cancer Chemother Rep* 50:163-170, 1966.
Miller et al., *J Clin Oncol.* 2004; 22:1103-9.
Miller et al., *Proc Am Soc Clin Oncol* 2003; 22 (abstract 2491).
Non-small cell Lung Cancer Collaborative Group. *BMJ* 1995; 311:899-909.
Oken et al., *Am J Clin Oncol* 1982; 5:649-655.
Ono et al., *Mol Cancer Ther* 2004; 3:465-72
Paez et al., *Science* 2004; 304:1497-1500.
Pao et al., *PNAS* 2004; 101: 13306-11.
Parkin, *Lancet Oncology* 2001, 2:533-43.
Parra et al., *Brit J Cancer,* 91: 208-212, 2004.
Patel et al., *Lung Cancer* 41:S56, 2003 (suppl 2).
Perez-Soler et al., *J Clin Oncol* 2004; 22:3238-47.
Perez-Soler et al., *Proc. Am. Soc. Clin. Oncol.,* 20: 310a 2001.
Ranson et al., *J Clin Oncol.* 2002; 20:2240-50.
Reissmann et al., *J Cancer Res Clin Oncol* 1999; 125: 61-70.
Rosell et al., *Clin Cancer Res* 2004; 10:1318-25.
Salomon et al., *Crit Rev Oncol Hematol* 1995; 19:183-232.
Salomon et al., *Signal* 2001; 2:4-11.
Schiller et al., *N Engl J Med* 2002; 346:92-8.
Shepherd et al., *Proc Am Soc Clin Oncol* 2004; 23 (abstract).
Slamon et al., *N Engl J Med* 2001; 344:783-92.
Slamon et al., *Science* 235:177-182, 1987.
Sordella et al., *Science* 2004; 305:1163-7
Therasse, *J Nat Cancer Inst* 2000; 92:205-16.
Tracy et al., *Cancer Res* 2004; 64:7241-44.
Travis et al., Histological typing of lung and pleural tumors. Third edition, Berlin: Springer, 1999.
Vogel et al., *J Clin Oncol* 2002; 20:719-26.
West et al., Advanced bronchioloalveolar carcinoma: a phase II trial of paclitaxel by 96-h infusion (SWOG 9714): a Southwest Oncology Group study. Ann Oncol, in press While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

---

What is claimed is:

1. A method to select a non-small cell lung cancer patient (NSCLC) patient as being predicted to respond to therapeutic administration of an EGFR inhibitor comprising:

a) determining by immunohistochemistry an EGFR fraction score, wherein the EGFR fraction score corresponds to the percentage of cells in a tumor tissue specimen received from a NSCLC patient that stain positive for EGFR protein expressed as a number between 0 and 100 corresponding to the percentage of cells in the sample of tumor cells staining positive for the EGFR protein between 0% and 100%;

b) determining an EGFR intensity score that corresponds to the staining intensity of the EGFR protein in the specimen of tumor cells expressed as a number of at least 1 and not greater than 4 corresponding to the intensity of the staining of the EGFR protein in the sample of tumor cells;

c) calculating an EGFR expression score that is the product of the EGFR fraction score and the EGFR intensity score expressed as an integer between 0 and 400 corresponding to the numerical product of the EGFR fraction score, expressed as a number between 0 and 100, and the EGFR intensity score, expressed as a number of at least one 1 and not greater than 4;

d) determining by immunohistochemistry a P-AKT fraction score, wherein the P-AKT fraction score corresponds to the percentage of cells in a tumor tissue specimen received from a NSCLC patient that stain positive for phosphorylated AKT protein expressed as a number between 0 and 100 corresponding to the percentage of cells in the sample of tumor cells staining positive for the phosphorylated AKT protein between 0% and 100%;

e) determining a P-AKT intensity score that corresponds to the staining intensity of the phosphorylated AKT protein in the specimen of tumor cells expressed as a number of at least 1 and not greater than 4 corresponding to the intensity of the staining of the phosphorylated AKT protein in the sample of tumor cells;

f) calculating a P-AKT expression score that is the product of the P-AKT fraction score and the P-AKT intensity score expressed as an integer between 0 and 400 corresponding to the numerical product of the P-AKT fraction score, expressed as a number between 0 and 100, and the P-AKT intensity score, expressed as a number of at least one 1 and not greater than 4;

g) selecting the NSCLC patient as being predicted to respond to therapeutic administration of an EGFR inhibitor, if the EGFR expression score and the P-AKT expression score are each equal to or greater than 200; or h) selecting the NSCLC patient as being predicted to not respond to therapeutic administration of an EGFR inhibitor, if the EGFR expression score is equal to or greater than 200 and the P-AKT expression score is less than 200.

* * * * *

SEQUENCE LISTING

```
<160> NUMBER OF SEQ ID NOS: 24

<210> SEQ ID NO 1
<211> LENGTH: 19
<212> TYPE: DNA
<213> ORGANISM: Homo sapiens

<400> SEQUENCE: 1
tccgtctctt gccgggaat                                                  19

<210> SEQ ID NO 2
<211> LENGTH: 20
<212> TYPE: DNA
<213> ORGANISM: Homo sapiens

<400> SEQUENCE: 2
ggctcaccct ccagaaccttt                                                20

<210> SEQ ID NO 3
<211> LENGTH: 21
<212> TYPE: DNA
<213> ORGANISM: Homo sapiens

<400> SEQUENCE: 3
acgcattccc tgcctcggct g                                               21
```

<210> SEQ ID NO 4
<211> LENGTH: 18
<212> TYPE: PRT
<213> ORGANISM: Homo sapiens

<400> SEQUENCE: 4

Lys Ile Pro Val Ala Ile Lys Glu Leu Arg Glu Ala Thr Ser Pro Lys
1               5                   10                  15

Ala Asn

<210> SEQ ID NO 5
<211> LENGTH: 54
<212> TYPE: DNA
<213> ORGANISM: Homo sapiens

<400> SEQUENCE: 5
aaaattcccg tcgctatcaa ggaattaaga gaagcaacat ctccgaaagc caac        54

<210> SEQ ID NO 6
<211> LENGTH: 36
<212> TYPE: DNA
<213> ORGANISM: Homo sapiens

<400> SEQUENCE: 6
aaaattcccg tcgctatcaa gtctccgaaa gccaac                            36

<210> SEQ ID NO 7
<211> LENGTH: 39
<212> TYPE: DNA
<213> ORGANISM: Homo sapiens

<400> SEQUENCE: 7
aaaattcccg tcgctatcaa aacatctccg aaagccaac                         39

<210> SEQ ID NO 8
<211> LENGTH: 39
<212> TYPE: DNA
<213> ORGANISM: Homo sapiens

<400> SEQUENCE: 8
aaaattcccg tcgctatcaa ggaatctccg aaagccaac                         39

<210> SEQ ID NO 9
<211> LENGTH: 39
<212> TYPE: DNA
<213> ORGANISM: Homo sapiens

<400> SEQUENCE: 9
aaaattcccg tcgctatcaa gacatctccg aaagccaac                         39

<210> SEQ ID NO 10
<211> LENGTH: 14
<212> TYPE: PRT
<213> ORGANISM: Homo sapiens

<400> SEQUENCE: 10

His Val Lys Ile Thr Asp Phe Gly Leu Ala Lys Leu Leu Gly
1               5                   10

<210> SEQ ID NO 11
<211> LENGTH: 42
<212> TYPE: DNA

<213> ORGANISM: Homo sapiens

<400> SEQUENCE: 11
catgtcaaga tcacagattt tgggctggcc aaactgctgg gt                          42

<210> SEQ ID NO 12
<211> LENGTH: 14
<212> TYPE: PRT
<213> ORGANISM: Homo sapiens

<400> SEQUENCE: 12

His Val Lys Ile Thr Asp Phe Gly Arg Ala Lys Leu Leu Gly
1               5                   10

<210> SEQ ID NO 13
<211> LENGTH: 42
<212> TYPE: DNA
<213> ORGANISM: Homo sapiens

<400> SEQUENCE: 13
catgtcaaga tcacagattt tgggcgggcc aaactgctgg gt                          42

<210> SEQ ID NO 14
<211> LENGTH: 14
<212> TYPE: PRT
<213> ORGANISM: Homo sapiens

<400> SEQUENCE: 14

His Ile Lys Ile Thr Asp Phe Gly Leu Ala Lys Leu Leu Gly
1               5                   10

<210> SEQ ID NO 15
<211> LENGTH: 42
<212> TYPE: DNA
<213> ORGANISM: Homo sapiens

<400> SEQUENCE: 15
catatcaaga tcacagattt tgggctggcc aaactgctgg gt                          42

<210> SEQ ID NO 16
<211> LENGTH: 23
<212> TYPE: DNA
<213> ORGANISM: Homo sapiens

<400> SEQUENCE: 16
gacccttgtc tctgtgttct tgt                                               23

<210> SEQ ID NO 17
<211> LENGTH: 23
<212> TYPE: DNA
<213> ORGANISM: Homo sapiens

<400> SEQUENCE: 17
tatacagctt gcaaggactc tgg                                               23

<210> SEQ ID NO 18
<211> LENGTH: 20
<212> TYPE: DNA
<213> ORGANISM: Homo sapiens

<400> SEQUENCE: 18
ccagaccatg agaggccctg                                                   20

```
<210> SEQ ID NO 19
<211> LENGTH: 23
<212> TYPE: DNA
<213> ORGANISM: Homo sapiens

<400> SEQUENCE: 19
cacaattgcc agttaacgtc ttc                                          23

<210> SEQ ID NO 20
<211> LENGTH: 20
<212> TYPE: DNA
<213> ORGANISM: Homo sapiens

<400> SEQUENCE: 20
agggtctaga gcagagcagc                                              20

<210> SEQ ID NO 21
<211> LENGTH: 19
<212> TYPE: DNA
<213> ORGANISM: Homo sapiens

<400> SEQUENCE: 21
gcctgaggtt cagagccat                                               19

<210> SEQ ID NO 22
<211> LENGTH: 22
<212> TYPE: DNA
<213> ORGANISM: Homo sapiens

<400> SEQUENCE: 22
catgatgatc tgtccctcac ag                                           22

<210> SEQ ID NO 23
<211> LENGTH: 20
<212> TYPE: DNA
<213> ORGANISM: Homo sapiens

<400> SEQUENCE: 23
ctggtccctg gtgtcaggaa                                              20

<210> SEQ ID NO 24
<211> LENGTH: 21
<212> TYPE: DNA
<213> ORGANISM: Homo sapiens

<400> SEQUENCE: 24
gctggctgac ctaaagccac c                                            21
```